United States Patent
Votteler et al.

(10) Patent No.: US 12,415,837 B2
(45) Date of Patent: Sep. 16, 2025

(54) ENGINEERING VIRUS-LIKE NANOCARRIERS FOR BIOMOLECULE DELIVERY

(71) Applicant: University of Utah Research Foundation, Salt Lake City, UT (US)

(72) Inventors: Jörg Philip Votteler, Murray, UT (US); Wesley I. Sundquist, Salt Lake City, UT (US); Neil P. King, Seattle, WA (US)

(73) Assignee: University of Utah Research Foundation, Salt Lake City, UT (US)

( * ) Notice: Subject to any disclaimer, the term of this patent is extended or adjusted under 35 U.S.C. 154(b) by 479 days.

(21) Appl. No.: 16/664,078

(22) Filed: Oct. 25, 2019

(65) Prior Publication Data

US 2020/0140493 A1    May 7, 2020

Related U.S. Application Data

(60) Provisional application No. 62/751,457, filed on Oct. 26, 2018.

(51) Int. Cl.

| | |
|---|---|
| *C07K 14/005* | (2006.01) |
| *A61K 47/69* | (2017.01) |
| *C07K 14/01* | (2006.01) |
| *C07K 14/075* | (2006.01) |
| *C07K 14/08* | (2006.01) |
| *C12N 7/00* | (2006.01) |

(52) U.S. Cl.
CPC .......... *C07K 14/08* (2013.01); *A61K 47/6901* (2017.08); *C07K 14/075* (2013.01); *C12N 7/00* (2013.01); *C12N 2710/10042* (2013.01); *C12N 2770/30032* (2013.01); *C12N 2770/30042* (2013.01)

(58) Field of Classification Search
None
See application file for complete search history.

(56) References Cited

U.S. PATENT DOCUMENTS

| 2017/0121388 A1* | 5/2017 | Jaeger | C07K 14/7158 |
| 2018/0030429 A1* | 2/2018 | King | C07K 14/435 |

OTHER PUBLICATIONS

Feng et al. A pathogenic picornavirus acquires an envelope by hijacking cellular membranes. Nature, 2013, 496: 367-371.*
Votteler et al. Designed proteins induce the formation of nanocage-containing extracellular vesicles. Nature, 2016, 540: 292-295.*
Zhandina et al. Functional Interchangeability of Late Domains, Late Domain Cofactors and Ubiquitin in Viral Budding. PLoS Pathog, 2010, 6(10): e1001153.*
Li et al. Fabrication of Nanoarchitectures Templated by Virus-Based Nanoparticles: Strategies and Applications. Small 2014, 10, No. 2, 230-245.*
Altan-Bonnet, N., *Extracellular vesicles are the Trojan horses of viral infection*. Current opinion in microbiology, 2016. 32: p. 77-81.
Votteler, J., et al., Designed proteins induce the formation of nanocage-containing extracellular vesicles. Nature, 2016. 540(7632): p. 292-295.
Manayani, D.J., et al., A viral nanoparticle with dual function as an anthrax antitoxin and vaccine. PLoS pathogens, 2007. 3(10).
Gibson, D.G., et al., Enzymatic assembly of DNA molecules up to several hundred kilobases. Nature Methods, 2009. 6(5): p. 343-345.
Kunkel, T.A., *Rapid and efficient site-specific mutagenesis without phenotypic selection*. Proceedings of the National Academy of Sciences of the United States of America, 1985. 82(2): p. 488-492.
Thery, C., et al., Isolation and characterization of exosomes from cell culture supernatants and biological fluids. Curr Protoc Cell Biol, 2006. Chapter 3: p. Unit 3 22.
U.S. Appl. No. 62/751,457, filed Oct. 26, 2018, Votteler.

* cited by examiner

*Primary Examiner* — Nianxiang Zou
(74) *Attorney, Agent, or Firm* — BALLARD SPAHR LLP

(57) ABSTRACT

Disclosed herein are modified capsid proteins comprising a capsid forming protein, a membrane binding element and an ESCRT-recruiting element, wherein at least one of the membrane binding element and the ESCRT-recruiting element is heterologous to the capsid forming protein. Disclosed are capsids comprising a plurality of modified capsid proteins. Disclosed are multimeric assemblies comprising a plurality of capsids within a membrane. Also disclosed are modified non-enveloped viruses comprising a capsid wherein the capsid comprises a plurality of modified capsid proteins, wherein the plurality of modified capsid proteins comprise a capsid forming protein, a membrane binding element and an ESCRT-recruiting element, wherein at least one of the membrane binding element and the ESCRT-recruiting element is heterologous to the modified capsid protein, wherein the capsid forming protein is a capsid forming protein of a non-enveloped virus.

14 Claims, 7 Drawing Sheets

Specification includes a Sequence Listing.

A) Enveloped Nodaviruses

Flock House Virus

Nodamura Virus

SEQUENCE LISTING

```
<160> NUMBER OF SEQ ID NOS: 188

<210> SEQ ID NO 1
<211> LENGTH: 5
<212> TYPE: PRT
<213> ORGANISM: Artificial Sequence
<220> FEATURE:
<223> OTHER INFORMATION: synthetic construct; motif
<220> FEATURE:
<221> NAME/KEY: MISC_FEATURE
<222> LOCATION: (1)..(1)
<223> OTHER INFORMATION: Contains myristoylation motif
<220> FEATURE:
<221> NAME/KEY: MISC_FEATURE
<222> LOCATION: (2)..(4)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Ser or Thr

<400> SEQUENCE: 1

Gly Xaa Xaa Xaa Xaa
1               5
```

```
<210> SEQ ID NO 2
<211> LENGTH: 5
<212> TYPE: PRT
<213> ORGANISM: Artificial Sequence
<220> FEATURE:
<223> OTHER INFORMATION: synthetic construct; motif
<220> FEATURE:
<221> NAME/KEY: MISC_FEATURE
<222> LOCATION: (1)..(1)
<223> OTHER INFORMATION: Contains myristoylation motif

<400> SEQUENCE: 2

Gly Ala Arg Ala Ser
1               5

<210> SEQ ID NO 3
<211> LENGTH: 5
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 3

Gly Ala Gln Phe Ser
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic construct; motif
<220> FEATURE:
<221> NAME/KEY: MISC
<222> LOCATION: (1)..(1)
<223> OTHER INFORMATION: Contains myristoylation motif

<400> SEQUENCE: 4

Gly Ser Ser Lys Ser
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic construct; motif
<220> FEATURE:
<221> NAME/KEY: MISC
<222> LOCATION: (1)..(1)
<223> OTHER INFORMATION: Contains myristoylation motif

<400> SEQUENCE: 5

Gly Lys Gln Asn Ser
1               5

<210> SEQ ID NO 6
<211> LENGTH: 12
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
```

```
<223> OTHER INFORMATION: Contains myristoylation motif

<400> SEQUENCE: 6

Gly Cys Ile Lys Ser Lys Arg Lys Asp Asn Leu Asn
1               5                   10

<210> SEQ ID NO 7
<211> LENGTH: 12
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 7

Gly Cys Thr Leu Ser Ala Glu Glu Arg Ala Ala Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 8

Leu Cys Cys Met Arg Arg Thr Lys Gln Val Glu Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 9

Asp Cys Leu Cys Ile Val Thr Thr Lys Lys Tyr Arg
1               5                   10

<210> SEQ ID NO 10
<211> LENGTH: 13
<212> TYPE: PRT
<213> ORGANISM: Artificial Sequence
<220> FEATURE:
<223> OTHER INFORMATION: synthetic construct; motif

<400> SEQUENCE: 10

Lys Lys Lys Lys Lys Ser Lys Thr Lys Cys Val Ile Met
1               5                   10

<210> SEQ ID NO 11
<211> LENGTH: 13
<212> TYPE: PRT
<213> ORGANISM: Artificial Sequence
<220> FEATURE:
<223> OTHER INFORMATION: synthetic construct; motif
```

```
<400> SEQUENCE: 11

Asp Met Lys Lys His Arg Cys Lys Cys Cys Ser Ile Met
1               5                   10

<210> SEQ ID NO 12
<211> LENGTH: 13
<212> TYPE: PRT
<213> ORGANISM: Artificial Sequence
<220> FEATURE:
<223> OTHER INFORMATION: synthetic construct; motif

<400> SEQUENCE: 12

Ala Gln Arg Gln Lys Lys Arg Arg Leu Cys Leu Leu Leu
1               5                   10

<210> SEQ ID NO 13
<211> LENGTH: 13
<212> TYPE: PRT
<213> ORGANISM: Artificial Sequence
<220> FEATURE:
<223> OTHER INFORMATION: synthetic construct; motif

<400> SEQUENCE: 13

Ala Gln Glu Phe Ile His Gln Phe Leu Cys Asn Pro Leu
1               5                   10

<210> SEQ ID NO 14
<211> LENGTH: 130
<212> TYPE: PRT
<213> ORGANISM: Artificial Sequence
<220> FEATURE:
<223> OTHER INFORMATION: synthetic construct; rat PLC5

<400> SEQUENCE: 14

His Gly Leu Gln Asp Asp Pro Asp Leu Gln Ala Leu Leu Lys Gly Ser
1               5                   10                  15

Gln Leu Leu Lys Val Lys Ser Ser Ser Trp Arg Arg Glu Arg Phe Tyr
            20                  25                  30

Lys Leu Gln Glu Asp Cys Lys Thr Ile Trp Gln Glu Ser Arg Lys Val
        35                  40                  45

Met Arg Ser Pro Glu Ser Gln Leu Phe Ser Ile Glu Asp Ile Gln Glu
    50                  55                  60

Val Arg Met Gly His Arg Thr Glu Gly Leu Glu Lys Phe Ala Arg Asp
65                  70                  75                  80

Ile Pro Glu Asp Arg Cys Phe Ser Ile Val Phe Lys Asp Gln Arg Asn
                85                  90                  95

Thr Leu Asp Leu Ile Ala Pro Ser Pro Ala Asp Ala Gln His Trp Val
            100                 105                 110

Gln Gly Leu Arg Lys Ile Ile His Ser Gly Ser Met Asp Gln Arg
        115                 120                 125

Gln Lys
    130

<210> SEQ ID NO 15
<211> LENGTH: 52
<212> TYPE: PRT
<213> ORGANISM: Artificial Sequence
<220> FEATURE:
<223> OTHER INFORMATION: synthetic construct; PCK5 isoform X2

<400> SEQUENCE: 15

Pro His Arg Phe Lys Val His Asn Tyr Met Ser Pro Thr Phe Cys Asp
```

```
  1               5                  10                  15
His Cys Gly Ser Leu Leu Trp Gly Leu Val Lys Gln Gly Leu Lys Cys
                20                  25                  30

Glu Asp Cys Gly Met Asn Val His His Lys Cys Arg Glu Lys Val Ala
                35                  40                  45

Asn Leu Cys Gly
           50
```

<210> SEQ ID NO 16
<211> LENGTH: 126
<212> TYPE: PRT
<213> ORGANISM: Artificial Sequence
<220> FEATURE:
<223> OTHER INFORMATION: synthetic construct; mouse PI3K

<400> SEQUENCE: 16

```
Gly Ala Val Lys Leu Ser Val Ser Tyr Arg Asn Gly Thr Leu Phe Ile
1               5                  10                  15

Met Val Met His Ile Lys Asp Leu Val Thr Glu Asp Gly Ala Asp Pro
                20                  25                  30

Asn Pro Tyr Val Lys Thr Tyr Leu Leu Pro Asp Thr His Lys Thr Ser
                35                  40                  45

Lys Arg Lys Thr Lys Ile Ser Arg Lys Thr Arg Asn Pro Thr Phe Asn
           50                  55                  60

Glu Met Leu Val Tyr Ser Gly Tyr Ser Lys Glu Thr Leu Arg Gln Arg
65                  70                  75                  80

Glu Leu Gln Leu Ser Val Leu Ser Ala Glu Ser Leu Arg Glu Asn Phe
                85                  90                  95

Phe Leu Gly Gly Ile Thr Leu Pro Leu Lys Asp Phe Asn Leu Ser Lys
                100                 105                 110

Glu Thr Val Lys Trp Tyr Gln Leu Thr Ala Ala Thr Tyr Leu
                115                 120             125
```

<210> SEQ ID NO 17
<211> LENGTH: 148
<212> TYPE: PRT
<213> ORGANISM: Artificial Sequence
<220> FEATURE:
<223> OTHER INFORMATION: synthetic construct; p40phox

<400> SEQUENCE: 17

```
Ala Val Ala Gln Gln Leu Arg Ala Glu Ser Asp Phe Glu Gln Leu Pro
1               5                  10                  15

Asp Asp Val Ala Ile Ser Ala Asn Ile Ala Asp Ile Glu Glu Lys Arg
                20                  25                  30

Gly Phe Thr Ser His Phe Val Phe Val Ile Glu Val Lys Thr Lys Gly
                35                  40                  45

Gly Ser Lys Tyr Leu Ile Tyr Arg Arg Tyr Arg Gln Phe His Ala Leu
           50                  55                  60

Gln Ser Lys Leu Glu Glu Arg Phe Gly Pro Asp Ser Lys Ser Ser Ala
65                  70                  75                  80

Leu Ala Cys Thr Leu Pro Thr Leu Pro Ala Lys Val Tyr Val Gly Val
                85                  90                  95

Lys Gln Glu Ile Ala Glu Met Arg Ile Pro Ala Leu Asn Ala Tyr Met
                100                 105                 110

Lys Ser Leu Leu Ser Leu Pro Val Trp Val Leu Met Asp Glu Asp Val
                115                 120                 125
```

```
Arg Ile Phe Phe Tyr Gln Ser Pro Tyr Asp Ser Glu Gln Val Pro Gln
            130                 135                 140

Ala Leu Arg Arg
145

<210> SEQ ID NO 18
<211> LENGTH: 12
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 18

Gly Cys Ile Lys Ser Lys Gly Lys Asp Ser Leu Ser
1               5                   10

<210> SEQ ID NO 19
<211> LENGTH: 9
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 19

Gly Cys Ile Asn Ser Lys Arg Lys Asp
1               5

<210> SEQ ID NO 20
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 20

Gly Ser Ser Lys Ser Lys Pro Lys Asp Pro Ser Gln Arg Arg Arg
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 21

Gly Cys Ile Lys Ser Lys Glu Asp Lys Gly Pro Ala Met Lys Tyr
1               5                   10                  15

<210> SEQ ID NO 22
<211> LENGTH: 18
<212> TYPE: PRT
<213> ORGANISM: Artificial Sequence
```

<220> FEATURE:
<223> OTHER INFORMATION: synthetic construct; ESCRT-recruiting element

<400> SEQUENCE: 22

Ala Ala Gly Ala Tyr Asp Pro Ala Arg Lys Leu Leu Glu Gln Tyr Ala
1               5                   10                  15

Lys Lys

<210> SEQ ID NO 23
<211> LENGTH: 80
<212> TYPE: PRT
<213> ORGANISM: Artificial Sequence
<220> FEATURE:
<223> OTHER INFORMATION: synthetic construct; ESCRT-recruiting element

<400> SEQUENCE: 23

Pro Asn Cys Phe Asn Ser Ser Ile Asn Asn Ile His Glu Met Glu Ile
1               5                   10                  15

Gln Leu Lys Asp Ala Leu Glu Lys Asn Gln Gln Trp Leu Val Tyr Asp
            20                  25                  30

Gln Gln Arg Glu Val Tyr Val Lys Gly Leu Leu Ala Lys Ile Phe Glu
        35                  40                  45

Leu Glu Lys Lys Thr Glu Thr Ala Ala His Ser Leu Pro Gln Gln Thr
    50                  55                  60

Lys Lys Pro Glu Ser Glu Gly Tyr Leu Gln Glu Leu Gln Lys Cys
65                  70                  75                  80

<210> SEQ ID NO 24
<211> LENGTH: 18
<212> TYPE: PRT
<213> ORGANISM: Artificial Sequence
<220> FEATURE:
<223> OTHER INFORMATION: synthetic construct; ESCRT-recruiting element

<400> SEQUENCE: 24

Arg Lys Ser Pro Thr Pro Ser Ala Pro Val Pro Leu Thr Glu Pro Ala
1               5                   10                  15

Ala Gln

<210> SEQ ID NO 25
<211> LENGTH: 61
<212> TYPE: PRT
<213> ORGANISM: Artificial Sequence
<220> FEATURE:
<223> OTHER INFORMATION: synthetic construct; ESCRT-recruiting element
<220> FEATURE:
<221> NAME/KEY: misc
<222> LOCATION: (1)..(1)
<223> OTHER INFORMATION: Contains myristoylation motif

<400> SEQUENCE: 25

Ser Leu Tyr Pro Ser Leu Glu Asp Leu Lys Val Asp Lys Val Ile Gln
1               5                   10                  15

Ala Gln Thr Ala Phe Ser Ala Asn Pro Ala Asn Pro Ala Ile Leu Ser
            20                  25                  30

Glu Ala Ser Ala Pro Ile Pro His Asp Gly Asn Leu Tyr Pro Arg Leu
        35                  40                  45

Tyr Pro Glu Leu Ser Gln Tyr Met Gly Leu Ser Leu Asn
    50                  55                  60

<210> SEQ ID NO 26
<211> LENGTH: 32

```
<212> TYPE: RNA
<213> ORGANISM: Artificial Sequence
<220> FEATURE:
<223> OTHER INFORMATION: synthetic construct; lg70 RNA sequence

<400> SEQUENCE: 26
ggucugggcg cacuucggug acgguacagg cc                               32

<210> SEQ ID NO 27
<211> LENGTH: 21
<212> TYPE: RNA
<213> ORGANISM: Artificial Sequence
<220> FEATURE:
<223> OTHER INFORMATION: synthetic construct; ula RNA sequence

<400> SEQUENCE: 27
aauccauugc acuccggauu u                                          21

<210> SEQ ID NO 28
<211> LENGTH: 44
<212> TYPE: RNA
<213> ORGANISM: Artificial Sequence
<220> FEATURE:
<223> OTHER INFORMATION: synthetic construct; HIV_NC RNA sequence

<400> SEQUENCE: 28
ggcgacuggu gaguacgcca aaaauuuuga cuagcggagg cuag                  44

<210> SEQ ID NO 29
<211> LENGTH: 28
<212> TYPE: RNA
<213> ORGANISM: Artificial Sequence
<220> FEATURE:
<223> OTHER INFORMATION: synthetic construct; lmnb RNA sequence

<400> SEQUENCE: 29
ggcucgugua gcucauuagc uccgagcc                                    28

<210> SEQ ID NO 30
<211> LENGTH: 636
<212> TYPE: DNA
<213> ORGANISM: Artificial Sequence
<220> FEATURE:
<223> OTHER INFORMATION: synthetic construct; Flock House Virus
      defective interfering (DI)-RNA sequence

<400> SEQUENCE: 30
gtaaacaatt ccaagttcca aaatggttaa taacaacaga ccaagacgtc aacgagctca   60
acgcgttgtc gtcacaacaa cccaaacagc gcctgttcca cagcaaaacg tgccacgtaa  120
tggtagacgc cgacgtaatc gcacgaggcg taatcgccga cgtgtgcgcg gaatgaacat  180
ggcggcgcta accagattaa gtcaacctgg tttggcgttt ctcaaatgtg catttgcacc  240
acctgacttt cattcaggta cgcttccatg aacgtgggta tttacccaac gtcgaacttg  300
atgcagtttg ccggaagcat aactgtttgg aaatgccctg taaagctgag tactgtgcaa  360
ttcccggttg caacagatcc agccaccagt tcgctagttc atactcttgt tggtttagat  420
ggtgttctag cggtggggcc tgacaacttc tctgagtcat tcatgaagga tttggctttt  480
agaagcatcc ggacgccaac ctaaccgggc aagtatccga caatcggac atttggccac  540 aataagccca atttggttga agattaaagt agtgagcccc cttagcgcga aaccggaatt  600
tatattccaa accagtttaa gtcaacagac taaggt                           636
```

```
<210> SEQ ID NO 31
<211> LENGTH: 22
<212> TYPE: PRT
<213> ORGANISM: Artificial Sequence
<220> FEATURE:
<223> OTHER INFORMATION: synthetic construct; Ig70

<400> SEQUENCE: 31

Asp Arg Arg Arg Arg Gly Ser Arg Pro Ser Gly Ala Glu Arg Arg
1               5                   10                  15

Arg Arg Ala Ala Ala Ala
            20

<210> SEQ ID NO 32
<211> LENGTH: 97
<212> TYPE: PRT
<213> ORGANISM: Artificial Sequence
<220> FEATURE:
<223> OTHER INFORMATION: synthetic construct; ula

<400> SEQUENCE: 32

Ala Val Pro Glu Thr Arg Pro Asn His Thr Ile Tyr Ile Asn Asn Leu
1               5                   10                  15

Asn Glu Lys Ile Lys Lys Asp Glu Leu Lys Lys Ser Leu His Ala Ile
            20                  25                  30

Phe Ser Arg Phe Gly Gln Ile Leu Asp Ile Leu Val Ser Arg Ser Leu
        35                  40                  45

Lys Met Arg Gly Gln Ala Phe Val Ile Phe Lys Glu Val Ser Ser Ala
    50                  55                  60

Thr Asn Ala Leu Arg Ser Met Gln Gly Phe Pro Phe Tyr Asp Lys Pro
65                  70                  75                  80

Met Arg Ile Gln Tyr Ala Lys Thr Asp Ser Asp Ile Ile Ala Lys Met
                85                  90                  95

Lys

<210> SEQ ID NO 33
<211> LENGTH: 54
<212> TYPE: PRT
<213> ORGANISM: Artificial Sequence
<220> FEATURE:
<223> OTHER INFORMATION: synthetic construct; HIV NC
<220> FEATURE:
<221> NAME/KEY: misc
<222> LOCATION: (1)..(1)
<223> OTHER INFORMATION: Contains myristoylation motif

<400> SEQUENCE: 33

Gln Lys Gly Asn Phe Arg Asn Gln Arg Lys Thr Val Lys Cys Phe Asn
1               5                   10                  15

Cys Gly Lys Glu Gly His Ile Ala Lys Asn Cys Arg Ala Pro Arg Lys
            20                  25                  30

Lys Gly Cys Trp Lys Cys Gly Lys Glu Gly His Gln Met Lys Asp Cys
        35                  40                  45

Thr Glu Arg Gln Ala Asn
    50

<210> SEQ ID NO 34
<211> LENGTH: 14
<212> TYPE: PRT
<213> ORGANISM: Artificial Sequence
<220> FEATURE:
<223> OTHER INFORMATION: synthetic construct; mnb
```

-continued

<400> SEQUENCE: 34

Arg Pro Arg Gly Thr Arg Gly Lys Gly Arg Arg Ile Arg Arg
1               5                   10

<210> SEQ ID NO 35
<211> LENGTH: 31
<212> TYPE: PRT
<213> ORGANISM: Artificial Sequence
<220> FEATURE:
<223> OTHER INFORMATION: synthetic construct; FHV Alpha 1

<400> SEQUENCE: 35

Met Val Asn Asn Arg Pro Arg Arg Gln Arg Ala Gln Arg Val Val
1               5                   10                  15

Val Thr Thr Thr Gln Thr Ala Pro Val Pro Gln Gln Asn Val Pro
                20                  25                  30

<210> SEQ ID NO 36
<211> LENGTH: 1016
<212> TYPE: PRT
<213> ORGANISM: Artificial Sequence
<220> FEATURE:
<223> OTHER INFORMATION: synthetic construct; FHV protein A

<400> SEQUENCE: 36

Met Thr Leu Lys Val Ile Leu Gly Glu His Gln Ile Thr Arg Thr Glu
1               5                   10                  15

Leu Leu Val Gly Ile Ala Thr Val Ser Gly Cys Gly Ala Val Val Tyr
20 25 30

Cys Ile Ser Lys Phe Trp Gly Tyr Gly Ala Ile Ala Pro Tyr Pro Gln
35 40 45

Ser Gly Gly Asn Arg Val Thr Arg Ala Leu Gln Arg Ala Val Ile Asp
50 55 60

Lys Thr Lys Thr Pro Ile Glu Thr Arg Phe Tyr Pro Leu Asp Ser Leu
65 70 75 80

Arg Thr Val Thr Pro Lys Arg Val Ala Asp Asn Gly His Ala Val Ser
85 90 95

Gly Ala Val Arg Asp Ala Ala Arg Arg Leu Ile Asp Glu Ser Ile Thr
100 105 110

Ala Val Gly Gly Ser Lys Phe Glu Val Asn Pro Asn Pro Asn Ser Ser
115 120 125

Thr Gly Leu Arg Asn His Phe His Phe Ala Val Gly Asp Leu Ala Gln
130 135 140

Asp Phe Arg Asn Asp Thr Pro Ala Asp Asp Ala Phe Ile Val Gly Val
145 150 155 160

Asp Val Asp Tyr Tyr Val Thr Glu Pro Asp Val Leu Leu Glu His Met
165 170 175

Arg Pro Val Val Leu His Thr Phe Asn Pro Lys Lys Val Ser Gly Phe
180 185 190

Asp Ala Asp Ser Pro Phe Thr Ile Lys Asn Asn Leu Val Glu Tyr Lys
195 200 205

Val Ser Gly Gly Ala Ala Trp Val His Pro Val Trp Asp Trp Cys Glu
210 215 220

Ala Gly Glu Phe Ile Ala Ser Arg Val Arg Thr Ser Trp Lys Glu Trp
225 230 235 240

Phe Leu Gln Leu Pro Leu Arg Met Ile Gly Leu Glu Lys Val Gly Tyr
245 250 255

-continued

His Lys Ile His His Cys Arg Pro Trp Thr Asp Cys Pro Asp Arg Ala
            260                 265                 270

Leu Val Tyr Thr Ile Pro Gln Tyr Val Ile Trp Arg Phe Asn Trp Ile
            275                 280                 285

Asp Thr Glu Leu His Val Arg Lys Leu Lys Arg Ile Glu Tyr Gln Asp
290                 295                 300

Glu Thr Lys Pro Gly Trp Asn Arg Leu Glu Tyr Val Thr Asp Lys Asn
305                 310                 315                 320

Glu Leu Leu Val Ser Ile Gly Arg Glu Gly His Ala Gln Ile Thr
            325                 330                 335

Ile Glu Lys Glu Lys Leu Asp Met Leu Ser Gly Leu Ser Ala Thr Gln
            340                 345                 350

Ser Val Asn Ala Arg Leu Ile Gly Met Gly His Lys Asp Pro Gln Tyr
            355                 360                 365

Thr Ser Met Ile Val Gln Tyr Tyr Thr Gly Lys Lys Val Val Ser Pro
            370                 375                 380

Ile Ser Pro Thr Val Tyr Lys Pro Thr Met Pro Arg Val His Trp Pro
385                 390                 395                 400

Val Thr Ser Asp Ala Asp Val Pro Glu Val Ser Ala Arg Gln Tyr Thr
            405                 410                 415

Leu Pro Ile Val Ser Asp Cys Met Met Met Pro Met Ile Lys Arg Trp
            420                 425                 430

Glu Thr Met Ser Glu Ser Ile Glu Arg Arg Val Thr Phe Val Ala Asn
            435                 440                 445

Asp Lys Lys Pro Ser Asp Arg Ile Ala Lys Ile Ala Glu Thr Phe Val
450                 455                 460

Lys Leu Met Asn Gly Pro Phe Lys Asp Leu Asp Pro Leu Ser Ile Glu
465                 470                 475                 480

Glu Thr Ile Glu Arg Leu Asn Lys Pro Ser Gln Leu Gln Leu Arg
            485                 490                 495

Ala Val Phe Glu Met Ile Gly Val Lys Pro Arg Gln Leu Ile Glu Ser
            500                 505                 510

Phe Asn Lys Asn Glu Pro Gly Met Lys Ser Ser Arg Ile Ile Ser Gly
            515                 520                 525

Phe Pro Asp Ile Leu Phe Ile Leu Lys Val Ser Arg Tyr Thr Leu Ala
            530                 535                 540

Tyr Ser Asp Ile Val Leu His Ala Glu His Asn Glu His Trp Tyr Tyr
545                 550                 555                 560

Pro Gly Arg Asn Pro Thr Glu Ile Ala Asp Gly Val Cys Glu Phe Val
            565                 570                 575

Ser Asp Cys Asp Ala Glu Val Ile Glu Thr Asp Phe Ser Asn Leu Asp
            580                 585                 590

Gly Arg Val Ser Ser Trp Met Gln Arg Asn Ile Ala Gln Lys Ala Met
            595                 600                 605

Val Gln Ala Phe Arg Pro Glu Tyr Arg Asp Glu Ile Ile Ser Phe Met
            610                 615                 620

Asp Thr Ile Ile Asn Cys Pro Ala Lys Ala Lys Arg Phe Gly Phe Arg
625                 630                 635                 640

Tyr Glu Pro Gly Val Gly Val Lys Ser Gly Ser Pro Thr Thr Thr Pro
            645                 650                 655

His Asn Thr Gln Tyr Asn Gly Cys Val Glu Phe Thr Ala Leu Thr Phe
            660                 665                 670

Glu His Pro Asp Ala Glu Pro Glu Asp Leu Phe Arg Leu Ile Gly Pro

```
          675                 680                 685
Lys Cys Gly Asp Asp Gly Leu Ser Arg Ala Ile Ile Gln Lys Ser Ile
    690                 695                 700

Asn Arg Ala Ala Lys Cys Phe Gly Leu Glu Leu Lys Val Glu Arg Tyr
705                 710                 715                 720

Asn Pro Glu Ile Gly Leu Cys Phe Leu Ser Arg Val Phe Val Asp Pro
            725                 730                 735

Leu Ala Thr Thr Thr Thr Ile Gln Asp Pro Leu Arg Thr Leu Arg Lys
        740                 745                 750

Leu His Leu Thr Thr Arg Asp Pro Thr Ile Pro Leu Ala Asp Ala Ala
    755                 760                 765

Cys Asp Arg Val Glu Gly Tyr Leu Cys Thr Asp Ala Leu Thr Pro Leu
770                 775                 780

Ile Ser Asp Tyr Cys Lys Met Val Leu Arg Leu Tyr Gly Pro Thr Ala
785                 790                 795                 800

Ser Thr Glu Gln Val Arg Asn Gln Arg Ser Arg Asn Lys Glu Lys
            805                 810                 815

Pro Tyr Trp Leu Thr Cys Asp Gly Ser Trp Pro Gln His Pro Gln Asp
        820                 825                 830

Ala His Leu Met Lys Gln Val Leu Ile Lys Arg Thr Ala Ile Asp Glu
    835                 840                 845

Asp Gln Val Asp Ala Leu Ile Gly Arg Phe Ala Ala Met Lys Asp Val
850                 855                 860

Trp Glu Lys Ile Thr His Asp Ser Glu Glu Ser Ala Ala Ala Cys Thr
865                 870                 875                 880

Phe Asp Glu Asp Gly Val Ala Pro Asn Ser Val Asp Glu Ser Leu Pro
            885                 890                 895

Met Leu Asn Asp Ala Lys Gln Thr Arg Ala Asn Pro Gly Thr Ser Arg
        900                 905                 910

Pro His Ser Asn Gly Gly Ser Ser His Gly Asn Glu Leu Pro Arg
    915                 920                 925

Arg Thr Glu Gln Arg Ala Gln Gly Pro Arg Gln Pro Ala Arg Leu Pro
930                 935                 940

Lys Gln Gly Lys Thr Asn Gly Lys Ser Asp Gly Asn Ile Thr Ala Gly
945                 950                 955                 960

Glu Thr Gln Arg Gly Gly Ile Pro Arg Gly Lys Gly Pro Arg Gly Gly
            965                 970                 975

Lys Thr Asn Thr Arg Arg Thr Pro Pro Lys Ala Gly Ala Gln Pro Gln
        980                 985                 990

Pro Ser Asn Asn Arg Lys Leu Glu  Lys Leu Ala Ser Arg  Ser Glu Gln
    995                 1000                1005

Lys Leu  Ile Ser Glu Glu Asp  Leu
    1010                1015

<210> SEQ ID NO 37
<211> LENGTH: 510
<212> TYPE: PRT
<213> ORGANISM: Vesicular stomatitis virus

<400> SEQUENCE: 37

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30
```

-continued

Val Pro Ser Asn Tyr His Tyr Cys Pro Ser Ser Asp Leu Asn Trp
         35                  40                  45

His Asn Asp Leu Ile Gly Thr Ala Leu Gln Val Lys Met Pro Lys Ser
 50                  55                  60

His Lys Ala Ile Gln Ala Asp Gly Trp Met Cys His Ala Ser Lys Trp
 65                  70                  75                  80

Val Thr Thr Cys Asp Phe Arg Trp Tyr Gly Pro Lys Tyr Ile Thr His
                 85                  90                  95

Ser Ile Arg Ser Phe Thr Pro Ser Val Glu Gln Cys Lys Glu Ser Ile
             100                 105                 110

Glu Gln Thr Lys Gln Gly Thr Trp Leu Asn Pro Gly Phe Pro Pro Gln
             115                 120                 125

Ser Cys Gly Tyr Ala Trp Thr Asp Ala Glu Ala Val Ile Val Gln Val
130                 135                 140

Thr Pro His His Val Leu Val Asp Glu Tyr Thr Gly Glu Trp Val Asp
145                 150                 155                 160

Ser Gln Phe Ile Asn Gly Lys Cys Ser Asn Tyr Ile Cys Pro Thr Val
                165                 170                 175

His Asn Ser Thr Thr Trp His Ser Asp Tyr Lys Val Lys Gly Leu Cys
            180                 185                 190

Asp Ser Asn Leu Ile Ser Met Asp Ile Thr Phe Phe Ser Glu Asp Gly
            195                 200                 205

Glu Leu Ser Ser Leu Gly Lys Glu Gly Thr Gly Phe Arg Ser Asn Tyr
            210                 215                 220

Phe Ala Tyr Glu Thr Gly Gly Lys Ala Cys Lys Met Gln Tyr Cys Lys
225                 230                 235                 240

His Trp Gly Val Arg Leu Pro Ser Gly Val Trp Phe Glu Met Ala Asp
                245                 250                 255

Lys Asp Leu Phe Ala Ala Arg Phe Pro Glu Cys Pro Glu Gly Ser
            260                 265                 270

Ser Ile Ser Ala Pro Ser Gln Thr Ser Val Asp Val Ser Leu Ile Gln
            275                 280                 285

Asp Val Glu Arg Ile Leu Asp Tyr Ser Leu Cys Gln Glu Thr Trp Ser
            290                 295                 300

Lys Ile Arg Ala Gly Leu Pro Ile Ser Pro Val Asp Leu Ser Tyr Leu
305                 310                 315                 320

Ala Pro Lys Asn Pro Gly Thr Gly Pro Ala Phe Thr Ile Ile Asn Gly
            325                 330                 335

Thr Leu Lys Tyr Phe Glu Thr Arg Tyr Ile Arg Val Asp Ile Ala Ala
            340                 345                 350

Pro Ile Leu Ser Arg Met Val Gly Met Ile Ser Gly Thr Thr Thr Glu
            355                 360                 365

Arg Glu Leu Trp Asp Asp Trp Ala Pro Tyr Glu Asp Val Glu Ile Gly
            370                 375                 380

Pro Asn Gly Val Leu Arg Thr Ser Ser Gly Tyr Lys Phe Pro Leu Tyr
385                 390                 395                 400

Met Ile Gly His Gly Met Leu Asp Ser Asp Leu His Leu Ser Ser Lys
                405                 410                 415

Ala Gln Val Phe Glu His Pro His Ile Gln Asp Ala Ala Ser Gln Leu
            420                 425                 430

Pro Asp Asp Glu Ser Leu Phe Phe Gly Asp Thr Gly Leu Ser Lys Asn
            435                 440                 445

Pro Ile Glu Leu Val Glu Gly Trp Phe Ser Ser Trp Lys Ser Ser Ile

```
            450                 455                 460
Ala Ser Phe Phe Phe Ile Ile Gly Leu Ile Ile Gly Leu Phe Leu Val
465                 470                 475                 480

Leu Arg Val Gly Ile His Leu Cys Ile Lys Leu Lys His Thr Lys Lys
                485                 490                 495

Arg Gln Ile Tyr Thr Asp Ile Glu Met Asn Arg Leu Gly Lys
                500                 505                 510

<210> SEQ ID NO 38
<211> LENGTH: 665
<212> TYPE: PRT
<213> ORGANISM: Artificial Sequence
<220> FEATURE:
<223> OTHER INFORMATION: synthetic construct; MMLV

<400> SEQUENCE: 38

Met Ala Arg Ser Thr Leu Ser Lys Pro Leu Lys Asn Lys Val Asn Pro
1               5                   10                  15

Arg Gly Pro Leu Ile Pro Leu Ile Leu Met Leu Arg Gly Val Ser
            20                  25                  30

Thr Ala Ser Pro Gly Ser Ser Pro His Gln Val Tyr Asn Ile Thr Trp
        35                  40                  45

Glu Val Thr Asn Gly Asp Arg Glu Thr Val Trp Ala Thr Ser Gly Asn
    50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Pro Cys Cys Ser Gly Ser Ser Pro
            100                 105                 110

Gly Cys Ser Arg Asp Cys Glu Glu Pro Leu Thr Ser Leu Thr Pro Arg
        115                 120                 125

Cys Asn Thr Ala Trp Asn Arg Leu Lys Leu Asp Gln Thr Thr His Lys
    130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
        195                 200                 205

Cys Lys Asp Asn Lys Trp Cys Asn Pro Leu Val Ile Arg Phe Thr Asp
    210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255

Leu Arg Tyr Gln Asn Leu Gly Pro Arg Val Pro Ile Gly Pro Asn Pro
            260                 265                 270

Val Leu Ala Asp Gln Gln Pro Leu Ser Lys Pro Lys Pro Val Lys Ser
        275                 280                 285

Pro Ser Val Thr Lys Pro Pro Ser Gly Thr Pro Leu Ser Pro Thr Gln
    290                 295                 300

Leu Pro Pro Ala Gly Thr Glu Asn Arg Leu Leu Asn Leu Val Asp Gly
```

-continued

```
305                 310                 315                 320

Ala Tyr Gln Ala Leu Asn Leu Thr Ser Pro Asp Lys Thr Gln Glu Cys
                325                 330                 335

Trp Leu Cys Leu Val Ala Gly Pro Pro Tyr Tyr Glu Gly Val Ala Val
            340                 345                 350

Leu Gly Thr Tyr Ser Asn His Thr Ser Ala Pro Ala Asn Cys Ser Val
        355                 360                 365

Ala Ser Gln His Lys Leu Thr Leu Ser Glu Val Thr Gly Gln Gly Leu
    370                 375                 380

Cys Ile Gly Ala Val Pro Lys Thr His Gln Ala Leu Cys Asn Thr Thr
385                 390                 395                 400

Gln Thr Ser Ser Arg Gly Ser Tyr Tyr Leu Val Ala Pro Thr Gly Thr
                405                 410                 415

Met Trp Ala Cys Ser Thr Gly Leu Thr Pro Cys Ile Ser Thr Thr Ile
            420                 425                 430

Leu Asn Leu Thr Thr Asp Tyr Cys Val Leu Val Glu Leu Trp Pro Arg
        435                 440                 445

Val Thr Tyr His Ser Pro Ser Tyr Val Tyr Gly Leu Phe Glu Arg Ser
    450                 455                 460

Asn Arg His Lys Arg Glu Pro Val Ser Leu Thr Leu Ala Leu Leu Leu
465                 470                 475                 480

Gly Gly Leu Thr Met Gly Gly Ile Ala Ala Gly Ile Gly Thr Gly Thr
                485                 490                 495

Thr Ala Leu Met Ala Thr Gln Gln Phe Gln Gln Leu Gln Ala Ala Val
            500                 505                 510

Gln Asp Asp Leu Arg Glu Val Glu Lys Ser Ile Ser Asn Leu Glu Lys
        515                 520                 525

Ser Leu Thr Ser Leu Ser Glu Val Val Leu Gln Asn Arg Arg Gly Leu
    530                 535                 540

Asp Leu Leu Phe Leu Lys Glu Gly Gly Leu Cys Ala Ala Leu Lys Glu
545                 550                 555                 560

Glu Cys Cys Phe Tyr Ala Asp His Thr Gly Leu Val Arg Asp Ser Met
                565                 570                 575

Ala Lys Leu Arg Glu Arg Leu Asn Gln Arg Gln Lys Leu Phe Glu Ser
            580                 585                 590

Thr Gln Gly Trp Phe Glu Gly Leu Phe Asn Arg Ser Pro Trp Phe Thr
        595                 600                 605

Thr Leu Ile Ser Thr Ile Met Gly Pro Leu Ile Val Leu Leu Met Ile
    610                 615                 620

Leu Leu Phe Gly Pro Cys Ile Leu Asn Arg Leu Val Gln Phe Val Lys
625                 630                 635                 640

Asp Arg Ile Ser Val Val Gln Ala Leu Val Leu Thr Gln Gln Tyr His
                645                 650                 655

Gln Leu Lys Pro Ile Glu Tyr Glu Pro
            660                 665

<210> SEQ ID NO 39
<211> LENGTH: 654
<212> TYPE: PRT
<213> ORGANISM: Artificial Sequence
<220> FEATURE:
<223> OTHER INFORMATION: synthetic construct; AMLV envelope

<400> SEQUENCE: 39

Met Ala Arg Ser Thr Leu Ser Lys Pro Pro Gln Asp Lys Ile Asn Pro
```

-continued

```
1               5                   10                  15
Trp Lys Pro Leu Ile Val Met Gly Val Leu Gly Val Gly Met Ala
            20                  25                  30
Glu Ser Pro His Gln Val Phe Asn Val Thr Trp Arg Val Thr Asn Leu
            35                  40                  45
Met Thr Gly Arg Thr Ala Asn Ala Thr Ser Leu Leu Gly Thr Val Gln
50                      55                  60
Asp Ala Phe Pro Lys Leu Tyr Phe Asp Leu Cys Asp Leu Val Gly Glu
65                  70                  75                  80
Glu Trp Asp Pro Ser Asp Gln Glu Pro Tyr Val Gly Tyr Gly Cys Lys
                    85                  90                  95
Tyr Pro Ala Gly Arg Gln Arg Thr Arg Thr Phe Asp Phe Tyr Val Cys
                100                 105                 110
Pro Gly His Thr Val Lys Ser Gly Cys Gly Pro Gly Glu Gly Tyr
                115                 120                 125
Cys Gly Lys Trp Gly Cys Glu Thr Thr Gly Gln Ala Tyr Trp Lys Pro
            130                 135                 140
Thr Ser Ser Trp Asp Leu Ile Ser Leu Lys Arg Gly Asn Thr Pro Trp
145                 150                 155                 160
Asp Thr Gly Cys Ser Lys Val Ala Cys Gly Pro Cys Tyr Asp Leu Ser
                165                 170                 175
Lys Val Ser Asn Ser Phe Gln Gly Ala Thr Arg Gly Arg Cys Asn
                180                 185                 190
Pro Leu Val Leu Glu Phe Thr Asp Ala Gly Lys Lys Ala Asn Trp Asp
            195                 200                 205
Gly Pro Lys Ser Trp Gly Leu Arg Leu Tyr Arg Thr Gly Thr Asp Pro
            210                 215                 220
Ile Thr Met Phe Ser Leu Thr Arg Gln Val Leu Asn Val Gly Pro Arg
225                 230                 235                 240
Val Pro Ile Gly Pro Asn Pro Val Leu Pro Asp Gln Arg Leu Pro Ser
                245                 250                 255
Ser Pro Ile Glu Ile Val Pro Ala Pro Gln Pro Pro Ser Pro Leu Asn
                260                 265                 270
Thr Ser Tyr Pro Pro Ser Thr Thr Ser Thr Pro Ser Thr Ser Pro Thr
                275                 280                 285
Ser Pro Ser Val Pro Gln Pro Pro Gly Thr Gly Asp Arg Leu Leu
            290                 295                 300
Ala Leu Val Lys Gly Ala Tyr Gln Ala Leu Asn Leu Thr Asn Pro Asp
305                 310                 315                 320
Lys Thr Gln Glu Cys Trp Leu Cys Leu Val Ser Gly Pro Pro Tyr Tyr
                325                 330                 335
Glu Gly Val Ala Val Gly Thr Tyr Thr Asn His Ser Thr Ala Pro
                340                 345                 350
Ala Asn Cys Thr Ala Thr Ser Gln His Lys Leu Thr Leu Ser Glu Val
            355                 360                 365
Thr Gly Gln Gly Leu Cys Met Gly Ala Val Pro Lys Thr His Gln Ala
            370                 375                 380
Leu Cys Asn Thr Thr Gln Ser Ala Gly Ser Gly Ser Tyr Tyr Leu Ala
385                 390                 395                 400
Ala Pro Ala Gly Thr Met Trp Ala Cys Ser Thr Gly Leu Thr Pro Cys
                405                 410                 415
Leu Ser Thr Thr Val Leu Asn Leu Thr Thr Asp Tyr Cys Val Leu Val
            420                 425                 430
```

```
Glu Leu Trp Pro Arg Val Ile Tyr His Ser Pro Asp Tyr Met Tyr Gly
        435                 440                 445

Gln Leu Glu Gln Arg Thr Lys Tyr Lys Arg Glu Pro Val Ser Leu Thr
    450                 455                 460

Leu Ala Leu Leu Leu Gly Gly Leu Thr Met Gly Gly Ile Ala Ala Gly
465                 470                 475                 480

Ile Gly Thr Gly Thr Thr Ala Leu Ile Lys Thr Gln Gln Phe Glu Gln
                485                 490                 495

Leu His Ala Ala Ile Gln Thr Asp Leu Asn Glu Val Glu Lys Ser Ile
            500                 505                 510

Thr Asn Leu Glu Lys Ser Leu Thr Ser Leu Ser Glu Val Val Leu Gln
        515                 520                 525

Asn Arg Arg Gly Leu Asp Leu Leu Phe Leu Lys Glu Gly Gly Leu Cys
    530                 535                 540

Ala Ala Leu Lys Glu Glu Cys Cys Phe Tyr Ala Asp His Thr Gly Leu
545                 550                 555                 560

Val Arg Asp Ser Met Ala Lys Leu Arg Glu Arg Leu Asn Gln Arg Gln
                565                 570                 575

Lys Leu Phe Glu Thr Gly Gln Gly Trp Phe Glu Gly Leu Phe Asn Arg
            580                 585                 590

Ser Pro Trp Phe Thr Thr Leu Ile Ser Thr Ile Met Gly Pro Leu Ile
        595                 600                 605

Val Leu Leu Leu Ile Leu Leu Phe Gly Pro Cys Ile Leu Asn Arg Leu
    610                 615                 620

Val Gln Phe Val Lys Asp Arg Ile Ser Val Val Gln Ala Leu Val Leu
625                 630                 635                 640

Thr Gln Gln Tyr His Gln Leu Lys Pro Ile Glu Tyr Glu Pro
                645                 650

<210> SEQ ID NO 40
<211> LENGTH: 975
<212> TYPE: PRT
<213> ORGANISM: Artificial Sequence
<220> FEATURE:
<223> OTHER INFORMATION: synthetic construct; Sindbis virus

<400> SEQUENCE: 40

Ser Ala Ala Pro Leu Val Thr Ala Met Cys Leu Leu Gly Asn Val Ser
1               5                   10                  15

Phe Pro Cys Asp Arg Pro Pro Thr Cys Tyr Thr Arg Glu Pro Ser Arg
            20                  25                  30

Ala Leu Asp Ile Leu Glu Glu Asn Val Asn His Glu Ala Tyr Asp Thr
        35                  40                  45

Leu Leu Asn Ala Ile Leu Arg Cys Gly Ser Ser Gly Arg Ser Lys Arg
    50                  55                  60

Ser Val Ile Asp Asp Phe Thr Leu Thr Ser Pro Tyr Leu Gly Thr Cys
65                  70                  75                  80

Ser Tyr Cys His His Thr Val Pro Cys Phe Ser Pro Val Lys Ile Glu
                85                  90                  95

Gln Val Trp Asp Glu Ala Asp Asp Asn Thr Ile Arg Ile Gln Thr Ser
            100                 105                 110

Ala Gln Phe Gly Tyr Asp Gln Ser Gly Ala Ala Ser Ala Asn Lys Tyr
        115                 120                 125

Arg Tyr Met Ser Leu Lys Gln Asp His Thr Val Lys Glu Gly Thr Met
    130                 135                 140
```

-continued

```
Asp Asp Ile Lys Ile Ser Thr Ser Gly Pro Cys Arg Arg Leu Ser Tyr
145                 150                 155                 160

Lys Gly Tyr Phe Leu Leu Ala Lys Cys Pro Pro Gly Asp Ser Val Thr
                165                 170                 175

Val Ser Ile Val Ser Ser Asn Ser Ala Thr Ser Cys Thr Leu Ala Arg
            180                 185                 190

Lys Ile Lys Pro Lys Phe Val Gly Arg Glu Lys Tyr Asp Leu Pro Pro
        195                 200                 205

Val His Gly Lys Lys Ile Pro Cys Thr Val Tyr Asp Arg Leu Lys Glu
    210                 215                 220

Thr Thr Ala Gly Tyr Ile Thr Met His Arg Pro Arg Pro His Ala Tyr
225                 230                 235                 240

Thr Ser Tyr Leu Glu Glu Ser Ser Gly Lys Val Tyr Ala Lys Pro Pro
                245                 250                 255

Ser Gly Lys Asn Asn Tyr Glu Cys Lys Cys Gly Asp Tyr Lys Thr Gly
                260                 265                 270

Thr Val Ser Thr Arg Thr Glu Ile Thr Gly Cys Thr Ala Ile Lys Gln
            275                 280                 285

Cys Val Ala Tyr Lys Ser Asp Gln Thr Lys Trp Val Phe Asn Ser Pro
290                 295                 300

Asp Leu Ile Arg His Asp Asp His Thr Ala Gln Gly Lys Leu His Leu
305                 310                 315                 320

Pro Phe Lys Leu Ile Pro Ser Thr Cys Met Val Pro Val Ala His Ala
                325                 330                 335

Pro Asn Val Ile His Gly Phe Lys His Ile Ser Leu Gln Leu Asp Thr
                340                 345                 350

Asp His Leu Thr Leu Leu Thr Thr Arg Arg Leu Gly Ala Asn Pro Glu
            355                 360                 365

Pro Thr Thr Glu Trp Ile Val Gly Lys Trp Arg Asn Phe Trp Asp Arg
        370                 375                 380

Asp Gly Leu Glu Tyr Ile Trp Gly Asn His Glu Pro Val Arg Val Tyr
385                 390                 395                 400

Ala Gln Glu Ser Ala Pro Gly Asp Pro His Gly Trp Pro His Glu Ile
                405                 410                 415

Val Gln His Tyr Tyr His Arg His Pro Trp Thr Ile Leu Ala Val Ala
                420                 425                 430

Ser Ala Trp Ala Met Met Ile Gly Val Thr Val Ala Val Leu Cys Ala
            435                 440                 445

Cys Lys Ala Arg Arg Glu Cys Leu Thr Pro Tyr Ala Leu Ala Pro Asn
450                 455                 460

Ala Val Ile Pro Thr Ser Leu Ala Leu Leu Cys Cys Val Arg Ser Ala
465                 470                 475                 480

Asn Ala Glu Thr Phe Thr Glu Thr Met Ser Tyr Leu Trp Ser Asn Ser
                485                 490                 495

Gln Pro Phe Phe Trp Val Gln Leu Cys Ile Pro Leu Ala Ala Phe Ile
                500                 505                 510

Val Leu Met Arg Cys Cys Ser Cys Cys Leu Pro Phe Leu Val Val Ala
            515                 520                 525

Gly Ala Tyr Leu Ala Lys Val Asp Ala Tyr Glu His Ala Thr Trp Pro
            530                 535                 540

Asn Val Pro Gln Ile Pro Tyr Lys Ala Leu Val Glu Arg Ala Gly Tyr
545                 550                 555                 560
```

```
Ala Pro Leu Asn Leu Glu Ile Thr Val Met Ser Ser Glu Val Leu Pro
            565                 570                 575
Ser Thr Asn Gln Glu Tyr Ile Thr Cys Lys Phe Thr Val Val Pro
            580                 585                 590
Ser Pro Lys Ile Lys Cys Cys Gly Ser Leu Glu Cys Gln Pro Ala Ala
            595                 600                 605
His Ala Asp Tyr Thr Cys Lys Val Phe Gly Val Tyr Pro Phe Met
            610                 615                 620
Trp Gly Gly Ala Gln Cys Phe Cys Asp Ser Glu Asn Ser Gln Met Ser
625                 630                 635                 640
Glu Ala Tyr Val Glu Leu Ser Ala Asp Cys Ala Ser Asp His Ala Gln
                    645                 650                 655
Ala Ile Lys Val His Thr Ala Ala Met Lys Val Gly Leu Arg Ile Val
                    660                 665                 670
Tyr Gly Asn Thr Thr Ser Phe Leu Asp Val Tyr Val Asn Gly Val Thr
                    675                 680                 685
Pro Gly Thr Ser Lys Asp Leu Lys Val Ile Ala Gly Pro Ile Ser Ala
            690                 695                 700
Ser Phe Thr Pro Phe Asp His Lys Val Val Ile His Arg Gly Leu Val
705                 710                 715                 720
Tyr Asn Tyr Asp Phe Pro Glu Tyr Gly Ala Met Lys Pro Gly Ala Phe
                    725                 730                 735
Gly Asp Ile Gln Ala Thr Ser Leu Thr Ser Lys Asp Leu Ile Ala Ser
                    740                 745                 750
Thr Asp Ile Arg Leu Leu Lys Pro Ser Ala Lys Asn Val His Val Pro
                    755                 760                 765
Tyr Thr Gln Ala Ser Ser Gly Phe Glu Met Trp Lys Asn Asn Ser Gly
            770                 775                 780
Arg Pro Leu Gln Glu Thr Ala Pro Phe Gly Cys Lys Ile Ala Val Asn
785                 790                 795                 800
Pro Leu Arg Ala Val Asp Cys Ser Tyr Gly Asn Ile Pro Ile Ser Ile
                    805                 810                 815
Asp Ile Pro Asn Ala Ala Phe Ile Arg Thr Ser Asp Ala Pro Leu Val
                    820                 825                 830
Ser Thr Val Lys Cys Glu Val Ser Glu Cys Thr Tyr Ser Ala Asp Phe
            835                 840                 845
Gly Gly Met Ala Thr Leu Gln Tyr Val Ser Asp Arg Glu Gly Gln Cys
850                 855                 860
Pro Val His Ser His Ser Ser Thr Ala Thr Leu Gln Glu Ser Thr Val
865                 870                 875                 880
His Val Leu Glu Lys Gly Ala Val Thr Val His Phe Ser Thr Ala Ser
                    885                 890                 895
Pro Gln Ala Asn Phe Ile Val Ser Leu Cys Gly Lys Lys Thr Thr Cys
            900                 905                 910
Asn Ala Glu Cys Lys Pro Pro Ala Asp His Ile Val Ser Thr Pro His
            915                 920                 925
Lys Asn Asp Gln Glu Phe Gln Ala Ala Ile Ser Lys Thr Ser Trp Ser
            930                 935                 940
Trp Leu Phe Ala Leu Phe Gly Gly Ala Ser Ser Leu Leu Ile Ile Gly
945                 950                 955                 960
Leu Met Ile Phe Ala Cys Ser Met Met Leu Thr Ser Thr Arg Arg
                    965                 970                 975
```

-continued

```
<210> SEQ ID NO 41
<211> LENGTH: 675
<212> TYPE: PRT
<213> ORGANISM: Artificial Sequence
<220> FEATURE:
<223> OTHER INFORMATION: synthetic construct; Ebola
<220> FEATURE:
<221> NAME/KEY: misc_feature
<222> LOCATION: (484)..(484)
<223> OTHER INFORMATION: Xaa can be any naturally occurring amino acid
<220> FEATURE:
<221> NAME/KEY: misc_feature
<222> LOCATION: (499)..(499)
<223> OTHER INFORMATION: Xaa can be any naturally occurring amino acid

<400> SEQUENCE: 41

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335
```

Glu Asp His Lys Ile Met Ala Ser Glu Asn Ser Ser Ala Met Val Gln
                340                 345                 350

Val His Ser Gln Gly Arg Glu Ala Val Ser His Leu Thr Thr Leu
            355                 360                 365

Ala Thr Ile Ser Thr Ser Pro Gln Ser Leu Thr Thr Lys Pro Gly Pro
370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Ala Ala Gly Pro Pro Lys Ala
            420                 425                 430

Glu Asn Thr Asn Thr Ser Lys Ser Thr Asp Phe Leu Asp Pro Ala Thr
                435                 440                 445

Thr Thr Ser Pro Gln Asn His Ser Glu Thr Ala Gly Asn Asn Asn Thr
            450                 455                 460

His His Gln Asp Thr Gly Glu Glu Ser Ala Ser Ser Gly Lys Leu Gly
465                 470                 475                 480

Leu Ile Thr Xaa Ile Ala Gly Val Ala Gly Leu Ile Thr Gly Gly Arg
                485                 490                 495

Arg Thr Xaa Arg Glu Ala Ile Val Asn Ala Gln Pro Lys Cys Asn Pro
            500                 505                 510

Asn Leu His Tyr Trp Thr Thr Gln Asp Glu Gly Ala Ala Ile Gly Leu
                515                 520                 525

Ala Trp Ile Pro Tyr Phe Gly Pro Ala Ala Glu Gly Ile Tyr Ile Glu
            530                 535                 540

Gly Leu Met His Asn Gln Asp Gly Leu Ile Cys Gly Leu Arg Gln Leu
545                 550                 555                 560

Ala Asn Glu Thr Thr Gln Ala Leu Gln Leu Phe Leu Arg Ala Thr Thr
                565                 570                 575

Glu Leu Arg Thr Phe Ser Ile Leu Asn Arg Lys Ala Ile Asp Phe Leu
            580                 585                 590

Leu Gln Arg Trp Gly Gly Thr Cys His Ile Leu Gly Pro Asp Cys Cys
                595                 600                 605

Ile Glu Pro His Asp Trp Thr Lys Asn Ile Thr Asp Lys Ile Asp Gln
            610                 615                 620

Ile Ile His Asp Phe Val Asp Lys Thr Leu Pro Asp Gln Gly Asp Asn
625                 630                 635                 640

Asp Asn Trp Trp Thr Gly Trp Arg Gln Trp Ile Pro Ala Gly Ile Gly
                645                 650                 655

Val Thr Gly Val Ile Ile Ala Val Ile Ala Leu Phe Cys Ile Cys Lys
            660                 665                 670

Phe Val Phe
        675

<210> SEQ ID NO 42
<211> LENGTH: 1036
<212> TYPE: PRT
<213> ORGANISM: Artificial Sequence
<220> FEATURE:
<223> OTHER INFORMATION: synthetic construct; HIV
<220> FEATURE:
<221> NAME/KEY: misc_feature
<222> LOCATION: (139)..(140)
<223> OTHER INFORMATION: Xaa can be any naturally occurring amino acid

<400> SEQUENCE: 42

```
Met Arg Val Lys Glu Lys Tyr Gln His Leu Trp Arg Trp Gly Trp Lys
1               5                   10                  15

Trp Gly Ile Met Leu Leu Gly Ile Leu Met Ile Cys Ser Ala Thr Glu
            20                  25                  30

Asn Leu Trp Val Trp Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

Ile Ile Asn Val Cys Ala Thr His Ala Cys Val Pro Thr Asp Pro Asn
65                  70                  75                  80

Pro Gln Glu Val Ile Leu Val Asn Val Thr Glu Asn Phe Asp Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Asn
        115                 120                 125

Leu Lys Cys Thr Asp Leu Lys Asn Asp Thr Xaa Xaa Ser Asn Gly Arg
130                 135                 140

Met Ile Met Glu Lys Gly Glu Ile Lys Asn Cys Ser Phe Asn Ile Ser
145                 150                 155                 160

Thr Ser Ile Arg Asn Lys Val Gln Lys Glu Tyr Ala Phe Phe Tyr Lys
                165                 170                 175

Leu Asp Ile Arg Pro Ile Asp Asn Thr Thr Tyr Arg Leu Ile Ser Cys
            180                 185                 190

Asn Thr Ser Val Ile Thr Gln Ala Cys Pro Lys Val Ser Phe Glu Pro
        195                 200                 205

Ile Pro Ile His Tyr Cys Ala Pro Ala Gly Phe Ala Ile Leu Lys Cys
    210                 215                 220

Asn Asp Lys Thr Phe Asn Gly Thr Gly Pro Cys Thr Asn Val Ser Thr
225                 230                 235                 240

Val Gln Cys Thr His Gly Ile Arg Pro Val Val Ser Thr Gln Leu Leu
                245                 250                 255

Leu Asn Gly Ser Leu Ala Glu Glu Gly Val Ile Arg Ser Ala Asn
            260                 265                 270

Phe Thr Asp Asn Ala Lys Thr Ile Ile Val Gln Leu Asn Thr Ser Val
        275                 280                 285

Glu Ile Asn Cys Thr Arg Pro Asn Asn Asn Thr Arg Lys Ser Ile Arg
    290                 295                 300

Ile Gln Arg Gly Pro Gly Arg Ala Phe Val Thr Ile Gly Lys Ile Gly
305                 310                 315                 320

Asn Met Arg Gln Ala His Cys Asn Ile Ser Arg Ala Lys Trp Met Ser
                325                 330                 335

Thr Leu Lys Gln Ile Ala Ser Lys Leu Arg Glu Gln Phe Gly Asn Asn
            340                 345                 350

Lys Thr Val Ile Phe Lys Gln Ser Ser Gly Gly Asp Pro Glu Ile Val
        355                 360                 365

Thr His Ser Phe Asn Cys Gly Gly Glu Phe Phe Tyr Cys Asn Ser Thr
    370                 375                 380

Gln Leu Phe Asn Ser Thr Trp Phe Asn Ser Thr Trp Ser Thr Glu Gly
385                 390                 395                 400

Ser Asn Asn Thr Glu Gly Ser Asp Thr Ile Thr Leu Pro Cys Arg Ile
                405                 410                 415
```

```
Lys Gln Phe Ile Asn Met Trp Gln Glu Val Gly Lys Ala Met Tyr Ala
                420                 425                 430

Pro Pro Ile Ser Gly Gln Ile Arg Cys Ser Ser Asn Ile Thr Gly Leu
            435                 440                 445

Leu Leu Thr Arg Asp Gly Gly Lys Asn Thr Asn Glu Ser Glu Val Phe
        450                 455                 460

Arg Pro Gly Gly Gly Asp Met Arg Asp Asn Trp Arg Ser Glu Leu Tyr
465                 470                 475                 480

Lys Tyr Lys Val Val Lys Ile Glu Thr Leu Gly Val Ala Pro Thr Lys
                485                 490                 495

Ala Lys Arg Arg Val Val Gln Arg Glu Lys Arg Ala Val Gly Ile Gly
            500                 505                 510

Ala Leu Phe Leu Gly Phe Leu Gly Ala Ala Gly Ser Thr Met Gly Ala
        515                 520                 525

Ala Ser Met Thr Leu Thr Val Gln Ala Arg Gln Leu Leu Ser Gly Ile
    530                 535                 540

Val Gln Gln Gln Asn Asn Leu Leu Arg Ala Ile Glu Ala Gln Gln His
545                 550                 555                 560

Leu Leu Gln Leu Thr Val Trp Gly Ile Lys Gln Leu Gln Ala Arg Ile
                565                 570                 575

Leu Ala Val Glu Arg Tyr Leu Lys Asp Gln Gln Leu Leu Gly Ile Trp
            580                 585                 590

Gly Cys Ser Gly Lys Leu Ile Cys Thr Thr Ala Val Pro Trp Ala Ser
        595                 600                 605

Trp Ser Asn Lys Ser Leu Glu Gln Phe Trp Asn Asn Met Thr Trp Met
    610                 615                 620

Glu Trp Asp Arg Glu Ile Asn Asn Tyr Thr Ser Leu Ile His Ser Leu
625                 630                 635                 640

Ile Asp Glu Ser Gln Asn Gln Gln Glu Lys Asn Glu Gln Glu Leu Leu
                645                 650                 655

Glu Leu Asp Lys Trp Ala Ser Leu Trp Thr Thr Met Ile Thr Thr Leu
            660                 665                 670

Trp Ile Lys Ile Phe Ile Met Ile Val Gly Gly Leu Val Gly Leu Arg
        675                 680                 685

Ile Val Phe Ala Val Leu Ser Ile Val Asn Arg Val Arg Gln Gly Tyr
    690                 695                 700

Ser Pro Leu Ser Phe Gln Thr His Leu Pro Asn Arg Gly Pro Asp
705                 710                 715                 720

Arg Pro Glu Gly Ile Glu Glu Glu Gly Gly Glu Arg Asp Arg Asp Arg
                725                 730                 735

Ser Val Arg Leu Val Asn Gly Ser Leu Ala Leu Ile Trp Asp Asp Leu
            740                 745                 750

Arg Ser Leu Cys Leu Phe Ser Tyr His Arg Leu Arg Asp Leu Leu Leu
        755                 760                 765

Ile Val Thr Arg Ile Val Glu Leu Leu Gly Arg Arg Gly Trp Glu Ala
    770                 775                 780

Leu Lys Tyr Trp Trp Asn Leu Leu Gln Tyr Trp Ser Gln Glu Leu Lys
785                 790                 795                 800

Asn Ser Ala Val Ser Leu Leu Asn Ala Thr Ala Ile Ala Val Ala Glu
                805                 810                 815

Gly Thr Asp Arg Val Ile Glu Val Gln Gly Ala Tyr Arg Ala Ile
            820                 825                 830
```

```
Arg His Ile Pro Arg Arg Ile Arg Gln Gly Leu Glu Arg Ile Leu Asp
            835                 840                 845

Lys Trp Ala Ser Leu Trp Thr Thr Met Ile Thr Thr Leu Trp Ile Lys
850                 855                 860

Ile Phe Ile Met Ile Val Gly Leu Val Gly Leu Arg Ile Val Phe
865                 870                 875                 880

Ala Val Leu Ser Ile Val Asn Arg Val Arg Gln Gly Tyr Ser Pro Leu
                885                 890                 895

Ser Phe Gln Thr His Leu Pro Asn Arg Gly Gly Pro Asp Arg Pro Glu
                900                 905                 910

Gly Ile Glu Glu Glu Gly Gly Glu Arg Asp Arg Asp Arg Ser Val Arg
            915                 920                 925

Leu Val Asn Gly Ser Leu Ala Leu Ile Trp Asp Asp Leu Arg Ser Leu
    930                 935                 940

Cys Leu Phe Ser Tyr His Arg Leu Arg Asp Leu Leu Leu Ile Val Thr
945                 950                 955                 960

Arg Ile Val Glu Leu Leu Gly Arg Arg Gly Trp Glu Ala Leu Lys Tyr
                965                 970                 975

Trp Trp Asn Leu Leu Gln Tyr Trp Ser Gln Glu Leu Lys Asn Ser Ala
                980                 985                 990

Val Ser Leu Leu Asn Ala Thr Ala Ile Ala Val Ala Glu Gly Thr Asp
            995                 1000                1005

Arg Val Ile Glu Val Val Gln Gly Ala Tyr Arg Ala Ile Arg His
    1010                1015                1020

Ile Pro Arg Arg Ile Arg Gln Gly Leu Glu Arg Ile Leu
    1025                1030                1035

<210> SEQ ID NO 43
<211> LENGTH: 574
<212> TYPE: PRT
<213> ORGANISM: Artificial Sequence
<220> FEATURE:
<223> OTHER INFORMATION: synthetic construct; RSV
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid

<400> SEQUENCE: 43

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Xaa Arg Ala Arg Arg Glu Leu Pro Arg
                100                 105                 110

Phe Met Asn Tyr Thr Leu Asn Asn Ala Lys Lys Thr Asn Val Thr Leu
```

```
            115                 120                 125
Ser Lys Lys Arg Lys Arg Phe Leu Gly Phe Leu Leu Val Gly
130                 135                 140
Ser Ala Ile Ala Ser Gly Val Ala Val Ser Lys Val Leu His Leu Glu
145                 150                 155                 160
Gly Glu Val Asn Lys Ile Lys Ser Ala Leu Leu Ser Thr Asn Lys Ala
                    165                 170                 175
Val Val Ser Leu Ser Asn Gly Val Ser Val Leu Thr Ser Lys Val Leu
                180                 185                 190
Asp Leu Lys Asn Tyr Ile Asp Lys Gln Leu Leu Pro Ile Val Asn Lys
                195                 200                 205
Gln Ser Cys Ser Ile Ser Asn Ile Glu Thr Val Ile Glu Phe Gln Gln
210                 215                 220
Lys Asn Asn Arg Leu Leu Glu Ile Thr Arg Glu Phe Ser Val Asn Ala
225                 230                 235                 240
Gly Val Thr Thr Pro Val Ser Thr Tyr Met Leu Thr Xaa Glu Leu Leu
                245                 250                 255
Ser Leu Ile Asn Asp Met Pro Ile Thr Asn Asp Gln Lys Lys Leu Met
                260                 265                 270
Ser Asn Asn Val Gln Ile Val Arg Gln Gln Ser Tyr Ser Ile Met Ser
                275                 280                 285
Ile Ile Lys Glu Glu Val Leu Ala Tyr Val Val Gln Leu Pro Leu Tyr
                290                 295                 300
Gly Val Ile Asp Thr Pro Cys Trp Lys Leu His Thr Ser Pro Leu Cys
305                 310                 315                 320
Thr Thr Asn Thr Lys Glu Gly Ser Asn Ile Cys Leu Thr Arg Thr Asp
                    325                 330                 335
Arg Gly Trp Tyr Cys Asp Asn Ala Gly Ser Val Ser Phe Phe Pro Gln
                340                 345                 350
Ala Glu Thr Cys Lys Val Gln Ser Asn Arg Val Phe Cys Asp Thr Thr
                355                 360                 365
Val Ile Asn Ser Leu Thr Leu Pro Ser Glu Ile Asn Leu Cys Asn Val
370                 375                 380
Asp Ile Phe Asn Pro Lys Tyr Asp Cys Lys Ile Met Thr Ser Lys Thr
385                 390                 395                 400
Asp Val Ser Ser Ser Val Ile Thr Ser Leu Gly Ala Ile Val Ser Cys
                    405                 410                 415
Tyr Gly Lys Thr Lys Cys Thr Ala Ser Asn Lys Asn Arg Gly Ile Ile
                420                 425                 430
Lys Thr Phe Ser Asn Gly Cys Asp Tyr Val Ser Asn Lys Gly Met Asp
                435                 440                 445
Thr Val Ser Val Gly Asn Thr Leu Tyr Tyr Val Asn Lys Gln Glu Gly
                450                 455                 460
Lys Ser Leu Tyr Val Lys Gly Glu Pro Ile Ile Asn Phe Tyr Asp Pro
465                 470                 475                 480
Leu Val Phe Pro Ser Asp Glu Phe Asp Ala Ser Ile Ser Gln Val Asn
                    485                 490                 495
Glu Lys Ile Asn Gln Ser Leu Ala Phe Ile Arg Lys Ser Asp Glu Leu
                500                 505                 510
Leu His Asn Val Asn Ala Gly Lys Ser Thr Thr Asn Ile Met Ile Thr
                515                 520                 525
Thr Ile Ile Ile Val Ile Ile Val Ile Leu Leu Ser Leu Ile Ala Val
                530                 535                 540
```

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 44
<211> LENGTH: 1255
<212> TYPE: PRT
<213> ORGANISM: Artificial Sequence
<220> FEATURE:
<223> OTHER INFORMATION: synthetic construct; SARS

<400> SEQUENCE: 44

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

```
Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
            355                 360                 365

Val Ser Ala Thr Lys Leu Asn Asp Leu Cys Phe Ser Asn Val Tyr Ala
            370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
            435                 440                 445

Arg Pro Phe Glu Arg Asp Ile Ser Asn Val Pro Phe Ser Pro Asp Gly
            450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
            515                 520                 525

Phe Asn Gly Leu Thr Gly Thr Gly Val Leu Thr Pro Ser Ser Lys Arg
            530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
            595                 600                 605

Ala Ile His Ala Asp Gln Leu Thr Pro Ala Trp Arg Ile Tyr Ser Thr
            610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
            675                 680                 685

Tyr Ser Asn Asn Thr Ile Ala Ile Pro Thr Asn Phe Ser Ile Ser Ile
            690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750
```

```
Ala Ala Glu Gln Asp Arg Asn Thr Arg Glu Val Phe Ala Gln Val Lys
            755                 760                 765

Gln Met Tyr Lys Thr Pro Thr Leu Lys Tyr Phe Gly Gly Phe Asn Phe
770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
            885                 890                 895

Val Leu Tyr Glu Asn Gln Lys Gln Ile Ala Asn Gln Phe Asn Lys Ala
        900                 905                 910

Ile Ser Gln Ile Gln Glu Ser Leu Thr Thr Thr Ser Thr Ala Leu Gly
    915                 920                 925

Lys Leu Gln Asp Val Val Asn Gln Asn Ala Gln Ala Leu Asn Thr Leu
930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
            965                 970                 975

Arg Leu Ile Thr Gly Arg Leu Gln Ser Leu Gln Thr Tyr Val Thr Gln
        980                 985                 990

Gln Leu Ile Arg Ala Ala Glu Ile Arg Ala Ser Ala Asn Leu Ala Ala
    995                 1000                1005

Thr Lys Met Ser Glu Cys Val Leu Gly Gln Ser Lys Arg Val Asp
1010                1015                1020

Phe Cys Gly Lys Gly Tyr His Leu Met Ser Phe Pro Gln Ala Ala
1025                1030                1035

Pro His Gly Val Val Phe Leu His Val Thr Tyr Val Pro Ser Gln
1040                1045                1050

Glu Arg Asn Phe Thr Thr Ala Pro Ala Ile Cys His Glu Gly Lys
1055                1060                1065

Ala Tyr Phe Pro Arg Glu Gly Val Phe Val Phe Asn Gly Thr Ser
1070                1075                1080

Trp Phe Ile Thr Gln Arg Asn Phe Phe Ser Pro Gln Ile Ile Thr
1085                1090                1095

Thr Asp Asn Thr Phe Val Ser Gly Asn Cys Asp Val Val Ile Gly
1100                1105                1110

Ile Ile Asn Asn Thr Val Tyr Asp Pro Leu Gln Pro Glu Leu Asp
1115                1120                1125

Ser Phe Lys Glu Glu Leu Asp Lys Tyr Phe Lys Asn His Thr Ser
1130                1135                1140

Pro Asp Val Asp Leu Gly Asp Ile Ser Gly Ile Asn Ala Ser Val
1145                1150                1155

Val Asn Ile Gln Lys Glu Ile Asp Arg Leu Asn Glu Val Ala Lys
```

```
                1160                1165                1170
Asn Leu Asn Glu Ser Leu Ile Asp Leu Gln Leu Gly Lys Tyr
        1175                1180                1185
Glu Gln Tyr Ile Lys Trp Pro Trp Tyr Val Trp Leu Gly Phe Ile
    1190                1195                1200
Ala Gly Leu Ile Ala Ile Val Met Val Thr Ile Leu Leu Cys Cys
    1205                1210                1215
Met Thr Ser Cys Cys Ser Cys Leu Lys Gly Ala Cys Ser Cys Gly
    1220                1225                1230
Ser Cys Cys Lys Phe Asp Glu Asp Asp Ser Glu Pro Val Leu Lys
    1235                1240                1245
Gly Val Lys Leu His Tyr Thr
    1250                1255
```

<210> SEQ ID NO 45
<211> LENGTH: 565
<212> TYPE: PRT
<213> ORGANISM: Artificial Sequence
<220> FEATURE:
<223> OTHER INFORMATION: synthetic construct; Influenza

<400> SEQUENCE: 45

```
Met Lys Thr Ile Ile Ala Leu Ser Tyr Ile Phe Cys Leu Ala Leu Gly
1               5                   10                  15
Gln Asp Leu Pro Gly Asn Asp Asn Ser Thr Ala Thr Leu Cys Leu Gly
            20                  25                  30
His His Ala Val Pro Asn Gly Thr Leu Val Lys Thr Ile Thr Asp Asp
        35                  40                  45
Gln Ile Glu Val Thr Asn Ala Thr Glu Leu Val Gln Ser Ser Ser Thr
    50                  55                  60
Gly Lys Ile Cys Asn Asn Pro His Arg Ile Leu Asp Gly Ile Asp Cys
65                  70                  75                  80
Thr Leu Ile Asp Ala Leu Leu Gly Asp Pro His Cys Asp Val Phe Gln
                85                  90                  95
Asn Glu Thr Trp Asp Leu Phe Val Glu Arg Ser Lys Ala Phe Ser Asn
            100                 105                 110
Cys Tyr Pro Tyr Asp Val Pro Asp Tyr Ala Ser Leu Arg Ser Leu Val
        115                 120                 125
Ala Ser Ser Gly Thr Leu Glu Phe Ile Thr Glu Gly Phe Thr Trp Thr
    130                 135                 140
Gly Val Thr Gln Asn Gly Gly Ser Asn Ala Cys Lys Arg Gly Pro Gly
145                 150                 155                 160
Ser Gly Phe Phe Ser Arg Leu Asn Trp Leu Thr Lys Ser Gly Ser Thr
                165                 170                 175
Tyr Pro Val Leu Asn Val Thr Met Pro Asn Asn Asp Asn Phe Asp Lys
            180                 185                 190
Leu Tyr Ile Trp Gly Ile His His Pro Ser Thr Asn Gln Glu Gln Thr
        195                 200                 205
Ser Leu Tyr Val Gln Ala Ser Gly Arg Val Thr Val Ser Thr Arg Arg
    210                 215                 220
Ser Gln Gln Thr Ile Ile Pro Asn Ile Gly Ser Arg Pro Trp Val Arg
225                 230                 235                 240
Gly Leu Ser Ser Arg Ile Ser Ile Tyr Trp Thr Ile Val Lys Pro Gly
                245                 250                 255
Asp Val Leu Val Ile Asn Ser Asn Gly Asn Leu Ile Ala Pro Arg Gly
```

```
                260                 265                 270
Tyr Phe Lys Met Arg Thr Gly Lys Ser Ser Ile Met Arg Ser Asp Ala
                275                 280                 285

Pro Ile Asp Thr Cys Ile Ser Glu Cys Ile Thr Pro Asn Gly Ser Ile
            290                 295                 300

Pro Asn Asp Lys Pro Phe Gln Asn Val Asn Lys Asn Tyr Gly Ala Cys
305                 310                 315                 320

Pro Lys Tyr Val Lys Gln Asn Thr Leu Lys Leu Ala Thr Gly Met Arg
                325                 330                 335

Asn Val Pro Glu Lys Gln Thr Arg Gly Leu Phe Gly Ala Ile Ala Gly
            340                 345                 350

Phe Ile Glu Asn Gly Trp Glu Gly Met Ile Asp Gly Trp Tyr Gly Phe
                355                 360                 365

Arg His Gln Asn Ser Glu Gly Thr Gly Gln Ala Ala Asp Leu Lys Ser
            370                 375                 380

Thr Gln Ala Ala Ile Asp Gln Ile Asn Gly Lys Leu Asn Arg Val Ile
385                 390                 395                 400

Glu Lys Thr Asn Glu Lys Phe His Gln Ile Glu Lys Glu Phe Ser Glu
                405                 410                 415

Val Glu Gly Arg Ile Gln Asp Leu Glu Lys Tyr Val Glu Asp Thr Lys
            420                 425                 430

Ile Asp Leu Trp Ser Tyr Asn Ala Glu Leu Leu Val Ala Leu Glu Asn
                435                 440                 445

Gln His Thr Ile Asp Leu Thr Asp Ser Glu Met Asn Lys Leu Phe Glu
            450                 455                 460

Lys Thr Arg Arg Gln Leu Arg Glu Asn Ala Glu Glu Met Gly Asn Gly
465                 470                 475                 480

Cys Phe Lys Ile Tyr His Lys Cys Asp Asn Ala Cys Ile Glu Ser Ile
                485                 490                 495

Arg Asn Gly Thr Tyr Asp His Asp Val Tyr Arg Asp Glu Ala Leu Asn
            500                 505                 510

Asn Arg Phe Gln Ile Lys Gly Val Glu Leu Lys Ser Gly Tyr Lys Asp
                515                 520                 525

Trp Ile Leu Trp Ile Ser Phe Ala Ile Ser Cys Phe Leu Leu Cys Val
            530                 535                 540

Val Leu Leu Gly Phe Ile Met Trp Ala Cys Gln Arg Gly Asn Ile Arg
545                 550                 555                 560

Cys Asn Ile Cys Ile
                565

<210> SEQ ID NO 46
<211> LENGTH: 14
<212> TYPE: PRT
<213> ORGANISM: Artificial Sequence
<220> FEATURE:
<223> OTHER INFORMATION: ESCRT-recruiting element

<400> SEQUENCE: 46

Gln Ser Ile Lys Ala Phe Pro Ile Val Ile Asn Ser Asp Gly
1               5                   10

<210> SEQ ID NO 47
<211> LENGTH: 11
<212> TYPE: PRT
<213> ORGANISM: Artificial Sequence
<220> FEATURE:
<223> OTHER INFORMATION: ESCRT-recruiting element
```

```
<400> SEQUENCE: 47

Thr Ala Pro Ser Ser Pro Pro Tyr Glu Glu
1               5                   10

<210> SEQ ID NO 48
<211> LENGTH: 20
<212> TYPE: PRT
<213> ORGANISM: Artificial Sequence
<220> FEATURE:
<223> OTHER INFORMATION: synthetic construct; ESCRT-recruiting element

<400> SEQUENCE: 48

Ala Ala Pro Thr Ala Pro Pro Thr Gly Ala Ala Asp Ser Ile Pro Pro
1               5                   10                  15

Pro Tyr Ser Pro
            20

<210> SEQ ID NO 49
<211> LENGTH: 16
<212> TYPE: PRT
<213> ORGANISM: Artificial Sequence
<220> FEATURE:
<223> OTHER INFORMATION: synthetic construct; ESCRT-recruiting element

<400> SEQUENCE: 49

Asp Asp Leu Trp Leu Pro Pro Pro Glu Tyr Val Pro Leu Lys Glu Leu
1               5                   10                  15

<210> SEQ ID NO 50
<211> LENGTH: 21
<212> TYPE: PRT
<213> ORGANISM: Artificial Sequence
<220> FEATURE:
<223> OTHER INFORMATION: synthetic construct; ESCRT-recruiting element

<400> SEQUENCE: 50

Leu Gly Ile Ala Pro Pro Pro Tyr Glu Glu Asp Thr Ser Met Glu Tyr
1               5                   10                  15

Ala Pro Ser Ala Pro
            20

<210> SEQ ID NO 51
<211> LENGTH: 16
<212> TYPE: PRT
<213> ORGANISM: Artificial Sequence
<220> FEATURE:
<223> OTHER INFORMATION: synthetic construct; ESCRT-recruiting element

<400> SEQUENCE: 51

Asn Thr Tyr Met Gln Tyr Leu Asn Pro Pro Pro Tyr Ala Asp His Ser
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 52

Gly Cys Val Gln Cys Lys Asp Lys Glu Ala Thr Lys Leu Thr Glu
```

```
<210> SEQ ID NO 53
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 53

Gly Cys Ile Lys Ser Lys Arg Lys Asp Asn Leu Asn Asp Asp Glu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 54

Gly Cys Val Cys Ser Ser Asn Pro Glu Asp Asp Trp Met Glu Asn
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 55

Gly Cys Met Lys Ser Lys Phe Leu Gln Val Gly Gly Asn Thr Gly
1               5                   10                  15

<210> SEQ ID NO 56
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 56

Gly Cys Val Phe Cys Lys Lys Leu Glu Pro Val Ala Thr Ala Lys
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
```

```
<222> LOCATION: (1)..(1)
<223> OTHER INFORMATION: Contains myristoylation motif

<400> SEQUENCE: 57

Gly Cys Val His Cys Lys Glu Lys Ile Ser Gly Lys Gly Gln Gly
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 58

Gly Leu Leu Ser Ser Lys Arg Gln Val Ser Glu Lys Gly Lys Gly
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 59

Gly Gln Gln Pro Gly Lys Val Leu Gly Asp Gln Arg Arg Pro Ser
1               5                   10                  15

<210> SEQ ID NO 60
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 60

Gly Gln Gln Val Gly Arg Val Gly Glu Ala Pro Gly Leu Gln Gln
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 61

Gly Asn Ala Ala Ala Ala Lys Lys Gly Ser Glu Gln Glu Ser Val
1               5                   10                  15

<210> SEQ ID NO 62
<211> LENGTH: 15
```

```
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 62

Gly Asn Ala Ala Thr Ala Lys Lys Gly Ser Glu Val Glu Ser Val
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 63

Gly Ala Gln Leu Ser Leu Val Val Gln Ala Ser Pro Ser Ile Ala
1               5                   10                  15

<210> SEQ ID NO 64
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 64

Gly His Ala Leu Cys Val Cys Ser Arg Gly Thr Val Ile Ile Asp
1               5                   10                  15

<210> SEQ ID NO 65
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 65

Gly Gln Leu Cys Cys Phe Pro Phe Ser Arg Asp Glu Gly Lys Ile
1               5                   10                  15

<210> SEQ ID NO 66
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 66
```

Gly Asn Glu Ala Ser Tyr Pro Leu Glu Met Cys Ser His Phe Asp
1               5                   10                  15

<210> SEQ ID NO 67
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 67

Gly Asn Ser Gly Ser Lys Gln His Thr Lys His Asn Ser Lys Lys
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 68

Gly Cys Thr Leu Ser Ala Glu Asp Lys Ala Ala Val Glu Arg Ser
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 69

Gly Cys Thr Leu Ser Ala Glu Glu Arg Ala Ala Leu Glu Arg Ser
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 70

Gly Ala Gly Ala Ser Ala Glu Glu Lys His Ser Arg Glu Leu Glu
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: synthetic construct; motif
<220> FEATURE:

```
<221> NAME/KEY: misc
<222> LOCATION: (1)..(1)
<223> OTHER INFORMATION: Contains myristoylation motif

<400> SEQUENCE: 71

Gly Cys Arg Gln Ser Ser Glu Glu Lys Glu Ala Ala Arg Arg Ser
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 72

Gly Leu Ser Phe Thr Lys Leu Phe Ser Arg Leu Phe Ala Lys Lys
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 73

Gly Asn Ile Phe Gly Asn Leu Leu Lys Ser Leu Ile Gly Lys Lys
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 74

Gly Leu Thr Val Ser Ala Leu Phe Ser Arg Ile Phe Gly Lys Lys
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 75

Gly Lys Val Leu Ser Lys Ile Phe Gly Asn Lys Glu Met Arg Ile
1               5                   10                  15

<210> SEQ ID NO 76
```

```
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 76

Gly Asn Ser Lys Ser Gly Ala Leu Ser Lys Glu Ile Leu Glu Glu
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 77

Gly Lys Gln Asn Ser Lys Leu Arg Pro Glu Val Met Gln Asp Leu
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 78

Gly Lys Arg Ala Ser Lys Leu Lys Pro Glu Glu Val Glu Glu Leu
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 79

Gly Lys Gln Asn Ser Lys Leu Arg Pro Glu Val Leu Gln Asp Leu
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 80
```

```
Gly Ser Arg Ala Ser Thr Leu Leu Arg Asp Glu Glu Leu Glu Glu
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 81

Gly Ser Lys Leu Ser Lys Lys Lys Gly Tyr Asn Val Asn Asp
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 82

Gly Lys Gln Asn Ser Lys Leu Arg Pro Glu Met Leu Gln Asp Leu
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 83

Gly Asn Val Met Glu Gly Lys Ser Val Glu Glu Leu Ser Ser Thr
1               5                   10                  15

<210> SEQ ID NO 84
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 84

Gly Gln Gln Phe Ser Trp Glu Glu Ala Glu Glu Asn Gly Ala Val
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: synthetic construct; motif
```

```
<220> FEATURE:
<221> NAME/KEY: misc
<222> LOCATION: (1)..(1)
<223> OTHER INFORMATION: Contains myristoylation motif

<400> SEQUENCE: 85

Gly Asn Thr Lys Ser Gly Ala Leu Ser Lys Glu Ile Leu Glu Glu
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 86

Gly Lys Gln Asn Ser Lys Leu Arg Pro Glu Val Leu Gln Asp Leu
1               5                   10                  15

<210> SEQ ID NO 87
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 87

Gly Ala Gln Phe Ser Lys Thr Ala Ala Lys Gly Glu Ala Thr Ala
1               5                   10                  15

<210> SEQ ID NO 88
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 88

Gly Ser Gln Ser Ser Lys Ala Pro Arg Gly Asp Val Thr Ala Glu
1               5                   10                  15

<210> SEQ ID NO 89
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 89

Gly Asn Arg His Ala Lys Ala Ser Ser Pro Gln Gly Phe Asp Val
1               5                   10                  15
```

```
<210> SEQ ID NO 90
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: msic
<222> LOCATION: (1)..(1)
<223> OTHER INFORMATION: Contains myristoylation motif

<400> SEQUENCE: 90

Gly Gln Asp Gln Thr Lys Gln Gln Ile Glu Lys Gly Leu Gln Leu
1               5                   10                  15

<210> SEQ ID NO 91
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 91

Gly Gln Ala Leu Ser Ile Lys Ser Cys Asp Phe His Ala Ala Glu
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 92

Gly Asn Arg Ala Phe Lys Ala His Asn Gly His Tyr Leu Ser Ala
1               5                   10                  15

<210> SEQ ID NO 93
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 93

Gly Ala Arg Ala Ser Val Leu Ser Gly Gly Glu Leu Asp Arg Trp
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif
```

```
<400> SEQUENCE: 94

Gly Gln Thr Val Thr Thr Pro Leu Ser Leu Thr Leu Asp His Trp
1               5                   10                  15

<210> SEQ ID NO 95
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 95

Gly Gln Ala Val Thr Thr Pro Leu Ser Leu Thr Leu Asp His Trp
1               5                   10                  15

<210> SEQ ID NO 96
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 96

Gly Asn Ser Pro Ser Tyr Asn Pro Pro Ala Gly Ile Ser Pro Ser
1               5                   10                  15

<210> SEQ ID NO 97
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 97

Gly Gln Thr Leu Thr Thr Pro Leu Ser Leu Thr Leu Thr His Phe
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 98

Gly Gln Thr Ile Thr Thr Pro Leu Ser Leu Thr Leu Asp His Trp
1               5                   10                  15

<210> SEQ ID NO 99
<211> LENGTH: 15
<212> TYPE: PRT
<213> ORGANISM: Artificial Sequence
<220> FEATURE:
```

```
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 99

Gly Gln Thr Val Thr Thr Pro Leu Ser Leu Thr Leu Glu His Trp
1               5                   10                  15

<210> SEQ ID NO 100
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 100

Gly Gln Glu Leu Ser Gln His Glu Arg Tyr Val Glu Gln Leu Lys
1               5                   10                  15

<210> SEQ ID NO 101
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 101

Gly Val Ser Gly Ser Lys Gly Gln Lys Leu Phe Val Ser Val Leu
1               5                   10                  15

<210> SEQ ID NO 102
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misch
<222> LOCATION: (1)..(1)
<223> OTHER INFORMATION: Contains myristoylation motif

<400> SEQUENCE: 102

Gly Gly Lys Trp Ser Lys Ser Ser Val Val Gly Trp Pro Thr Val
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 103

Gly Gln His Pro Ala Lys Ser Met Asp Val Arg Arg Ile Glu Gly
1               5                   10                  15
```

```
<210> SEQ ID NO 104
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 104

Gly Ala Gln Val Ser Arg Gln Asn Val Gly Thr His Ser Thr Gln
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 105

Gly Leu Ala Phe Ser Gly Ala Arg Pro Cys Cys Cys Arg His Asn
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 106

Gly Asn Arg Gly Ser Ser Thr Ser Ser Arg Pro Pro Leu Ser Ser
1               5                   10                  15

<210> SEQ ID NO 107
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 107

Gly Ser Tyr Phe Val Pro Pro Ala Asn Tyr Phe Phe Lys Asp Ile
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif
```

```
<400> SEQUENCE: 108

Gly Ala Gln Leu Ser Thr Leu Ser Arg Val Val Leu Ser Pro Val
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 109

Gly Asn Leu Lys Ser Val Gly Gln Glu Pro Gly Pro Pro Cys Gly
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 110

Gly Ser Lys Arg Ser Val Pro Ser Arg His Arg Ser Leu Thr Thr
1               5                   10                  15

<210> SEQ ID NO 111
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 111

Gly Asn Gly Glu Ser Gln Leu Ser Ser Val Pro Ala Gln Lys Leu
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 112

Gly Ala His Leu Val Arg Arg Tyr Leu Gly Asp Ala Ser Val Glu
1               5                   10                  15

<210> SEQ ID NO 113
<211> LENGTH: 15
<212> TYPE: PRT
<213> ORGANISM: Artificial Sequence
```

-continued

```
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 113

Gly Gly Lys Leu Ser Lys Lys Lys Gly Tyr Asn Val Asn Asp
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 114

Gly Ser Cys Cys Ser Cys Pro Asp Lys Asp Thr Val Pro Asp Asn
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 115

Gly Ser Ser Glu Val Ser Ile Ile Pro Gly Leu Gln Lys Glu Glu
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 116

Leu Cys Cys Met Arg Arg Thr Lys Gln Val Glu Lys Asn Asp Glu
1               5                   10                  15

<210> SEQ ID NO 117
<211> LENGTH: 14
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 117

Gly Cys Leu Gly Asn Ser Lys Thr Glu Asp Gln Arg Asn Glu
1               5                   10
```

<210> SEQ ID NO 118
<211> LENGTH: 17
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 118

Thr Leu Glu Ser Ile Met Ala Cys Cys Leu Ser Glu Glu Ala Lys Glu
1               5                   10                  15

Ala

<210> SEQ ID NO 119
<211> LENGTH: 17
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 119

Ser Gly Val Val Arg Thr Leu Ser Arg Cys Leu Leu Pro Ala Glu Ala
1               5                   10                  15

Gly

<210> SEQ ID NO 120
<211> LENGTH: 18
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 120

Ala Asp Phe Leu Pro Ser Arg Ser Val Cys Phe Pro Gly Cys Val Leu
1               5                   10                  15

Thr Asn

<210> SEQ ID NO 121
<211> LENGTH: 20
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 121

Ala Arg Ser Leu Arg Trp Arg Cys Cys Pro Trp Cys Leu Thr Glu Asp
1               5                   10                  15

Glu Lys Ala Ala
            20

```
<210> SEQ ID NO 122
<211> LENGTH: 24
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 122

Leu Cys Cys Met Arg Arg Thr Lys Gln Val Glu Lys Asn Asp Asp
1               5                   10                  15

Gln Lys Ile Glu Gln Asp Gly Ile
            20

<210> SEQ ID NO 123
<211> LENGTH: 13
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 123

Gln Cys Cys Gly Leu Val His Arg Arg Arg Val Arg Val
1               5                   10

<210> SEQ ID NO 124
<211> LENGTH: 19
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 124

Asp Cys Leu Cys Ile Val Thr Thr Lys Lys Tyr Arg Tyr Gln Asp Glu
1               5                   10                  15

Asp Thr Pro

<210> SEQ ID NO 125
<211> LENGTH: 19
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 125

Cys Lys Gly Leu Ala Gly Leu Pro Ala Ser Cys Leu Arg Ser Ala Lys
1               5                   10                  15

Asp Met Lys

<210> SEQ ID NO 126
<211> LENGTH: 15
<212> TYPE: PRT
<213> ORGANISM: Artificial Sequence
```

```
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 126

Gly Cys Ile Lys Ser Lys Glu Asp Lys Gly Pro Ala Met Lys Tyr
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 127

Gly Cys Val Gln Cys Lys Asp Lys Glu Ala Thr Lys Leu Thr Glu
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 128

Gly Cys Ile Lys Ser Lys Arg Lys Asp Asn Leu Asn Asp Asp Glu
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 129

Gly Cys Val Cys Ser Ser Asn Pro Glu Asp Asp Trp Met Glu Asn
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 130

Gly Cys Met Lys Ser Lys Phe Leu Gln Val Gly Gly Asn Thr Gly
1               5                   10                  15
```

```
<210> SEQ ID NO 131
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 131

Gly Cys Val Phe Cys Lys Lys Leu Glu Pro Val Ala Thr Ala Lys
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 132

Gly Cys Val His Cys Lys Glu Lys Ile Ser Gly Lys Gly Gln Gly
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: msic
<222> LOCATION: (1)..(1)
<223> OTHER INFORMATION: Contains myristoylation motif

<400> SEQUENCE: 133

Gly Cys Thr Leu Ser Ala Glu Asp Lys Ala Ala Val Glu Arg Ser
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 134

Gly Cys Thr Leu Ser Ala Glu Glu Arg Ala Ala Leu Glu Arg Ser
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
```

<223> OTHER INFORMATION: Contains myristoylation motif

<400> SEQUENCE: 135

Gly Cys Arg Gln Ser Ser Glu Glu Lys Glu Ala Ala Arg Arg Ser
1               5                   10                  15

<210> SEQ ID NO 136
<211> LENGTH: 14
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 136

Gly Gln Leu Cys Cys Phe Pro Phe Ser Arg Asp Glu Gly Lys
1               5                   10

<210> SEQ ID NO 137
<211> LENGTH: 27
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 137

Gly Asn Leu Lys Ser Val Gly Gln Glu Pro Gly Pro Pro Cys Gly Leu
1               5                   10                  15

Gly Leu Gly Leu Gly Leu Gly Leu Cys Gly Lys
            20                  25

<210> SEQ ID NO 138
<211> LENGTH: 13
<212> TYPE: PRT
<213> ORGANISM: Artificial Sequence
<220> FEATURE:
<223> OTHER INFORMATION: synthetic construct; motif

<400> SEQUENCE: 138

Ser Gly Pro Gly Cys Met Ser Cys Lys Cys Val Leu Ser
1               5                   10

<210> SEQ ID NO 139
<211> LENGTH: 13
<212> TYPE: PRT
<213> ORGANISM: Artificial Sequence
<220> FEATURE:
<223> OTHER INFORMATION: synthetic construct; motif

<400> SEQUENCE: 139

Gly Thr Gln Gly Cys Met Gly Leu Pro Cys Val Val Met
1               5                   10

<210> SEQ ID NO 140
<211> LENGTH: 13
<212> TYPE: PRT
<213> ORGANISM: Artificial Sequence
<220> FEATURE:
<223> OTHER INFORMATION: synthetic construct; motif

<400> SEQUENCE: 140

```
Thr Pro Gly Cys Val Lys Ile Lys Cys Val Ile Met
1               5                   10

<210> SEQ ID NO 141
<211> LENGTH: 13
<212> TYPE: PRT
<213> ORGANISM: Artificial Sequence
<220> FEATURE:
<223> OTHER INFORMATION: synthetic construct; motif

<400> SEQUENCE: 141

Asp Met Lys Lys His Arg Cys Lys Cys Cys Ser Ile Met
1               5                   10

<210> SEQ ID NO 142
<211> LENGTH: 17
<212> TYPE: PRT
<213> ORGANISM: Artificial Sequence
<220> FEATURE:
<223> OTHER INFORMATION: synthetic construct; motif

<400> SEQUENCE: 142

Ser Lys Asp Gly Lys Lys Lys Lys Ser Lys Thr Lys Cys Val Ile
1               5                   10                  15

Met

<210> SEQ ID NO 143
<211> LENGTH: 14
<212> TYPE: PRT
<213> ORGANISM: Artificial Sequence
<220> FEATURE:
<223> OTHER INFORMATION: synthetic construct; motif

<400> SEQUENCE: 143

Lys Lys Lys Lys Lys Lys Ser Lys Thr Lys Cys Val Ile Met
1               5                   10

<210> SEQ ID NO 144
<211> LENGTH: 8
<212> TYPE: PRT
<213> ORGANISM: Artificial Sequence
<220> FEATURE:
<223> OTHER INFORMATION: synthetic construct; motif

<400> SEQUENCE: 144

Ser Lys Thr Lys Cys Val Ile Met
1               5

<210> SEQ ID NO 145
<211> LENGTH: 130
<212> TYPE: PRT
<213> ORGANISM: Artificial Sequence
<220> FEATURE:
<223> OTHER INFORMATION: synthetic construct; motif

<400> SEQUENCE: 145

His Gly Leu Gln Asp Asp Pro Asp Leu Gln Ala Leu Leu Lys Gly Ser
1               5                   10                  15

Gln Leu Leu Lys Val Lys Ser Ser Ser Trp Arg Arg Glu Arg Phe Tyr
                20                  25                  30

Lys Leu Gln Glu Asp Cys Lys Thr Ile Trp Gln Glu Ser Arg Lys Val
            35                  40                  45

Met Arg Ser Pro Glu Ser Gln Leu Phe Ser Ile Glu Asp Ile Gln Glu
        50                  55                  60
```

Val Arg Met Gly His Arg Thr Glu Gly Leu Glu Lys Phe Ala Arg Asp
65                  70                  75                  80

Ile Pro Glu Asp Arg Cys Phe Ser Ile Val Phe Lys Asp Gln Arg Asn
                85                  90                  95

Thr Leu Asp Leu Ile Ala Pro Ser Pro Ala Asp Ala Gln His Trp Val
            100                 105                 110

Gln Gly Leu Arg Lys Ile Ile His His Ser Gly Ser Met Asp Gln Arg
        115                 120                 125

Gln Lys
    130

<210> SEQ ID NO 146
<211> LENGTH: 139
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 146

Asp Ser Gly Arg Asp Phe Leu Thr Leu His Gly Leu Gln Asp Pro
1               5                   10                  15

Asp Leu Gln Ala Leu Leu Lys Gly Ser Gln Leu Leu Lys Val Lys Ser
            20                  25                  30

Ser Ser Trp Arg Arg Glu Arg Phe Tyr Lys Leu Gln Glu Asp Cys Lys
        35                  40                  45

Thr Ile Trp Gln Glu Ser Arg Lys Val Met Arg Ser Pro Glu Ser Gln
    50                  55                  60

Leu Phe Ser Ile Glu Asp Ile Gln Glu Val Arg Met Gly His Arg Thr
65                  70                  75                  80

Glu Gly Leu Glu Lys Phe Ala Arg Asp Ile Pro Glu Asp Arg Cys Phe
                85                  90                  95

Ser Ile Val Phe Lys Asp Gln Arg Asn Thr Leu Asp Leu Ile Ala Pro
            100                 105                 110

Ser Pro Ala Asp Ala Gln His Trp Val Gln Gly Leu Arg Lys Ile Ile
        115                 120                 125

His His Ser Gly Ser Met Asp Gln Arg Gln Lys
    130                 135

<210> SEQ ID NO 147
<211> LENGTH: 139
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 147

Asp Ser Gly Arg Asp Phe Leu Thr Leu His Gly Leu Gln Asp Pro
1               5                   10                  15

Asp Leu Gln Ala Leu Leu Lys Gly Ser Gln Leu Leu Lys Val Lys Ser
            20                  25                  30

Ser Ser Trp Arg Arg Glu Arg Phe Tyr Lys Leu Gln Glu Asp Cys Lys
        35                  40                  45

Thr Ile Trp Gln Glu Ser Arg Lys Val Met Arg Ser Pro Glu Ser Gln
                50                  55                  60

Leu Phe Ser Ile Glu Asp Ile Gln Glu Val Arg Met Gly His Arg Thr
 65                  70                  75                  80

Glu Gly Leu Glu Lys Phe Ala Arg Asp Ile Pro Glu Asp Arg Cys Phe
                    85                  90                  95

Ser Ile Val Phe Lys Asp Gln Arg Asn Thr Leu Asp Leu Ile Ala Pro
                100                 105                 110

Ser Pro Ala Asp Val Gln His Trp Val Gln Gly Leu Arg Lys Ile Ile
            115                 120                 125

Asp Arg Ser Gly Ser Met Asp Gln Arg Gln Lys
        130                 135

<210> SEQ ID NO 148
<211> LENGTH: 139
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 148

Asp Ser Gly Arg Asp Phe Leu Thr Leu His Gly Leu Gln Asp Asp Glu
 1               5                  10                  15

Asp Leu Gln Ala Leu Leu Lys Gly Ser Gln Leu Leu Lys Val Lys Ser
                20                  25                  30

Ser Ser Trp Arg Arg Glu Arg Phe Tyr Lys Leu Gln Glu Asp Cys Lys
            35                  40                  45

Thr Ile Trp Gln Glu Ser Arg Lys Val Met Arg Thr Pro Glu Ser Gln
 50                  55                  60

Leu Phe Ser Ile Glu Asp Ile Gln Glu Val Arg Met Gly His Arg Thr
 65                  70                  75                  80

Glu Gly Leu Glu Lys Phe Ala Arg Asp Val Pro Glu Asp Arg Cys Phe
                    85                  90                  95

Ser Ile Val Phe Lys Asp Gln Arg Asn Thr Leu Asp Leu Ile Ala Pro
                100                 105                 110

Ser Pro Ala Asp Ala Gln His Trp Val Leu Gly Leu His Lys Ile Ile
            115                 120                 125

His His Ser Gly Ser Met Asp Gln Arg Gln Lys
        130                 135

<210> SEQ ID NO 149
<211> LENGTH: 130
<212> TYPE: PRT
<213> ORGANISM: Artificial Sequence
<220> FEATURE:
<223> OTHER INFORMATION: synthetic construct; motif

<400> SEQUENCE: 149

His Gly Leu Gln Asp Asp Glu Asp Leu Gln Ala Leu Leu Lys Gly Ser
 1               5                  10                  15

Gln Leu Leu Lys Val Lys Ser Ser Trp Arg Arg Glu Arg Phe Tyr
                20                  25                  30

Lys Leu Gln Glu Asp Cys Lys Thr Ile Trp Gln Glu Ser Arg Lys Val
            35                  40                  45

```
Met Arg Thr Pro Glu Ser Gln Leu Phe Ser Ile Glu Asp Ile Gln Glu
     50                  55                  60

Val Arg Met Gly His Arg Thr Glu Gly Leu Glu Lys Phe Ala Arg Asp
 65                  70                  75                  80

Val Pro Glu Asp Arg Cys Phe Ser Ile Val Phe Lys Asp Gln Arg Asn
                 85                  90                  95

Thr Leu Asp Leu Ile Ala Pro Ser Pro Ala Asp Ala Gln His Trp Val
            100                 105                 110

Leu Gly Leu His Lys Ile Ile His Ser Gly Ser Met Asp Gln Arg
                115                 120                 125

Gln Lys
    130

<210> SEQ ID NO 150
<211> LENGTH: 177
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif

<400> SEQUENCE: 150

Ser Gly Gly Lys Tyr Val Asp Ser Glu Gly His Leu Tyr Thr Val Pro
 1               5                  10                  15

Ile Arg Glu Gln Gly Asn Ile Tyr Lys Pro Asn Asn Lys Ala Met Ala
                20                  25                  30

Glu Glu Met Asn Glu Lys Gln Val Tyr Asp Ala His Thr Lys Glu Ile
            35                  40                  45

Asp Leu Val Asn Arg Asp Pro Lys His Leu Asn Asp Val Val Lys
         50                  55                  60

Ile Asp Phe Glu Asp Val Ile Ala Glu Pro Glu Gly Thr His Ser Phe
 65                  70                  75                  80

Asp Gly Ile Trp Lys Ala Ser Phe Thr Thr Phe Thr Val Thr Lys Tyr
                 85                  90                  95

Trp Phe Tyr Arg Leu Leu Ser Ala Leu Phe Gly Ile Pro Met Ala Leu
                100                 105                 110

Ile Trp Gly Ile Tyr Phe Ala Ile Leu Ser Phe Leu His Ile Trp Ala
            115                 120                 125

Val Val Pro Cys Ile Lys Ser Phe Leu Ile Glu Ile Gln Cys Ile Ser
130                 135                 140

Arg Val Tyr Ser Ile Tyr Val His Thr Phe Cys Asp Pro Leu Phe Glu
145                 150                 155                 160

Ala Ile Gly Lys Ile Phe Ser Asn Ile Arg Ile Asn Thr Gln Lys Glu
                165                 170                 175

Ile

<210> SEQ ID NO 151
<211> LENGTH: 178
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (1)..(1)
<223> OTHER INFORMATION: Contains myristoylation motif
```

<400> SEQUENCE: 151

Ser Gly Gly Lys Tyr Val Asp Ser Glu Gly His Leu Tyr Thr Val Pro
1               5                   10                  15

Ile Arg Glu Gln Gly Asn Ile Tyr Lys Pro Asn Asn Lys Ala Met Ala
            20                  25                  30

Asp Glu Leu Ser Glu Lys Gln Val Tyr Asp Ala His Thr Lys Glu Ile
        35                  40                  45

Asp Leu Val Asn Arg Asp Pro Lys His Leu Asn Asp Asp Val Val Lys
    50                  55                  60

Ile Asp Phe Glu Asp Val Ile Ala Glu Pro Glu Gly Thr His Ser Phe
65                  70                  75                  80

Asp Gly Ile Trp Lys Ala Ser Phe Thr Thr Phe Thr Val Thr Lys Tyr
                85                  90                  95

Trp Phe Tyr Pro Val Leu Leu Ser Ala Leu Phe Gly Ile Pro Met Ala
                100                 105                 110

Leu Ile Trp Gly Ile Tyr Phe Ala Ile Leu Ser Phe Leu His Ile Trp
            115                 120                 125

Ala Val Val Pro Cys Ile Lys Ser Phe Leu Ile Glu Ile Gln Cys Ile
        130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile

<210> SEQ ID NO 152
<211> LENGTH: 4
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (2)..(2)
<223> OTHER INFORMATION: Xaa can be Thr or Ser

<400> SEQUENCE: 152

Pro Xaa Ala Pro
1

<210> SEQ ID NO 153
<211> LENGTH: 4
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (3)..(3)
<223> OTHER INFORMATION: Xaa can be any amino acid

<400> SEQUENCE: 153

Pro Pro Xaa Tyr
1

<210> SEQ ID NO 154
<211> LENGTH: 11
<212> TYPE: PRT
<213> ORGANISM: Artificial Sequence
<220> FEATURE:
<223> OTHER INFORMATION: synthetic construct; ESCRT-recruiting element

```
<400> SEQUENCE: 154

Thr Ala Ser Ala Pro Pro Pro Tyr Val Gly
1               5                   10

<210> SEQ ID NO 155
<211> LENGTH: 7
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (2)..(2)
<223> OTHER INFORMATION: Xaa can be Thr or Ser
<220> FEATURE:
<221> NAME/KEY: misc
<222> LOCATION: (6)..(6)
<223> OTHER INFORMATION: Xaa can be any amino acid

<400> SEQUENCE: 155

Pro Xaa Ala Pro Pro Xaa Tyr
1               5

<210> SEQ ID NO 156
<211> LENGTH: 8
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (2)..(2)
<223> OTHER INFORMATION: Xaa can be Thr or Ser
<220> FEATURE:
<221> NAME/KEY: misc_feature
<222> LOCATION: (7)..(7)
<223> OTHER INFORMATION: Xaa can be any naturally occurring amino acid

<400> SEQUENCE: 156

Pro Xaa Ala Pro Tyr Pro Xaa Leu
1               5

<210> SEQ ID NO 157
<211> LENGTH: 8
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (6)..(6)
<223> OTHER INFORMATION: Xaa can be Thr or Ser

<400> SEQUENCE: 157

Pro Pro Xaa Tyr Pro Xaa Ala Pro
1               5

<210> SEQ ID NO 158
<211> LENGTH: 8
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (3)..(3)
<223> OTHER INFORMATION: Xaa can be any amino acid
```

```
<220> FEATURE:
<221> NAME/KEY: misc
<222> LOCATION: (7)..(7)
<223> OTHER INFORMATION: Xaa can be any amino acid

<400> SEQUENCE: 158

Pro Pro Xaa Tyr Tyr Pro Xaa Leu
1               5

<210> SEQ ID NO 159
<211> LENGTH: 8
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (7)..(7)
<223> OTHER INFORMATION: Xaa can be any amino acid

<400> SEQUENCE: 159

Tyr Pro Xaa Leu Pro Pro Xaa Tyr
1               5

<210> SEQ ID NO 160
<211> LENGTH: 8
<212> TYPE: PRT
<213> ORGANISM: Artificial Sequence
<220> FEATURE:
<223> OTHER INFORMATION: synthetic construct; motif
<220> FEATURE:
<221> NAME/KEY: misc
<222> LOCATION: (3)..(3)
<223> OTHER INFORMATION: Xaa can be any amino acid
<220> FEATURE:
<221> NAME/KEY: misc
<222> LOCATION: (7)..(7)
<223> OTHER INFORMATION: Xaa can be any amino acid

<400> SEQUENCE: 160

Tyr Pro Xaa Leu Pro Pro Xaa Tyr
1               5

<210> SEQ ID NO 161
<211> LENGTH: 7
<212> TYPE: PRT
<213> ORGANISM: Artificial Sequence
<220> FEATURE:
<223> OTHER INFORMATION: synthetic construct; ESCRT-recruiting element

<400> SEQUENCE: 161

Pro Thr Ala Pro Pro Glu Glu
1               5

<210> SEQ ID NO 162
<211> LENGTH: 6
<212> TYPE: PRT
<213> ORGANISM: Artificial Sequence
<220> FEATURE:
<223> OTHER INFORMATION: synthetic construct; ESCRT-recruiting element

<400> SEQUENCE: 162

Tyr Pro Leu Thr Ser Leu
1               5
```

-continued

```
<210> SEQ ID NO 163
<211> LENGTH: 7
<212> TYPE: PRT
<213> ORGANISM: Artificial Sequence
<220> FEATURE:
<223> OTHER INFORMATION: synthetic construct; ESCRT-recruiting element

<400> SEQUENCE: 163

Pro Thr Ala Pro Pro Glu Tyr
1               5

<210> SEQ ID NO 164
<211> LENGTH: 4
<212> TYPE: PRT
<213> ORGANISM: Artificial Sequence
<220> FEATURE:
<223> OTHER INFORMATION: synthetic construct; ESCRT-recruiting element

<400> SEQUENCE: 164

Tyr Pro Asp Leu
1

<210> SEQ ID NO 165
<211> LENGTH: 4
<212> TYPE: PRT
<213> ORGANISM: Artificial Sequence
<220> FEATURE:
<223> OTHER INFORMATION: synthetic construct; ESCRT-recruiting element

<400> SEQUENCE: 165

Phe Pro Ile Val
1

<210> SEQ ID NO 166
<211> LENGTH: 7
<212> TYPE: PRT
<213> ORGANISM: Artificial Sequence
<220> FEATURE:
<223> OTHER INFORMATION: synthetic construct; ESCRT-recruiting element

<400> SEQUENCE: 166

Pro Thr Ala Pro Pro Glu Tyr
1               5

<210> SEQ ID NO 167
<211> LENGTH: 4
<212> TYPE: PRT
<213> ORGANISM: Artificial Sequence
<220> FEATURE:
<223> OTHER INFORMATION: synthetic construct; ESCRT-recruiting element

<400> SEQUENCE: 167

Pro Thr Ala Pro
1

<210> SEQ ID NO 168
<211> LENGTH: 4
<212> TYPE: PRT
<213> ORGANISM: Artificial Sequence
<220> FEATURE:
<223> OTHER INFORMATION: synthetic construct; ESCRT-recruiting element

<400> SEQUENCE: 168

Pro Pro Glu Tyr
1

<210> SEQ ID NO 169
```

```
<211> LENGTH: 6
<212> TYPE: PRT
<213> ORGANISM: Artificial Sequence
<220> FEATURE:
<223> OTHER INFORMATION: synthetic construct; ESCRT-recruiting element

<400> SEQUENCE: 169

Tyr Pro Leu Thr Ser Leu
1               5

<210> SEQ ID NO 170
<211> LENGTH: 16
<212> TYPE: PRT
<213> ORGANISM: Artificial Sequence
<220> FEATURE:
<223> OTHER INFORMATION: synthetic construct; ESCRT-recruiting element
<220> FEATURE:
<221> NAME/KEY: misc
<222> LOCATION: (1)..(1)
<223> OTHER INFORMATION: Contains myristoylation motif

<400> SEQUENCE: 170

Arg Arg Val Ile Leu Pro Thr Ala Pro Pro Glu Tyr Met Glu Ala Ile
1               5                   10                  15

<210> SEQ ID NO 171
<211> LENGTH: 15
<212> TYPE: PRT
<213> ORGANISM: Artificial Sequence
<220> FEATURE:
<223> OTHER INFORMATION: synthetic construct; ESCRT-recruiting element

<400> SEQUENCE: 171

Thr Pro Gln Thr Gln Asn Leu Tyr Pro Asp Leu Ser Glu Ile Lys
1               5                   10                  15

<210> SEQ ID NO 172
<211> LENGTH: 52
<212> TYPE: PRT
<213> ORGANISM: Artificial Sequence
<220> FEATURE:
<223> OTHER INFORMATION: synthetic construct; ESCRT-recruiting element

<400> SEQUENCE: 172

Leu Gln Ser Arg Pro Glu Pro Thr Ala Pro Pro Glu Glu Ser Phe Arg
1               5                   10                  15

Ser Gly Val Glu Thr Thr Thr Pro Pro Gln Lys Gln Glu Pro Ile Asp
            20                  25                  30

Lys Glu Leu Tyr Pro Leu Thr Ser Leu Arg Ser Leu Phe Gly Asn Asp
        35                  40                  45

Pro Ser Ser Gln
    50

<210> SEQ ID NO 173
<211> LENGTH: 20
<212> TYPE: PRT
<213> ORGANISM: Artificial Sequence
<220> FEATURE:
<223> OTHER INFORMATION: synthetic construct; ESCRT-recruiting element

<400> SEQUENCE: 173

Arg Arg Val Ile Leu Pro Thr Ala Pro Pro Glu Tyr Met Glu Ala Ile
1               5                   10                  15

Tyr Pro Val Arg
            20
```

<210> SEQ ID NO 174
<211> LENGTH: 51
<212> TYPE: PRT
<213> ORGANISM: Artificial Sequence
<220> FEATURE:
<223> OTHER INFORMATION: synthetic construct; ESCRT-recruiting element

<400> SEQUENCE: 174

Pro Ile Gln Gln Lys Ser Gln His Asn Lys Ser Val Val Gln Glu Thr
1               5                   10                  15

Pro Gln Thr Gln Asn Leu Tyr Pro Asp Leu Ser Glu Ile Lys Lys Glu
            20                  25                  30

Tyr Asn Val Lys Glu Lys Asp Gln Val Glu Asp Leu Asn Leu Asp Ser
        35                  40                  45

Leu Trp Glu
    50

<210> SEQ ID NO 175
<211> LENGTH: 20
<212> TYPE: PRT
<213> ORGANISM: Artificial Sequence
<220> FEATURE:
<223> OTHER INFORMATION: synthetic construct; ESCRT-recruiting element

<400> SEQUENCE: 175

Asn Pro Arg Gln Ser Ile Lys Ala Phe Pro Ile Val Ile Asn Ser Asp
1               5                   10                  15

Gly Gly Glu Lys
            20

<210> SEQ ID NO 176
<211> LENGTH: 10
<212> TYPE: PRT
<213> ORGANISM: Artificial Sequence
<220> FEATURE:
<223> OTHER INFORMATION: synthetic construct; ESCRT-recruiting element

<400> SEQUENCE: 176

Pro Thr Ala Pro Pro Glu Tyr Gly Gly Ser
1               5                   10

<210> SEQ ID NO 177
<211> LENGTH: 7
<212> TYPE: PRT
<213> ORGANISM: Artificial Sequence
<220> FEATURE:
<223> OTHER INFORMATION: synthetic construct; ESCRT-recruiting element

<400> SEQUENCE: 177

Pro Thr Ala Pro Gly Gly Ser
1               5

<210> SEQ ID NO 178
<211> LENGTH: 7
<212> TYPE: PRT
<213> ORGANISM: Artificial Sequence
<220> FEATURE:
<223> OTHER INFORMATION: synthetic construct; ESCRT-recruiting element

<400> SEQUENCE: 178

Pro Pro Glu Tyr Gly Gly Ser
1               5

<210> SEQ ID NO 179

```
<211> LENGTH: 9
<212> TYPE: PRT
<213> ORGANISM: Artificial Sequence
<220> FEATURE:
<223> OTHER INFORMATION: synthetic construct; ESCRT-recruiting element

<400> SEQUENCE: 179

Tyr Pro Leu Thr Ser Leu Gly Gly Ser
1               5

<210> SEQ ID NO 180
<211> LENGTH: 7
<212> TYPE: PRT
<213> ORGANISM: Artificial Sequence
<220> FEATURE:
<223> OTHER INFORMATION: synthetic construct; ESCRT-recruiting element

<400> SEQUENCE: 180

Tyr Pro Asp Leu Gly Gly Ser
1               5

<210> SEQ ID NO 181
<211> LENGTH: 7
<212> TYPE: PRT
<213> ORGANISM: Artificial Sequence
<220> FEATURE:
<223> OTHER INFORMATION: synthetic construct; ESCRT-recruiting element

<400> SEQUENCE: 181

Phe Pro Ile Val Gly Gly Ser
1               5

<210> SEQ ID NO 182
<211> LENGTH: 52
<212> TYPE: PRT
<213> ORGANISM: Artificial Sequence
<220> FEATURE:
<223> OTHER INFORMATION: synthetic construct; ESCRT-recruiting element

<400> SEQUENCE: 182

Leu Gln Ser Arg Pro Glu Ala Ala Ala Pro Glu Glu Ser Phe Arg
1               5                   10                  15

Ser Gly Val Glu Thr Thr Thr Pro Pro Gln Lys Gln Glu Pro Ile Asp
                20                  25                  30

Lys Glu Leu Tyr Pro Leu Thr Ser Leu Arg Ser Leu Phe Gly Asn Asp
            35                  40                  45

Pro Ser Ser Gln
        50

<210> SEQ ID NO 183
<211> LENGTH: 5
<212> TYPE: PRT
<213> ORGANISM: Artificial Sequence
<220> FEATURE:
<223> OTHER INFORMATION: synthetic construct; ESCRT-recruiting element

<400> SEQUENCE: 183

Ala Pro Thr Ala Pro
1               5

<210> SEQ ID NO 184
<211> LENGTH: 49
<212> TYPE: PRT
<213> ORGANISM: Artificial Sequence
<220> FEATURE:
<223> OTHER INFORMATION: synthetic construct; ESCRT-recruiting element
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid

<400> SEQUENCE: 184

Leu Xaa Arg Pro Glu Pro Thr Ala Pro Glu Glu Ser Phe Arg Ser
1               5                   10                  15

Gly Val Glu Thr Thr Thr Pro Pro Xaa Xaa Pro Ile Asp Lys Glu Leu
                20                  25                  30

Ala Ala Leu Thr Ser Leu Arg Ser Leu Phe Gly Asn Asp Pro Ser Ser
            35                  40                  45

Gln

<210> SEQ ID NO 185
<211> LENGTH: 19
<212> TYPE: PRT
<213> ORGANISM: Artificial Sequence
<220> FEATURE:
<223> OTHER INFORMATION: synthetic construct; ESCRT-recruiting element

<400> SEQUENCE: 185

Ser Arg Glu Lys Pro Tyr Lys Glu Val Thr Glu Asp Leu Leu His Leu
1               5                   10                  15

Asn Ser Leu

<210> SEQ ID NO 186
<211> LENGTH: 51
<212> TYPE: PRT
<213> ORGANISM: Artificial Sequence
<220> FEATURE:
<223> OTHER INFORMATION: synthetic construct; ESCRT-recruiting element

<400> SEQUENCE: 186

Gln Ser Arg Pro Glu Pro Thr Ala Pro Pro Glu Glu Ser Phe Arg Ser
1               5                   10                  15

Gly Val Glu Thr Thr Thr Pro Pro Gln Lys Gln Glu Pro Ile Asp Lys
                20                  25                  30

Glu Leu Tyr Pro Leu Thr Ser Leu Arg Ser Leu Phe Gly Asn Asp Pro
            35                  40                  45

Ser Ser Gln
    50

<210> SEQ ID NO 187
<211> LENGTH: 17
<212> TYPE: PRT
<213> ORGANISM: Artificial Sequence
<220> FEATURE:
<223> OTHER INFORMATION: synthetic construct; ESCRT-recruiting element

<400> SEQUENCE: 187

Asp Pro Gln Ile Pro Pro Pro Tyr Val Glu Pro Thr Ala Pro Gln
1               5                   10                  15

Val

<210> SEQ ID NO 188
<211> LENGTH: 11
<212> TYPE: PRT
<213> ORGANISM: Artificial Sequence
```

-continued

```
<220> FEATURE:
<223> OTHER INFORMATION: synthetic construct; ESCRT-recruiting element

<400> SEQUENCE: 188

Leu Leu Thr Glu Asp Pro Pro Pro Tyr Arg Asp
1               5                   10
```

ENGINEERING VIRUS-LIKE NANOCARRIERS FOR BIOMOLECULE DELIVERY

CROSS REFERENCE TO RELATED APPLICATIONS

This application claims the benefit of U.S. Application No. 62/751,457, filed on Oct. 26, 2018. The content of this earlier filed application is hereby incorporated by reference herein in its entirety.

STATEMENT REGARDING FEDERALLY SPONSORED RESEARCH

This invention was made with government support under grant no. GM082545 awarded by the National Institutes of Health. The government has certain rights in the invention.

REFERENCE TO SEQUENCE LISTING

The Sequence Listing submitted Jan. 22, 2020 as a text file named "21101_0379U2_Sequence_Listing.txt," created on Jan. 10, 2020, and having a size of 138,564 bytes is hereby incorporated by reference pursuant to 37 C.F.R. § 1.52(e)(5).

BACKGROUND

Viruses have traditionally been categorized as either "enveloped" or "non-enveloped", but in recent years this distinction has become blurred with the identification of "quasi-enveloped" viruses. In the conventional view, enveloped viruses contain single capsids surrounded by a membrane that they acquire, together with transmembrane envelope glycoproteins, as they bud from producer cells (FIG. 1A). These virus-encoded envelope glycoproteins are important for infection because they bind receptors and mediate the membrane fusion reactions for capsids to enter target cells (FIG. 1A). Envelope glycoproteins are also typically the major targets for neutralizing antibodies. In contrast, non-enveloped viruses were traditionally thought to exit producer cells only upon cell lysis (FIG. 1B). Unlike enveloped viruses, their capsids typically contain all of the elements required to bind receptors and enter target cells by disrupting their membrane (rather than via membrane fusion reactions). Recently, however, a subset of the viruses that were traditionally considered to be "non-enveloped" were found to be released from cells within membrane vesicles, often with multiple capsids within each vesicle (FIG. 1C). This newly described class of viruses are now referred to as "quasi-enveloped" viruses (FIG. 1C). Unlike classic enveloped viruses, quasi-enveloped virions retain the ability to enter cells through membrane disruption mechanisms (rather than membrane fusion), yet they also remain fully infectious when packaged inside vesicles. Current models hold that quasi-enveloped viruses are endocytosed by target cells, and their infectious internal capsids are then released when the vesicle begins to break down within the endosome. Once freed, the "naked" capsids retain their intrinsic ability to cross the endosomal membrane, and can thereby enter the cytoplasm and initiate infections. Importantly, quasi-enveloped viruses appear to have evolved advantages associated with both enveloped and non-enveloped viruses because they do not need viral fusion proteins to enter cells, yet their membrane coats protect the internal capsids from antibody recognition.

BRIEF SUMMARY

Disclosed herein are modified capsid proteins comprising a capsid forming protein, a membrane binding element and an ESCRT-recruiting element, wherein at least one of the membrane binding element and the ESCRT-recruiting element is heterologous to the capsid forming protein.

Disclosed herein are capsids comprising a plurality of the disclosed modified capsid proteins.

Disclosed herein are multimeric assemblies comprising a plurality of any one of the disclosed capsids within a membrane.

Disclosed herein are modified non-enveloped viruses comprising a capsid wherein the capsid comprises a plurality of modified capsid proteins, wherein the plurality of modified capsid proteins comprise a capsid forming protein, a membrane binding element and an ESCRT-recruiting element, wherein at least one of the membrane binding element and the ESCRT-recruiting element is heterologous to the modified capsid protein, wherein the capsid forming protein is a capsid forming protein of a non-enveloped virus.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1A shows enveloped viruses comprising a single cargo-containing capsid (orange) surrounded by membrane (green) derived from the host cell during budding. Embedded in the membrane are viral fusion proteins (red) that are required for entering target cells. FIG. 1B shows that non-enveloped viruses are released upon cell lysis and bind receptors directly with their capsid. Membrane-disrupting elements are released after endocytosis to enter the cytosol. FIG. 1C shows that quasi-enveloped viruses exit cells and acquire membrane by budding from producer cell. Often, multiple capsids are released inside single vesicles. Capsids are infectious with or without membranes.

FIG. 2A shows that Flock House Virus (FHV) and Nodamuravirus (NoV) capsid proteins Alpha serve as assembly domains. FIG. 2B shows that the membrane-binding PH domain from Phospholipase C (PLC) and ESCRT-recruiting p6$^{Gag}$ sequences were placed into surface loops of the proteins. FIG. 2C shows the resulting quasi-enveloped virus capsids.

FIG. 3A shows the structure of FHV and NoV capsids (left). Schematic of modified proteins: p6Gag and PH domains were placed in two different positions in the Alpha protein to generate enveloped versions of Alpha (termed eAlpha). A Myc tag was added to detect the proteins with antibodies. FIG. 3B Modified FHV Alpha proteins are released. eAlpha proteins that contain all functional domains for membrane binding, assembly and ESCRT recruitment are released (lanes 2-4, and 6-8) while controls are not (lanes 1 and 5). When eAlpha proteins are present, Alpha proteins are released, indicating that both proteins form an assembly (lines 2, 3, 6, and 7). FIG. 3C Modified NoV Alpha proteins are released. eAlpha proteins that contain all functional domains for membrane binding, assembly and ESCRT recruitment are released (lanes 2-4, 6-8,) while controls are not (lanes 1 and 5). When eAlpha proteins are present, Alpha proteins are released, indicating that both proteins form an assembly (lines 2, 3, 6, and 7).

FIG. 4A depicts the results of a protease protection assay that shows that eFHV and eNoV are released inside a membrane: Lane 1 shows the released protein, lane 2 shows the released protein is protected after trypsin digestion, and lane 3 shows that addition of Triton to strip away the membrane leads to degradation of the protein by Trypsin. FIG. 4B shows that the vesicle release is ESCRT-dependent because overexpression of a dominant negative VPS4 enzyme completely blocks the release of eFHV and eNoV (lanes 4 and 8).

FIG. 5A shows a model of the eFHV capsid with the FHV capsid protein in orange and the PH domain in blue. ESCRT binding sequences are unstructured and therefore not shown. FIG. 5B shows the icosahedral structure of the correct size (arrow) inside a vesicle membrane (arrowhead) shown by cryo-EM tomography.

FIG. 6A shows expression (lower panel) and release (upper panel) of eFHV, VSV-G, and GFP. Lane 1 shows the control, which was only transfected with GFP and VSV-G. Lane 2 shows expression of unmodified FHV Alpha together with eAlpha in a ratio 3:1 (note, Alpha is not detected on the western because it has no Myc-tag) together with GFP and VSV-G. Lane 3 shows expression of unmodified FHV Alpha together with eAlpha in a ratio 3:1 together with GFP and a mutant VSV-G that cannot mediate fusion with the target cell (P/D). Lane 4 shows expression of eAlpha together with GFP and VSV-G and lane 5 shows expression of eAlpha, GFP and mutant VSV-G. Note that in the presence of eAlpha, VSV-G and small amounts of GFP are also released into the supernatant. FIG. 6B shows delivery of GFP into target cells. eFHV can deliver GFP into target cells when co-expressed with VSV-G (lanes 2 and 4).

FIG. 7A shows the structure of AAV capsids (top left) and a model of capsids packaged into a vesicle (bottom left). Schematic of designing eAAV: AAV capsids consist of VP1, VP2, and VP3 proteins, which originate from different start codons in the AAV genome (right, top panel). By mutating these start codons, expression of VP2 can be uncoupled from VP1 and VP3 (right, center panel). The N terminus of VP2, which is not required for AAV assembly or infectivity, can now be modified with p6$^{Gag}$ and the 13 N-terminal residues of Lyn kinase that contain an N-terminal myristoylation and palmitoylation sequence. A Myc tag was added to detect the proteins with antibodies.

DETAILED DESCRIPTION

Figures 1A, 1B, 1C:
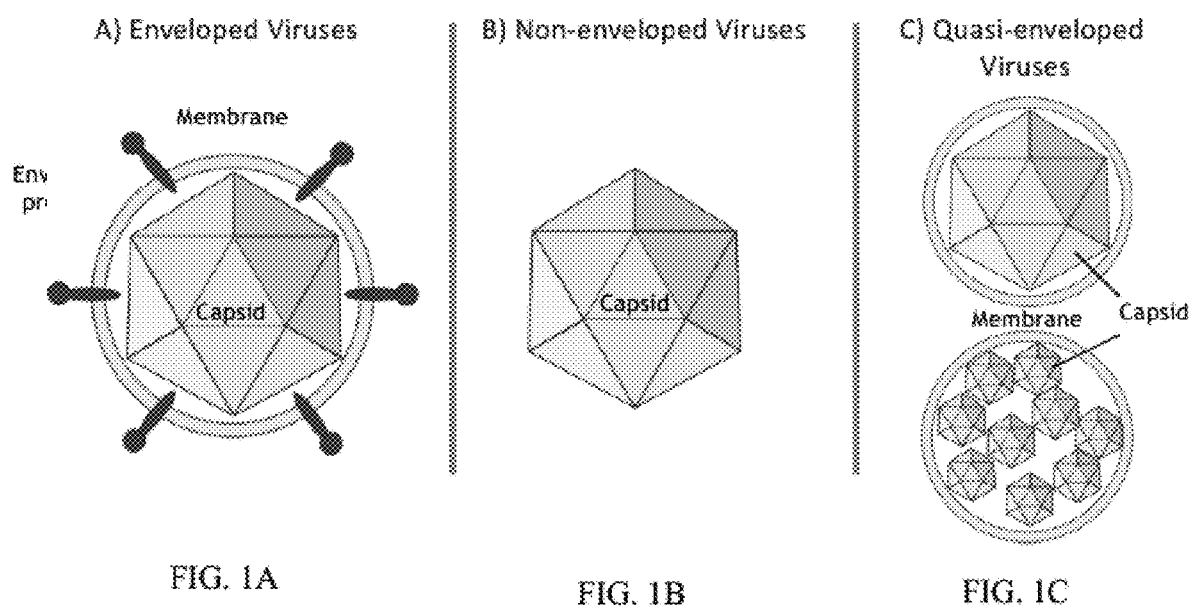
FIGS. 1A-C show enveloped, non-enveloped, and "quasi-enveloped" viruses.
Figures 2A, 2B, 2C:
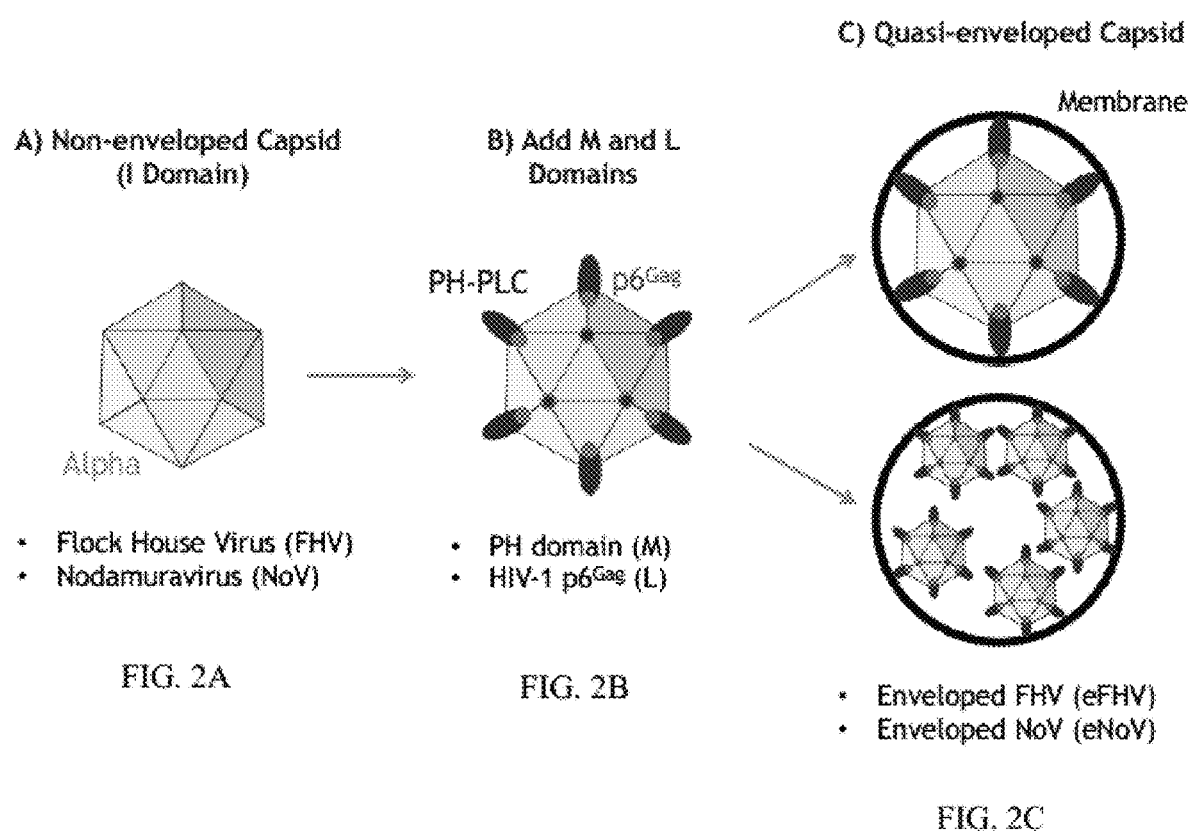
FIGS. 2A-C show the concept of enveloping non-enveloped virus capsids.
Figure 3A:
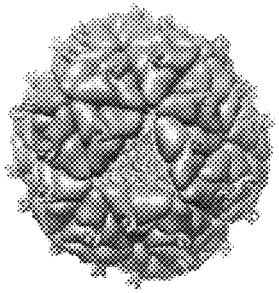
FIGS. 3A-C show the design of enveloped FHV (eFHV) and enveloped Nodamura virus NoV (eNoV).
Figure 3A:
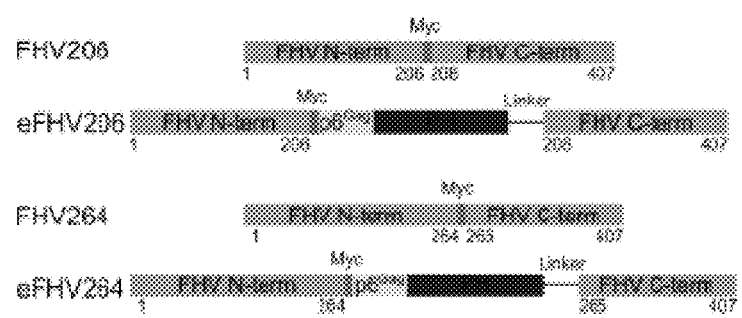
Figure 3A:
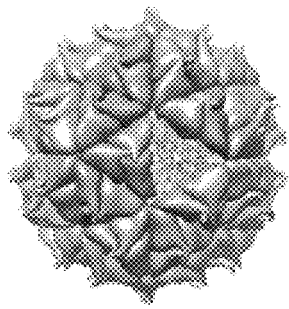
Figure 3A:
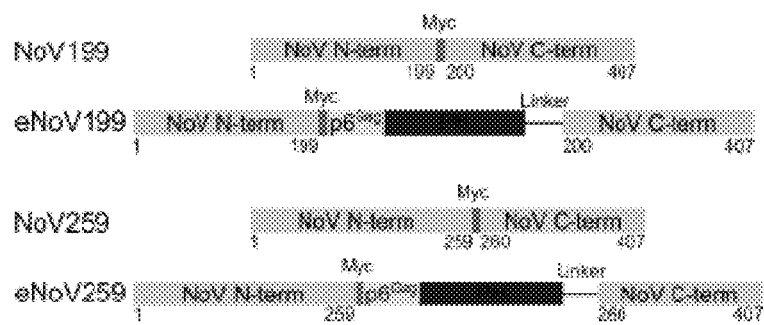
Figure 3B:
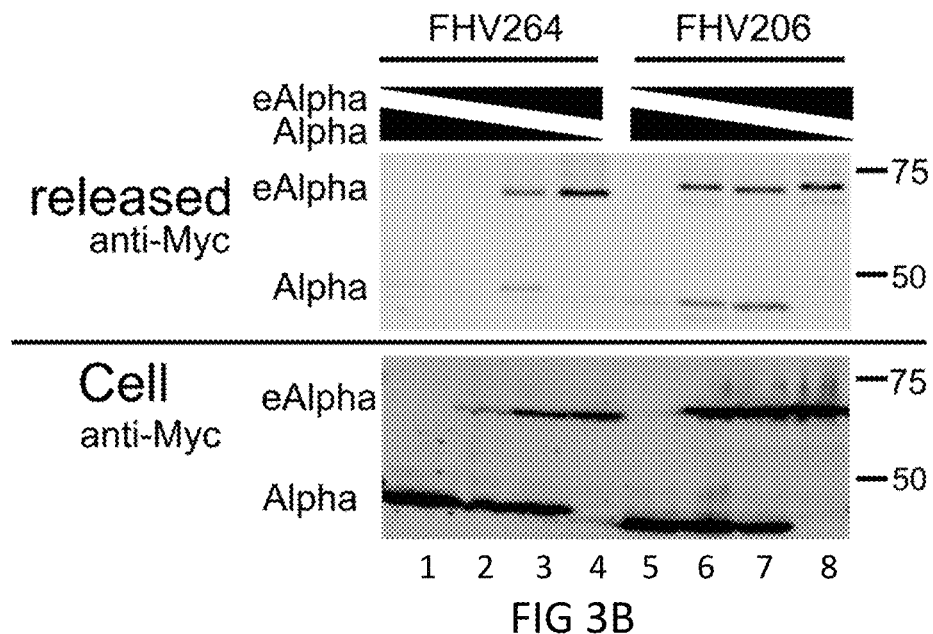
Figure 3C:
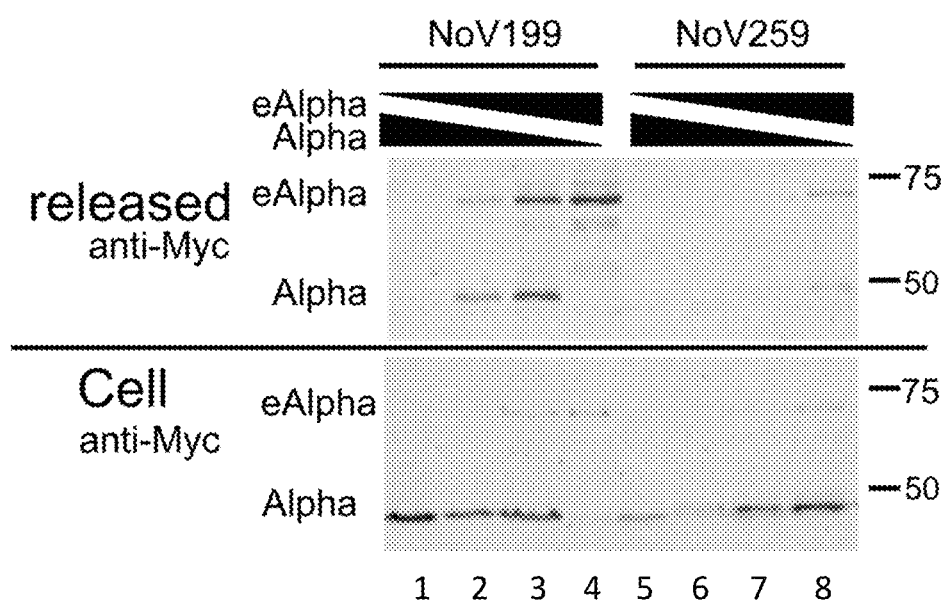

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a modified capsid protein" includes a plurality of such proteins, reference to "the modified capsid protein" is a reference to one or more modified capsid proteins and equivalents thereof known to those skilled in the art, and so forth.

A "capsid forming protein" is a structural protein which is part of the complex forming a capsid. As used herein, a "capsid forming protein" refers to an amino acid sequence capable of forming a capsid. For example, a capsid forming protein can be an amino acid sequence responsible for the self-interaction between capsid proteins. In some aspects, a capsid forming protein can be an alpha protein or VP2. For example, a capsid forming protein can be an FHV Alpha protein or AAV VP2 protein.

As used herein, "a capsid" is the protein shell of a virus. The capsid comprises one or more proteins referred to as capsid proteins or protomers. The capsid can enclose the viral genome or simply enclose nucleic acids, proteins, or small molecules for delivery. In some aspects, the capsid can have an icosahedral structure. In some aspects the capsid can be helical or prolate.

As used herein, "a capsid protein" is a protein that when assembled with other capsid proteins forms a capsid. A capsid protein can also be known as a capsid subunit or substructure because it is a smaller element of the capsid. In some aspects, a capsid protein is referred to as a protomer.

As used herein, "a modified capsid protein" is a capsid protein that is not naturally occurring or native to that particular capsid protein. A modified capsid protein can be a capsid protein with an amino acid substitution or an amino acid that has been altered from the amino acid sequence found in nature. A modified capsid protein can comprise sequences from other non-capsid proteins or from other non-heterologous capsid proteins. For example, a modified capsid protein can comprise a capsid forming protein, a membrane binding element and an ESCRT-recruiting element, wherein at least one of the membrane binding element and the ESCRT-recruiting element is heterologous to the capsid forming protein.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

The term "sequence of interest" or "gene of interest" can mean a nucleic acid sequence (e.g., a therapeutic gene), that is partly or entirely heterologous, i.e., foreign, to a cell into which it is introduced.

The term "sequence of interest" or "gene of interest" can also mean a nucleic acid sequence, that is partly or entirely complementary to an endogenous gene of the cell into which it is introduced. For example, the sequence of interest can be micro RNA (miRNA), short hairpin RNA (shRNA), or short interfering RNA (siRNA).

A "sequence of interest" or "gene of interest" can also include one or more transcriptional regulatory sequences and any other nucleic acid, such as introns, that may be necessary for optimal expression of a selected nucleic acid. A "protein of interest" means a peptide or polypeptide sequence (e.g., a therapeutic protein), that is expressed from a sequence of interest or gene of interest.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10"

is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

B. Modified Capsid Protein

Disclosed are modified capsid proteins comprising a capsid forming protein, a membrane binding element and an ESCRT-recruiting element, wherein at least one of the membrane binding element and the ESCRT-recruiting element is heterologous to the capsid forming protein.

In some aspects, the capsid forming protein can be a capsid forming protein of an enveloped virus. Examples of enveloped virus include but are not limited to Herpesviridae, Poxviridae, Coronaviridae, Retroviridae, Orthomyxoviridae and Hepadnaviridae. In some aspects, the capsid forming protein can be a capsid forming protein of a non-enveloped virus. Examples of non-enveloped virus include but are not limited to Adenoviridae, Polyomaviridae, Papillomaviridae, Rudiviridae, Clavaviridae, Parvoviridae, Birnaviridae, Reoviridae, Totiviridae, Picornavirideae, Comoviridae, Bromoviridae, Hepeviridae, and Nodaviridae.

In some aspects, the membrane binding element can be a membrane binding element of an enveloped virus. In some aspects, the ESCRT-recruiting element can be an ESCRT-recruiting element of an enveloped virus. In some aspects, the membrane binding element can be membrane binding element of a non-enveloped virus. In some aspects, the ESCRT-recruiting element can be an ESCRT-recruiting element of a non-enveloped virus.

In some aspects, the membrane binding element can be a non-viral membrane binding protein. For example, the membrane binding element can be a cellular membrane binding protein. In some aspects, the ESCRT-recruiting element can be a non-viral membrane binding protein. In some aspects, the membrane binding element can comprise an amino acid sequence derived from a viral or non-viral membrane binding protein sequence.

In some aspects, the membrane binding element can be the membrane binding PH element from phospholipase C. In some aspects, the ESCRT-recruiting element can be the $p6^{Gag}$ polypeptide from human immunodeficiency virus.

In some aspects, the membrane binding element and/or the ESCRT-recruiting element does not occur in any naturally occurring protein (i.e. is non-naturally occurring). In some aspects, the membrane binding element and/or the ESCRT-recruiting element are synthetic. For example, the membrane binding element and/or the ESCRT-recruiting element can comprise an amino acid sequence derived from a viral or non-viral membrane binding protein sequence.

In some aspects, the membrane binding element and the ESCRT-recruiting element can be a membrane binding element and an ESCRT-recruiting element of the same virus. In some aspects, the membrane binding element and the ESCRT-recruiting element can be a membrane binding element and an ESCRT-recruiting element of different viruses.

In some aspects, the membrane binding element and ESCRT-recruiting element can be located within any region of the modified capsid protein that allows the capsid protein to retain its function and do not inhibit assembly of a capsid. For example, in some aspects the membrane binding element and ESCRT-recruiting element can be located within at least one exposed surface loop of the modified capsid proteins. In some aspects, the membrane binding element and ESCRT-recruiting element can be located within the same exposed surface loop of the modified capsid protein. In some aspects, the membrane binding element and ESCRT-recruiting element can be located within different exposed surface loops of the modified capsid protein. In some aspects, the membrane-binding element and ESCRT-recruiting element can be located at either the N or C terminus of the modified capsid protein. In some aspects, the membrane-binding element can be located at either the N or C terminus of the modified capsid protein and the ESCRT-recruiting element can be located at the opposite terminus of the modified capsid protein from the membrane-binding element.

In some aspects, the disclosed modified capsid proteins can further comprise a desired cargo, sequence of interest, gene of interest, packaging moiety, or a targeting moiety.

1. Membrane Binding Element

The membrane binding element, also referred to as an "M domain," can be any suitable polypeptide that is capable of binding to a lipid bilayer via any suitable mechanism, including but not limited to non-covalently interacting with the lipid bilayer membrane. In some aspects, such interactions can include but are not limited to interacting via specific binding pockets with the polar head groups of lipid molecules in the lipid bilayer, interacting electrostatically with charged polar head groups, interacting non-covalently with the hydrophobic interior of the lipid bilayer, or by harboring a chemical modification (non-limiting examples can be fatty acid or acylation modifications such as myristoylation) that interacts non-covalently with the lipid bilayer. A given membrane binding element can employ one or more mechanisms of interaction with a lipid bilayer. As described herein, the multimeric assembly described herein can comprise one or more membrane binding elements. In some aspects, each modified capsid protein in a multimeric assembly comprises one or more membrane binding elements. In other aspects, some fraction (30%, 40%, 50%, 60%, 70%, 80%, 90%, or more) of the plurality of modified capsid proteins comprise one or more membrane binding elements. In some aspects, each capsid protein in the plurality of modified capsid proteins comprises one or more membrane binding elements. In some aspects, one or more membrane binding elements is required per multimeric assembly as described herein in order to drive association of the multimeric assembly with the lipid bilayer via any suitable mechanism.

The membrane binding elements present in a resulting modified capsid protein, capsid, multimeric assembly, or modified non-enveloped virus can all be the same, all different, or some the same and some different.

In various embodiments, the one or more membrane binding elements can comprise or consist of a polypeptide having an acylation motif, including but not limited to N-terminal myristoylation motifs (including but not limited to MGXXXT/S (SEQ ID NO: 1) motif and non-limiting example sequences below), palmitoylation motifs (including but not limited to non-limiting example sequences below), farnesylation motifs, and geranylgeranylation motifs (Resh M (1999) Fatty acylation of proteins: new insights into membrane targeting of myristoylated and palmitoylated proteins. Biochim. Biophys. Acta 1451: 1-16; Resh M (2013) Covalent lipid modifications of proteins. Curr. Biol. 23:R431-5); a polar headgroup-binding domain (including but not limited to non-limiting example sequences 100-106 in the attached appendices and the domains defined in: Stahelin R V (2009) Lipid binding domains: more than simple lipid effectors. J. Lipid Res. 50:S299-304); or transmembrane protein domains (the latter preferably when the multimeric assembly is enveloped by a lipid bilayer). In various further embodiments, the M domain may comprise envelope proteins of enveloped viruses, membrane protein transporters, membrane protein channels, B-cell receptors, T-cell receptors, transmembrane antigens of human pathogens, growth factors receptors, G-protein coupled receptors (GPCRs), or complement regulatory proteins including but not limited to CD55 and CD59.

In further embodiments, the membrane binding element may comprise or consist of one or more of the following peptides:

```
                                         (SEQ ID NO: 2)
(M)GARAS;
(Myr1; 6 N-terminal residues of HIV gag)

(SEQ ID NO: 3)
(M)GAQFS;
(Myr2; 6 N-terminal residues of MARCKS)

(SEQ ID NO: 4)
(M)GSSKS;
(Myr3; 6 N-terminal residues of Src)

(SEQ ID NO: 5)
(M)GKQNS;
(Myr4; 6 N-terminal residues of Neurocalcin)

(SEQ ID NO: 6)
(M)GCIKSKRKDNLN;
(Palm1; 13 N-terminal residues of Lyn kinase)

(SEQ ID NO: 7)
(M)GCTLSAEERAAL;
(Palm2; 13 N-terminal residues of Gao)

(SEQ ID NO: 8)
(M)LC CMRRTKQ VEK;
(Palm3; 13 N-terminal residues of GAP43)

(SEQ ID NO: 9)
(M)DCLCIVTTKKYR;
(Palm4; 13 N-terminal residues of PSD-95)

(SEQ ID NO: 10)
KKKKK SKTKC VIM;
(CaaX1; 13 C-terminal residues from K-Ras4B)

(SEQ ID NO: 11)
DMKKHRCKCCSIM;
(CaaX2; 13 C-terminal residues from paralemmin)

(SEQ ID NO: 12)
AQRQKKRRLCLLL;
(CaaX3; 13 C-terminal residues of RhoF)

(SEQ ID NO: 13)
AQEFIHQFLCNPL;
(CaaX4; 13 C-terminal residues of type II inositol
1,4,5-trisphosphate 5-phosphatase isoform X7)

(SEQ ID NO: 14)
HGLQDDPDLQALLKGSQLLKVKSSSWRRERFYKLQEDCKTIWQESRKVMR

SPESQLFSIEDIQEVRMGHRTEGLEKFARDIPEDRCFSIVFKDQRNTLDL

IAPSPADAQHWVQGLRKIIHHSGSMDQRQK;
(PH; Residues 11-40 of rat PLC5)

(SEQ ID NO: 15)
PHRFKVHNYMSPTFCDHCGSLLWGLVKQGLKCEDCGMNVHHKCREKVAN

LCG;
(CI; residues 246-297 of human PCK5 isoform X2)

(SEQ ID NO: 16)
GAVKLSVSYRNGTLFIMVMHIKDLVTEDGADPNPYVKTYLLPDTHKTSKR

KTKISRKTRNPTFNEMLVYSGYSKETLRQRELQLSVLSAESLRENFFLGG

ITLPLKDFNLSKETVKWYQLTAATYL;
(C2; residues 1384-1509 of mouse PI3K)
and/or (SEQ ID NO: 17)
AVAQQLRAESDFEQLPDDVAISANIADIEEKRGFTSHFVFVIEVKTKGGS

KYL IYRRYRQFH ALQ SKLEERF GPD SK S SAL AC TLPTLP

AK V Y VGVKQEI AEMRIPALN A Y MK SLLSLP VWVLMDED

VRIFF YQ SP YD SEQ VPQ ALRR
(PX; residues 2-149 of human p40phox)
```

Further exemplary membrane binding elements can comprise or consist of one or more of the peptides that follow (Resh M (1999) Biochim. Biophys. Acta 1451: 1-16; Resh M (2013) Curr. Biol. 23:R431-5; Stahelin RV (2009) J. Lipid Res. 50:S299-304).

In some aspects, the membrane binding element can comprise the membrane binding myristoylated and palmitoylated element of Lyn kinase.

i. N-Terminal Membrane Binding Elements

The following peptides can be at the N terminus of the polypeptide in which they appear in order to function as a membrane binding element.

Any amino acid sequence conforming to the consensus motif (M)GXXX(S/T) (SEQ ID NO: 1), where the membrane binding element is in the initiator methionine at the N terminus of the polypeptide sequence.

```
                                         (SEQ ID NO: 2)
        (M)GARAS (SEQ ID NO: 18)
        (M)GCIKSKGKDSLS (SEQ ID NO: 19)
        (M)GCINSKRKD (SEQ ID NO: 20)
        (M)GS SK SKPKDP SQRRR (SEQ ID NO: 21)
        (M)GCIKSKEDKGPAMKY (SEQ ID NO: 52)
        (M)GCVQCKDKEATKLTE (SEQ ID NO: 53)
        (M)GCIKSKRKDNLNDDE (SEQ ID NO: 54)
        (M)GCVCSSNPEDDWMEN (SEQ ID NO: 55)
        (M)GCMKSKFLQVGGNTG (SEQ ID NO: 56)
        (M)GCVFCKKLEPVATAK (SEQ ID NO: 57)
        (M)GCVHCKEKISGKGQG (SEQ ID NO: 58)
        (M)GLLSSKRQVSEKGKG (SEQ ID NO: 59)
        (M)GQQPGKVLGDQRRPS
```

-continued (M)GQQVGRVGEAPGLQQ (SEQ ID NO: 60)

(M)GNAAAAKKGSEQESV (SEQ ID NO: 61)

(M)GNAATAKKGSEVESV (SEQ ID NO: 62)

(M)GAQLSLVVQASPSIA (SEQ ID NO: 63)

(M)GHALCVCSRGTVIID (SEQ ID NO: 64)

(M)GQLCCFPF SRDEGKI (SEQ ID NO: 65)

(M)GNEASYPLEMCSHFD (SEQ ID NO: 66)

(M)GNSGSKQHTKHNSKK (SEQ ID NO: 67)

(M)GCTLSAEDKAAVERS (SEQ ID NO: 68)

(M)GCTLSAEERAALERS (SEQ ID NO: 69)

(M)GAGASAEEKHSRELE (SEQ ID NO: 70)

(M)GCRQSSEEKEAARRS (SEQ ID NO: 71)

(M)GLSFTKLFSRLFAKK (SEQ ID NO: 72)

(M)GNIFGNLLKSLIGKK (SEQ ID NO: 73)

(M)GLTVSALFSRIFGKK (SEQ ID NO: 74)

(M)GKVLSKIFGNKEMRI (SEQ ID NO: 75)

(M)GNSKSGALSKEILEE (SEQ ID NO: 76)

(M)GKQNSKLRPEVMQDL (SEQ ID NO: 77)

(M)GKRASKLKPEEVEEL (SEQ ID NO: 78)

(M)GKQNSKLRPEVLQDL (SEQ ID NO: 79)

(M)GSRASTLLRDEELEE (SEQ ID NO: 80)

(M)GSKLSKKKGYNVND (SEQ ID NO: 81)

(M)GKQNSKLRPEMLQDL (SEQ ID NO: 82)

(M)GNVMEGKSVEELSST (SEQ ID NO: 83)

(M)GQQF SWEEAEENGAV (SEQ ID NO: 84)

(M)GNTKSGALSKEILEE (SEQ ID NO: 85)

(M)GKQNSKLRPEVLQDL (SEQ ID NO: 86)

(M)GAQF SKTAAKGEATA (SEQ ID NO: 87)

(M)GSQSSKAPRGDVTAE (SEQ ID NO: 88)

(M)GNRHAK ASSPQGFDV (SEQ ID NO: 89)

(M)GQDQTKQQIEKGLQL (SEQ ID NO: 90)

(M)GQALSIKSCDFHAAE (SEQ ID NO: 91)

(M)GNRAFKAHNGHYLSA (SEQ ID NO: 92)

(M)GARASVLSGGELDRW (SEQ ID NO: 93)

(M)GQTVTTPLSLTLDHW (SEQ ID NO: 94)

(M)GQAVTTPL SLTLDHW (SEQ ID NO: 95)

(M)GNSPSYNPPAGISPS (SEQ ID NO: 96)

(M)GQTLTTPLSLTLTHF (SEQ ID NO: 97)

(M)GQTITTPL SLTLDHW (SEQ ID NO: 98)

(M)GQTVTTPLSLTLEHW (SEQ ID NO: 99)

(M)GQELSQHERYVEQLK (SEQ ID NO: 100)

(M)GVSGSKGQKLFVSVL (SEQ ID NO: 101)

(M)GGKWSKSSVVGWPTV (SEQ ID NO: 102)

(M)GQHPAKSMDVRRIEG (SEQ ID NO: 103)

(M)GAQVSRQNVGTHSTQ (SEQ ID NO: 104)

(M)GLAFSGARPCCCRHN (SEQ ID NO: 105)

(M)GNRGSSTSSRPPLSS (SEQ ID NO: 106)

(M)GSYFVPPANYFFKDI (SEQ ID NO: 107)

(M)GAQLSTLSRVVLSPV (SEQ ID NO: 108)

(M)GNLKSVGQEPGPPCG (SEQ ID NO: 109)

(M)GSKRSVPSRHRSLTT (SEQ ID NO: 110)

(M)GNGESQLSSVPAQKL (SEQ ID NO: 111)

(M)GAHLVRRYLGDASVE (SEQ ID NO: 112)

(M)GGKL SKKKKGYNVND (SEQ ID NO: 113)

(M)GSCCSCPDKDTVPDN (SEQ ID NO: 114)

(M)GS SEVSIIPGLQKEE (SEQ ID NO: 115)

(M)LCCMRRTKQ VEKNDE (SEQ ID NO: 116)

(M)GCLGNSKTEDQRNE (SEQ ID NO: 117)

(M)TLESIMACCLSEEAKEA (SEQ ID NO: 118)

(M)SGVVRTLSRCLLPAEAG (SEQ ID NO: 119)

(M)ADFLPSRSVCFPGCVLTN (SEQ ID NO: 120)

(M)ARSLRWRC CPWCLTEDEK AA (SEQ ID NO: 121)

(M)LCCMRRTKQVEKNDDDQKIEQDGI (SEQ ID NO: 122)

(M)QCCGLVHRRRVRV (SEQ ID NO: 123)

(M)DCLCIVTTKKYRYQDEDTP (SEQ ID NO: 124)

(M)CKGLAGLPASCLRSAKDMK (SEQ ID NO: 125)

(M)GCIKSKEDKGPAMKY (SEQ ID NO: 126)

(M)GCVQCKDKEATKLTE (SEQ ID NO: 127)

(M)GCIKSKRKDNLNDDE (SEQ ID NO: 128)

(M)GCVCSSNPEDDWMEN (SEQ ID NO: 129)

(M)GCMKSKFLQVGGNTG (SEQ ID NO: 130)

(M)GCVFCKKLEPVATAK (SEQ ID NO: 131)

(M)GCVHCKEKISGKGQG (SEQ ID NO: 132)

(M)GCTLSAEDKAAVERS (SEQ ID NO: 133)

(M)GCTLSAEERAALERS (SEQ ID NO: 134)

(M)GCRQ SSEEKEAARRS (SEQ ID NO: 135)

(M)GQLCCFPFSRDEGK (SEQ ID NO: 136)

(M)GNLKSVGQEPGPPCGLGLGLGLCGK (SEQ ID NO: 137)

ii. C-Terminal Membrane Binding Elements

The following peptides can be at the C terminus of the polypeptide which they appear in order to function as a membrane binding element.

SGPGCMSCKCVLS (SEQ ID NO: 138)

GTQGCMGLPCVVM (SEQ ID NO: 139)

TPGCVKIKKCVIM (SEQ ID NO: 140)

DMKKHRCKCCSIM (SEQ ID NO: 141)

SKDGKKKKK SKTKCVIM (SEQ ID NO: 142)

KKKKKKSKTKC (SEQ ID NO: 143)

SKTKCVIM (SEQ ID NO: 144)

iii. Polar Headgroup Binding Domains that Function as Membrane Binding Elements

The following peptides are non-limiting examples of polar headgroup-binding domains that can function as membrane binding elements. These domains can appear anywhere in the polypeptides of the invention consistent with proper folding and multimerization of the multimeric assembly.

(SEQ ID NO: 145)
HGLQDDPDLQALLKGSQLLKVKSSSWRRERFYKLQEDCKTIWQESRKVMR
SPESQLFSIEDIQEVRMGHRTEGLEKFARDIPEDRCFSIVFKDQRNTLDL
IAPSPADAQHWVQGLRKIIHHSGSMDQRQK (SEQ ID NO: 146)
(M)DSGRDFLTLHGLQDDPDLQALLKGSQLLKVKSSSWRRERF YKLQED
CKTIWQESRKVMRSPESQLF SIEDIQEVRMGHRTEGLEKF ARDIPEDR
CF SIVFKDQRNTLDLIAPSPADAQHWVQGLRKIIHHSGSMDQRQK (SEQ ID NO: 147)
(M)DSGRDFLTLHGLQDDPDLQALLKGSQLLKVKSSSWRRERF YKLQED
CKTIWQESRKVMRSPESQLF SIEDIQEVRMGHRTEGLEKF ARDIPEDR
CF SIVFKDQRNTLDLIAPSPADVQHWVQGLRKIIDRSGSMDQRQK (SEQ ID NO: 148)
(M)DSGRDFLTLHGLQDDEDLQ ALLKGSQLLKVKS SSWRRERFYKLQE
DCKTIWQESRKVMRTPESQLF SIEDIQEVRMGHRTEGLEKF ARDVPED
RCF SIVFKDQRNTLDLIAPSPADAQHWVLGLHKIIHHSGSMDQRQK (SEQ ID NO: 149)
HGLQDDEDLQ ALLKGSQLLKVKS SSWRRERF YKLQEDCKTIWQESRK
VMRTPESQLFSIEDIQEVRMGHRTEGLEKFARDVPEDRCFSIVFKDQRNT
LDLIAPSPADAQHWVLGLHKIIHHSGSMDQRQK (SEQ ID NO: 150)
(M)SGGKYVDSEGHLYTVPIREQGNIYKPNNK AMAEEMNEKQ VYD AH
TKEIDLVNRDPKHLNDDVVKIDFEDVIAEPEGTHSFDGIWKASFTTFTVT
KYWFYRLLSALFGIPMALIWGIYFAILSFLHIWAVVPCIKSFLIEIQCIS
RVYSIYVHTFCDPLFEAIGKIF SNIRINTQKEI (SEQ ID NO: 151)
(M)SGGKYVD SEGHLYTVPIREQGNIYKPNNKAMADELSEKQ VYDAHT
KEIDLVNRDPKHLNDDVVKIDFEDVIAEPEGTHSFDGIWKASFTTFTVTK

-continued

YWFYPvLLSALFGIPMALIWGIYFAILSFLHIWAVVPCIKSFLIEIQCIS

RVYSIYVHTVCDPLFEAVGKIF SNVRINLQKEI

Based on the disclosure herein, it is well within the level of those of skill in the art to identify membrane binding elements suitable for use in producing the modified capsid proteins, capsids, multimeric assemblies, and modified non-enveloped viruses disclosed herein. In one embodiment, a suitable membrane binding element can be identified as follows: As described throughout, a membrane binding element for use in the present disclosure can be any suitable polypeptide element that is capable of binding to a lipid bilayer via any suitable mechanism, including but not limited to non-covalently interacting with the lipid bilayer membrane. As will be known to those of skill in the art, a membrane binding element can be demonstrated to perform the function of membrane binding using a variety of standard assays. Many in vitro assays exist for assaying whether or not a polypeptide interacts with lipid membranes and for evaluating the characteristics of the interaction, such as the nature of the interaction (e.g., electrostatic or hydrophobic), the strength of the interaction, and whether the interaction deforms or remodels the membrane. Such assays include but are not limited to vesicle sedimentation assays, vesicle co-flotation assays, isothermal titration calorimetry, measuring changes in intrinsic or extrinsic protein or lipid fluorescence, fluorescence anisotropy, and membrane morphology analysis by electron microscopy or fluorescence microscopy (Zhao H, Lappalainen P (2012) A simple guide to biochemical approaches for analyzing lipid-protein interactions. Mol. Biol. Cell 23:2823-30). In addition, membrane binding element-dependent localization of proteins to membranes in cells can also be used as an assay for the interaction of a membrane binding element with membranes, and can yield information about the specificity of a given M domain for particular membranes, membrane subdomains, or lipids (Zacharias D A, Violin J D, Newton A C, Tsien R Y (2002) Partitioning of lipid-modified GFPs into membrane microdomains in live cells. Science 296:913-916; Lemmon M A (2008) Membrane recognition by phospholipid-binding domains. Nat. Rev. Mol. Cell. Biol. 9:99-111). Whether in vitro or in cells, either an isolated membrane binding element or a membrane binding element linked via genetic fusion or another method to a carrier protein that facilitates observation (for example, green fluorescent protein) can be used to evaluate the ability of the membrane binding element to interact with lipid membranes.

2. ESCRT-Recruiting Element

The ESCRT-recruiting element, also referred to as an "L domain," can be used in any suitable polypeptide that is capable of effecting membrane scission by recruiting the ESCRT machinery to the site of budding by binding to one or more ESCRT or ESCRT-associated proteins directly or indirectly via any suitable mechanism, including but not limited to non-covalently or covalently. Preferably, the ESCRT-recruiting element interacts with proteins known to recruit the ESCRT machinery to sites of budding in vivo, such as Tsg101, ALIX, or the Nedd4 family of ubiquitin E3 ligases (McDonald B, Martin-Serrano J (2009) No strings attached: the ESCRT machinery in viral budding and cytokinesis. J. Cell Sci. 122:2167-77; Votteler J, Sundquist W I (2013) Virus budding and the ESCRT pathway. Cell Host & Microbe 14:232-41). Most preferably, the ESCRT-recruiting element interacts with the human, murine, or other mammalian forms of these proteins. Each protein subunit in a multimeric assembly contains one or more L domains. The ESCRT-recruiting elements present in a resulting multimeric assembly may all be the same, all different, or some the same and some different.

In various embodiments, the one or more ESCRT-recruiting element can comprise or consist of a linear amino acid sequence motif selected from the group consisting of P(T/S)AP (SEQ ID NO: 152), $\Phi YX_{0/2}(P/\Phi)X_{0/3}$íI/I), PPXY (SEQ ID NO: 153), and overlapping combinations thereof (Bieniasz P D (2006) Late budding domains and host proteins in enveloped virus release. Virology 344:55-63; Votteler J, Sundquist W I (2013) Virus budding and the ESCRT pathway. Cell Host & Microbe 14:232-41), where Φ denotes a hydrophobic residue, X can be any amino acid, and numbered subscripts indicate amino acid spacers of varying lengths. Such overlapping combinations include, but are not limited to P(T/S)APPXY (SEQ ID NO: 155), P(T/S)APYP(X)nL (SEQ ID NO: 156), PPXYP(T/S)AP (SEQ ID NO: 157), PPXYYP$(X)_n$L (SEQ ID NO: 158), YP$(X)_n$LPPXY (SEQ ID NO: 159), and YP$(X)_n$LPPXY (SEQ ID NO: 160).

Further exemplary ESCRT-recruiting element can comprise or consist of one or more of the peptides that follow:

```
                                (SEQ ID NO: 161)
PTAPPEE;

(SEQ ID NO: 162)
YPLTSL;

(SEQ ID NO: 163)
PTAPPEY;

(SEQ ID NO: 164)
YPDL;

(SEQ ID NO: 165)
FPIV;

(SEQ ID NO: 166)
PTAPPEY;

(SEQ ID NO: 167)
PTAP;

(SEQ ID NO: 168)
PPEY;

(SEQ ID NO: 169)
YPLTSL;
and/or (SEQ ID NO: 165)
FPIV.
```

As will be understood by those of skill in the art, the ESCRT-recruiting element can include additional sequences, beyond those directly responsible for recruiting the ESCRT machinery, as appropriate for an intended use, so long as the ESCRT-recruitment motifs are not buried in the peptide core in such a way as to render them inaccessible for binding their interaction partners. In various further embodiments, the ESCRT-recruiting element can comprise or consist of the following peptides that include one or more ESCRT-recruitment motifs plus additional residues (ESCRT-recruitment motifs noted by underlined text):

```
                                        (SEQ ID NO: 172)
LQSRPE PTAPPEE SFRSGVETTTPPQKQEPIDKEL YPLTSLRSLFGN

DPSSQ; (HIV Gag p6 domain)
```

RRVILPTAPPEYMEAIYPVR; (residues 2-21 of Ebola VP40) (SEQ ID NO: 173)

PIQQKSQHNKSVVQETPQTQNLYPDLSEIKKEYNVKEKDQVEDLNLDSLWE; (EIAV Gag p9 domain) (SEQ ID NO: 174)

NPRQ SIKAFPIVINSDGGEK; (residues 12-31 of SV5 M) (SEQ ID NO: 175)

PTAPPEYGGS; (SEQ ID NO: 176)

PTAPGGS; (SEQ ID NO: 177)

PPEYGGS; (SEQ ID NO: 178)

YPLTSLGGS; (SEQ ID NO: 179)

YPDLGGS; (SEQ ID NO: 180)

FPIVGGS; (SEQ ID NO: 181)

LQSRPEAAAAPEESFRSGVETTTPPQKQEPIDKELYPLTSLRSLFGNDPSSQ, (HIV Gag p6 domain mutant p(APTAP)); (SEQ ID NO: 182)

and/or

LQSRPE PTAPPEE SFRSGVETTTPPQKQEPIDKELAALTSLRSLFGNDPSSQ, (HIV Gag p6 domain mutant p6(ΔYP)) (SEQ ID NO: 184)

Further exemplary ESCRT-recruiting elements can comprise or consist of one or more of the following polypeptides:

QSRPEPTAPPEESFRSGVETTTPPQKQEPIDKELYPLTSLRSLFGNDPSSQ (SEQ ID NO: 186)

DPQIPPPPYVEPTAPQV (SEQ ID NO: 187)

LLTEDPPPYRD (SEQ ID NO: 188)

TASAPPPPYVG (SEQ ID NO: 154)

TPQTQNLYPDLSEIK (SEQ ID NO: 171)

(M)RRVILPTAPPEYMEAI (SEQ ID NO: 170)

NTYMQYLNPPPYADHS (SEQ ID NO: 51)

LGIAPPPYEEDTSMEYAPSAP (SEQ ID NO: 50)

DDLWLPPPEYVPLKEL (SEQ ID NO: 49)

AAPTAPPTGAADSIPPPYSP (SEQ ID NO: 48)

TAPSSPPPYEE (SEQ ID NO: 47)

QSIKAFPIVINSDG (SEQ ID NO: 46)

SREKPYKEVTEDLLHLNSL (SEQ ID NO: 185)

AAGAYDPARKLLEQYAKK (SEQ ID NO: 22)

PNCFNSSINNIHEMEIQLKDALEKNQQWLVYDQQREVYVKGLLAKIFELEKKTETAAHSLPQQTKKPESEGYLQEEKQKC (SEQ ID NO: 23)

RKSPTPSAPVPLTEPAAQ (SEQ ID NO: 24)

(M)SLYPSLEDLKVDKVIQAQTAFSANPANPAILSEASAPIPHDGNLYPRLYPELSQYMGLSLN (SEQ ID NO: 25)

Based on the disclosure herein, it is well within the level of those of skill in the art to identify ESCRT-recruiting element suitable for use in producing the modified capsid proteins, multimeric assemblies, and modified non-enveloped viruses disclosed herein. As described herein, aESCRT-recruiting element for use in the present invention can be any suitable polypeptide domain that is capable of effecting membrane scission and release of an enveloped multimeric assembly from a cell by recruiting the ESCRT machinery to the site of budding by binding to one or more ESCRT proteins directly or indirectly via any suitable mechanism, including but not limited to non-covalently or covalently. As will be known to those with skill in the art, the ability of an ESCRT-recruiting element to recruit the ESCRT machinery and effect membrane scission and release of an enveloped multimeric assembly can be assessed using budding assays. In the budding assay, a candidate ESCRT-recruiting element is genetically fused to a viral structural protein that has been rendered defective in budding by mutation or deletion of its late domain, and the ability of the candidate ESCRT-recruiting element to restore budding of virus-like particles is evaluated by analyzing the culture supernatant for the presence of the viral structural protein using standard techniques such as SDS-PAGE and Western blotting (Parent L J, Bennett R P, Craven R C, Nelle T D, Krishna N K, Bowzard J B, Wilson C B, Puffer B A, Montelaro R C, Wills J W (1995) Positionally independent and exchangeable late budding functions of the Rous Sarcoma Virus and Human Immunodeficiency Virus Gag proteins. J. Virol. 69:5455-5460). Any viral structural protein that is known to be defective in budding can be used in the budding assay, including but not limited to budding-defective versions of HIV-1 Gag, RSV Gag, MuMoLV Gag, SV5 M, Ebola VP40 and other structural proteins from different families of enveloped viruses including retroviruses, filoviruses, rhabdoviruses, arenaviruses, and paramyxoviruses. In addition, as described below, the multimeric assemblies of the invention can be used to test the ability of an L domain to effect membrane scission and release of an enveloped multimeric assembly in a similar manner. The ESCRT-recruiting element of a modified capsid protein can be replaced with a candidate ESCRT-recruiting element, and the ability of the resulting construct to be released from cells can be determined by analyzing the culture supernatant for the presence of the protein subunits of the multimeric assembly using standard techniques such as SDS-PAGE and Western blotting. Finally, as will be known to those with skill in the art, the ability of an ESCRT-recruiting element to bind to one or more ESCRT proteins directly or indirectly can be assessed using a variety of biochemical, biophysical, and cell biological techniques including but not limited to co-immunoprecipitation, pull-down assays, isothermal titration calorimetry, biosensor binding assays, NMR spectroscopy, and X-ray crystallography.

3. Cargo

In some aspects, the disclosed modified capsid proteins can further comprise a desired cargo. The desired cargo can be, but is not limited to, a nucleic acid (e.g. a sequence of interest or a gene of interest), protein (e.g. a peptide of interest or a protein of interest), a ribonucleoprotein complex, a small molecule, or any combination thereof.

In some aspects, a desired cargo can be anything of interest that can be enclosed within a capsid or found on the surface of a capsid. In some aspects, a desired cargo can be linked to or interact with a packaging moiety disclosed herein and thus recruited to the multimeric assembly, including but not limited to therapeutics, diagnostics, antigens, adjuvants, imaging agents, dyes, radioisotopes, etc. In some aspects, if the desired cargo is a protein or polypeptide, the cargo can be expressed as a genetic fusion with the membrane binding element, or the ESCRT-recruiting element in order to directly incorporate the desired cargo into a modified capsid protein or multimeric assembly without the use of a distinct packaging moiety. In various embodiments, the desired cargo can be selected from the group consisting of, but not limited to, proteins, nucleic acids, lipids, small organic compounds or combinations thereof.

In some aspects, the cargo can be a detectable label.

In some aspects, the desired cargo comprises a polynucleotide with a nucleic acid sequence which is a recognition sequence known to bind to the corresponding packaging moieties described herein. In some aspects, the polynucleotide with a nucleic acid sequence which is a recognition sequence known to bind to a packaging moiety can be

```
                                        (SEQ ID NO: 26)
GGUCUGGGCGCACUUCGGUGACGGUACAGGCC
(Ig70 RNA sequence)

(SEQ ID NO: 27)
AAUCCAUUGCACUCCGGAUUU
(ula RNA sequence)

(SEQ ID NO: 28)
GGCGACUGGUGAGUACGCCAAAAAUUUUGACUAGCGGAGGCUAG
(HIV_NC RNA sequence)

(SEQ ID NO: 29)
GGCUCGUGUAGCUCAUUAGCUCCGAGCC
(lmnb RNA sequence)
```

In some aspects, the capsid protein is translated from a nucleic acid sequence that itself is replicated by the viral enzymes together with the nucleic acid sequence encoding the cargo. In this case, both the polynucleotide sequences encoding the capsid as well as the cargo contain recognition sequences for the viral replication enzymes. In some aspects, the nucleic acid sequence to bind a viral replication enzyme can be:

```
                                        (SEQ ID No 30)
GTAAACAATTCCAAGTTCCAAAATGGTTAATAACAACAGACCAAGACGTC

AACGAGCTCAACGCGTTGTCGTCACAACAACCCAAACAGCGCCTGTTCCA

CAGCAAAACGTGCCACGTAATGGTAGACGCCGACGTAATCGCACGAGGCG

TAATCGCCGACGTGTGCGCGGAATGAACATGGCGGCGCTAACCAGATTAA

GTCAACCTGGTTTGGCGTTTCTCAAATGTGCATTTGCACCACCTGACTTT

CATTCAGGTACGCTTCCATGAACGTGGGTATTTACCCAACGTCGAACTTG

ATGCAGTTTGCCGGAAGCATAACTGTTTGGAAATGCCCTGTAAAGCTGAG

TACTGTGCAATTCCCGGTTGCAACAGATCCAGCCACCAGTTCGCTAGTTC

ATACTCTTGTTGGTTTAGATGGTGTTCTAGCGGTGGGGCCTGACAACTTC

TCTGAGTCATTCATGAAGGATTTGGCTTTTAGAAGCATCCGGACGCCAAC

CTAACCGGGCAAGTATCCGAACAATCGGACATTTGGCCACAATAAGCCCA

ATTTGGTTGAAGATTAAAGTAGTGAGCCCCCTTAGCGCGAAACCGGAATT

TATATTCCAAACCAGTTTAAGTCAACAGACTAAGGT
(Flock House Virus defective interfering (DI)-RNA
sequence).
```

In some aspects, the desired cargo comprises a nucleic acid comprising one or more of the disclosed recognition sequences. Examples can be found in International Application Publication No WO 2016/138525, herein incorporated by reference in its entirety.

4. Packaging Moiety

In a further embodiment, the capsids, multimeric assemblies, or modified non-enveloped viruses of any embodiment or combination of embodiments herein can further comprise a packaging moiety. As used herein, a "packaging moiety" can be any moiety capable of interacting with a desired "cargo", with the effect of recruiting the cargo to the capsid, multimeric assembly, or modified non-enveloped virus. The interaction between the packaging moiety and the cargo can be any type of interaction, covalent or non-covalent, that results in effective interaction with and recruitment to the capsid, multimeric assembly, or modified non-enveloped virus. As will be apparent to those of skill in the art, the ability to widely modify surface amino acid residues without disruption of the protein structure permits many types of modifications to endow the resulting self-assembled multimers with a variety of functions. In one non-limiting example, at least one of the modified capsid proteins can be modified, such as by introduction of various cysteine residues or non-canonical amino acids at defined positions to facilitate linkage to one or more cargo of interest. In another non-limiting example, the modified capsid protein can be modified to comprise as a genetic fusion a polypeptide domain or sequence known to interact with a desired cargo covalently or non-covalently. In one embodiment, a non-canonical amino acid can be incorporated recombinantly using amber codon suppression (see L. Wang, A. Brock, B. Herberich, P. G. Schultz, Science 292, 498 (2001)). In another embodiment, the packaging moiety comprises the polypeptide sequence:

```
                                        (SEQ ID NO: 186)
QSRPEPTAPPEESFRSGVETTTPPQKQEPIDKELYPLTSLRSLFGNDP

SSQ,
``` wherein the packaging moiety polypeptide is expressed as a genetic fusion with the M domain or the L domain. This sequence is the p6 domain of HIV Gag, which is known to interact with the HIV protein Vpr via a non-covalent protein-protein interaction (Cavrois M, et al. (2002) Nat. Biotech. 20: 1151-4). For example, by including SEQ ID NO: 186 in a multimeric assembly of the invention, any polypeptide sequence or other molecule that is fused, tethered, or otherwise connected to the Vpr sequence can be packaged into the multimeric assembly.

In some aspects, the packaging moiety can be bound or fused to the membrane binding element, the ESCRT-recruiting element, or the capsid-forming protein.

Additional packaging moieties can comprise or consist of one or more of the following peptides expressed as a genetic fusion with the membrane binding element, the ESCRT-recruiting element, or the capsid-forming protein, each of which binds to corresponding recognition sequences present in a nucleic acid cargo of interest, resulting in recruitment of the nucleic acid cargo of interest to the multimeric assembly.

(a) DRRRRGSRPSGAERRRRRAAAA (Ig70) (SEQ ID NO: 31)

(b) AVPETRPNHTIYINNLNEKIKKDELKKSLHAIFSRFGQILDILVS
RSLKMRGQAFVIFKEVSSATNALRSMQGFPFYDKPMRIQYAKTDSDIIA
KMK (u1a) (SEQ ID NO: 32)

(c) (M)QKGNFRNQRKTVKCFNCGKEGHIAKNCRAPRKKGCWKCGKEG
HQMKDCTERQAN, (HIV NC)
and/or (SEQ ID NO: 33)

(d) RPRGTRGKGRRIRR (mnb) (SEQ ID NO: 34)

(e) MVNNNRPRRQRAQRVVVTTTQTAPVPQQNVP
(FHV Alpha1-31) (SEQ ID NO: 35)

(f) MTLKVILGEHQITRTELLVGIATVSGCGAVVYCISKFWGYGAIAP
YPQSGGNRVTRALQRAVIDKTKTPIETRFYPLDSLRTVTPKRVADNGHA
VSGAVRDAARRLIDESITAVGGSKFEVNPNPNSSTGLRNHFHFAVGDLA
QDFRNDTPADDAFIVGVDVDYYVTEPDVLLEHMRPVVLHTFNPKKVSGF
DADSPFTIKNNLVEYKVSGGAAWVHPVWDWCEAGEFIASRVRTSWKEWF
LQLPLRMIGLEKVGYHKIHHCRPWTDCPDRALVYTIPQYVIWRFNWIDT
ELHVRKLKRIEYQDETKPGWNRLEYVTDKNELLVSIGREGEHAQITIEK
EKLDMLSGLSATQSVNARLIGMGHKDPQYTSMIVQYYTGKKVVSPISPT
VYKPTMPRVHWPVTSDADVPEVSARQYTLPIVSDCMMMPMIKRWETMSE
SIERRVTFVANDKKPSDRIAKIAETFVKLMNGPFKDLDPLSIEETIERL
NKPSQQLQLRAVFEMIGVKPRQLIESFNKNEPGMKSSRIISGFPDILFI
LKVSRYTLAYSDIVLHAEHNEHWYYPGRNPTEIADGVCEFVSDCDAEVI
ETDFSNLDGRVSSWMQRNIAQKAMVQAFRPEYRDEIISFMDTIINCPAK
AKRFGFRYEPGVGVKSGSPTTTPHNTQYNGCVEFTALTFEHPDAEPEDL
FRLIGPKCGDDGLSRAIIQKSINRAAKCFGLELKVERYNPEIGLCFLSR
VFVDPLATTTTIQDPLRTLRKLHLTTRDPTIPLADAACDRVEGYLCTDA
LTPLISDYCKMVLRLYGPTASTEQVRNQRRSRNKEKPYWLTCDGSWPQH
PQDAHLMKQVLIKRTAIDEDQVDALIGRFAAMKDVWEKITHDSEESAAA
CTFDEDGVAPNSVDESLPMLNDAKQTRANPGTSRPHSNGGGSSHGNELP
RRTEQRAQGPRQPARLPKQGKTNGKSDGNITAGETQRGGIPRGKGPRGG
KTNTRRTPPKAGAQPQPSNNRKLEKLASRSEQKLISEEDL
(FHV Protein A) (SEQ ID NO: 36)

5. Additional Moieties

In some aspects, the disclosed capsids, multimeric assemblies, and modified non-enveloped viruses further comprise one or more transmembrane protein or membrane-anchored protein embedded in the lipid bilayer. This embodiment can be used to add additional functionality of any desired type to the capsids, multimeric assemblies, and modified non-enveloped viruses. In this embodiment, the transmembrane protein or membrane-anchored protein can be one not present as part of the capsid or modified capsid proteins, in that they are added to the assembly or virus during or after envelopment of the multimeric assembly and modified non-enveloped virus by the lipid bilayer and do not necessarily interact with the protein subunits either covalently or non-covalently. Any suitable transmembrane protein or membrane-anchored protein can be added that provides any desired additional functionality to the assembly, in terms of cell targeting, the display of transmembrane or membrane-anchored antigen for vaccines, or other desired use. In one non-limiting example, the transmembrane protein or membrane-anchored protein embedded in the lipid bilayer comprises a viral envelope protein that enables the enveloped multimeric assembly, capsid or modified non-enveloped virus to enter cells via receptor-mediated endocytosis and/or mediates fusion of the lipid bilayer of the enveloped multimeric assembly, capsid or modified non-enveloped virus with cellular membranes. In the study of enveloped viruses, the practice of incorporating a foreign viral envelope protein in the membrane of an enveloped virus is referred to as "pseudotyping." By co-expressing the foreign viral envelope protein with the viral or virus-like particle proteins, the foreign viral envelope protein becomes embedded in the membrane bilayer of the cells, and is therefore incorporated into the membrane envelope of the budding virions or virus-like particles. As the inventors have shown below, viral envelope proteins (in one embodiment, the G protein of Vesicular Stomatitis Virus) can be incorporated in the membrane envelopes of the enveloped multimeric assemblies, capsids or modified non-enveloped viruses of the disclosure in a similar manner. In various non-limiting embodiments, additional classes of membrane proteins can be incorporated into the membrane envelopes of the multimeric assemblies, capsid or modified non-enveloped viruses of the disclosure. In various non-limiting embodiments, the transmembrane or membrane-anchored protein is selected from the group consisting of the envelope proteins of enveloped viruses, membrane protein transporters, membrane protein channels, B cell receptors, T cell receptors, transmembrane antigens of human pathogens, growth factors receptors, G-protein coupled receptors (GPCRs), complement regulatory proteins including but not limited to CD55 and CD59, or processed versions thereof.

In specific embodiments, the one or more transmembrane protein or membrane-anchored protein embedded in the lipid bilayer comprise one or more of the following polypeptides, or a processed version thereof. As will be understood by those of skill in the art, the polypeptide sequences provided are full-length protein precursors, which are cleaved or otherwise processed (i.e., "processed") to generate the final envelope protein embedded in the lipid bilayer.

VSV-G
(SEQ ID NO: 37)
MKCLLYLAFLFIGVNCKFTIVFPHNQKGNWKNVPSNYHYCPSSSDLNWHN
DLIGTALQVKMPKSHKAIQADGWMCHASKWVTTCDFRWYGPKYITHSIRS
FTPSVEQCKESIEQTKQGTWLNPGFPPQSCGYAWTDAEAVIVQVTPHHVL
VDEYTGEWVDSQFINGKCSNYICPTVHNSTTWHSDYKVKGLCDSNLISMD
ITFFSEDGELSSLGKEGTGFRSNYFAYETGGKACKMQYCKHWGVRLPSGV

WFEMADKDLFAAARFPECPEGSSISAPSQTSVDVSLIQDVERILDYSLCQ

ETWSKIRAGLPISPVDLSYLAPKNPGTGPAFTIINGTLKYFETRYIRVDI

AAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPI

ELVEGWFSSWKSSIASFFFIIGLIIGLFLVLRVGIHLCIKLKHTIKKRQI

YTDIEMNRLGK;

Ecotropic envelope protein from Moloney Murine
Leukemia Virus or "Eco"
(SEQ ID NO: 38)
MARSTLSKPLKNKVNPRGPLIPIALLMLRGVSTASPGSSPFIQVYNITWE

VINGDRETVWATSGNHPLWTWWPDLTPDLCMLAHHGPSYWGLEYQSPFSS

PPGPPCCSGGSSPGCSRDCEEPLTSLTPRCNTAWNRLKLDQTTHKSNEGF

YVCPGPHRPRESKSCGGPDSFYCAYWGGETTGRAYWKPSSSWDFITVNNN

LTSDQAVQVCKDNKWCNPLVIRFTDAGRRVTSWTTGHYNWGLRLYVSGQD

PGLTFGIRLRYQNLGPRVPIGPNPVLADQQPLSKPKPVKSPSVTKPPSGT

PLSPTQLPPAGTENRLLNLVDGAYQALNLTSPDKTQECWLCTVAGPFYE

GVAVLGTYSNHTSAPANCSVASQHKLTLSEVTGQGLCIGAVPKTHQALCN

TTQTSSRGSYYLVAPTGTMWACSTGLTPCISTTILNLTTDYCVLVELWPR

VTYHSPSYVYGLFERSNRHKREPVSLTLALLLGGLTMGGIAAGIGTGTTA

LMATQQFQQLQAAVQDDLREVEKSISNLEKSLTSLSEVVLQNRRGLDLLF

LKEGGLCAALKEECCFYADHTGLVRDSMAKLRERLNQRQKLFESTQGWTE

GLFNRSPWFTTLISTIMGPLIVLLMILLFGPCILNRLVQFVKDRISVVQA

LVLTQQYHQLKPIEYEP;

Amphotropic Murine Leukemia Virus Envelope 4070A
(SEQ ID NO: 39)
MARSTLSKPPQDKINPWKPLIVMGVLLGVGMAESPHQVFNVTWRVTNLMT

GRTANATSLLGTVQDAFPKLYFDLCDLVGEEWDPSDQEPYVGYGCKYPAG

RQRTRTFDFYVCPGHTVKSGCGGPGEGYCGKWGCETTGQAYWKPTSSWDL

ISLKRGNTPWDTGCSKVACGPCYDLSKVSNSFQGATRGGRCNPLVLEFTD

AGKKANWDGPKSWGLRLYRTGTDPITMFSLTRQVLNVGPRVPIGPNPVLP

DQRLPSSPIEIVPAPQPPSPLNTSYPPSTTSPTSPTSPSVPQPPPGTG

DRLLALVKGAYQALNTNPDKTQECWLCLVSGPPYYEGVAVVGTYTNHST

APANCTATSQHKLTLSEVTGQGLCMGAVPKTHQALCNTTQSAGSGSYYLA

APAGTMWACSTGLTPCLSTTVLNLTTDYCVLVELWPRVIYHSPDYMYGQL

EQRTKYKREPVSLTLALLLGGLTMGGIAAGIGTGTTALIKTQQFEQLHAA

IQTDLNEVEKSITNLEKSLTSLSEVVLQNRRGLDLLFLKEGGLCAALKEE

CCFYADHTGLVRDSMAKLRERLNQRQKLFETGQGWFEGLFNRSPWFTTLI

STIMGPLIVLLLILLFGPCILNRLVQFVKDRISVVQALVLTQQYHQLKPI

EYEP;

Sindbis virus E3-E2-6K-E1 envelope polyprotein
(SEQ ID NO: 40)
SAAPLVTAMCLLGNV SFPCDRPPTCYTREP

SRALDILEENVNHEAYDTLLNAILRCGS

SGRSKRSVIDDFTLTSPYLGTCSYCHHTVPCFSPVKIEQVWDEADDNTIR

IQTSAQFGYDQSGAASANKYRYMSLKQDHTVKEGTMDDIKISTSGPCRRL

SYKGYFLLAKCPPGDSVTVSIVSSNSATSCTLARKIKPKFVGREKYDLPP

VHGKKIPCTVYDRLKETTAGYITMHRPRPHAYTSYLEESSGKVYAKPPSG

KNnYECKCGDYKTGTVSTRTEITGCTAIKQCVAYKSDQTKWVFNSPDLIR

HDDHTAQGKLHLPFKLIPSTCMVPVAHAPNVIHGFKHISLQLDTDHLTLL

TTRRLGANPEPTTEWIVGKWRNFWDRDGLEYIWGNHEPVRVYAQESAPGD

PHGWPHEIVQHYYHRHPWTILAVASAWAMMIGVTVAVLCACKARRECLTP

YALAPNAVIPTSLALLCCVRSANAETFTETMSYLWSNSQPFFWVQLCIPL

AAFIVLMRCCSCCLPFLVVAGAYLAKVDAYEHATWPNVPQIPYKALVERA

GYAPLNLEITVMSSEVLPSTNQEYITCKFTTVVPSPKIKCCGSLECQPAA

HADYTCKVFGGVYPFMWGGAQCFCDSENSQMSEAYVELSADCASDHAQAI

KVHTAAMKVGLRIVYGNTTSFLDVYVNGVTPGTSKDLKVIAGPISASFTP

FDHKVVIHRGLVYNYDFPEYGAMKPGAFGDIQATSLTSKDLIASTDIRLL

KPSAKNVHVPYTQASSGFEMWKNNSGRPLQETAPFGCKIAVNPLRAVDCS

YGNIPISIDIPNAAFIRTSDAPLVSTVKCEVSECTYSADFGGMATLQYVS

DREGQCPVHSHSSTATLQESTVHVLEKGAVTVHFSTASPQANFIVSLCGK

KTTCNAECKPPADHIVSTPHKNDQEFQAAISKTSWSWLFALFGGASSLLI

IGLMIFACSMMLTSTRR;

Ebola GP (Zaire Mayinga strain)
(SEQ ID NO: 41)
MGVTGILQLPRDRFKRTSFFLWVIILFQRTFSIPLGVIHNSTLQVSDVDK

LVCRDKLSSTNQLRSVGLNLEGNGVATDVPSATKRWGFRSGVPPKVVNYE

AGEWAENCYNLEIKKPDGSECLPAAPDGIRGFPRCRYVHKVSGTGPCAGD

FAFHKEGAFFLYDRLASTVIYRGTTFAEGVVAFLILPQAKKDFFSSHPLR

EPVNATEDPSSGYYSTTIRYQATGFGTNETEYLFEVDNLTYVQLESRFTP

QFLLQLNETIYTSGKRSNTTGKLIWKVNPEIDTTIGEWAFWETKKNLTRK

IRSEELSFTVVSNGAKNISGQSPARTSSDPGTNTTTEDHKIMASENSSAM

VQVHSQGREAAVSHLTTLATISTSPQSLTTKPGPDNSTHNTPVYKLDISE

ATQVEQHHRRTDNDSTASDTPSATTAAGPPKAENTNTSKSTDFLDPATTT

SPQNHSETAGNNNTHHQDTGEESASSGKLGLITOTIAGVAGLITGGRRTO

REAIVNAQPKCNPNLHYWTTQDEGAAIGLAWIPYFGPAAEGIYIEGLMHN

QDGLICGLRQLANETTQALQLFLRATTELRTFSILNRKAIDFLLQRWGGT

CHILGPDCCIEPHDWTKNITDKIDQIIHDFVDKTLPDQGDNDNWWTGWRQ

WIPAGIGVTGVIIAVIALFCICKFVF;

Human Immunodeficiency Virus envelope glycoprotein
precursor gp160
(SEQ ID NO: 42)
MRVKEKYQHLWRWGWKWGIMLLGILMICSATENLWVWYYGVPVWKEATTT LFCASDAKAYDTEVIiNVCATHACVPTDPNPQEVILVNVTENFDMWKNDM

VEQMHEDIISLWDQSLKPCVKLTPLCVNLKCTDLKNDTOTOSSNGRMIME

KGEIKNCSFNISTSIRNKVQKEYAFFYKLDIRPIDNTTYRLISCNTSVIT

QACPKVSFEPIPIHYCAPAGFAILKCNDKTFNGTGPCTNVSTVQCTHGIR

PVVSTQLLLNGSLAEEEGVIRSANFTDNAKTIIVQLNTSVEINCTRPNNN

-continued

TRKSIRIQRGPGRAFVTIGKIGNMRQAHCNISRAKWMSTLKQIASKLREQ

FGNNKTVIFKQSSGGDPEIVTHSFNCGGEFFYCNSTQLFNSTWFNSTWST

EGSNNTEGSDTITLPCRIKQFINMWQEVGKAMYAPPISGQIRCSSNITGL

LLTRDGGKNTNESEVFRPGGGDMRDNWRSELYKYKVVKIETLGVAPTKAK

RRVVQREKRAVGIGALFLGFLGAAGSTMGAASMTLTVQARQLLSGIVQQQ

NNLLRAIEAQQHLLQLTVWGIKQLQARILAVERYLKDQQLLGIWGCSGKL

ICTTAVPWASWSNKSLEQFWNNMTWMEWDREINNYTSLIHSLIDESQNQQ

EKNEQELLELDKWASLWT△TMITT△LWIKIFIMIVGGLVGLRIVFAVLSI

VNRVRQGYSPLSFQTHLPNRGGPDRPEGIEEEGGERDRDRSVRLVNGSLA

LIWDDLRSLCLFSYHRLRDLLLIVTRIVELLGRRGWEALKYWWNLLQYWS

QELKNSAVSLLNATAIAVAEGTDRVIEVVQGAYRAIRHIPRRIRQGLERI

L;

Respiratory Syncytial Virus F protein precursor
(SEQ ID NO: 43)
MELLILKANAITTILTAVTFCFASGQNITEEFYQSTCSAVSKGYLSALRT

GWYTSVITIELSNIKENKCNGTDAKVKLIKQELDKYKNAVTELQLLMQST

PPTONRARRELPRFMNYTLNNAKKTNVTLSKKRKRRFLGFLLGVGSAIAS

GVAVSKVLHLEGEVNKIKSALLSTNKAVVSLSNGVSVLTSKVLDLKNYID

KQLLPIVNKQSCSISNIETVIEFQQKNNRLLEITREFSVNAGVTTPVSTY

MLTOSELLSLINDMPITNDQKKLMSNNVQIVRQQSYSIMSIIKEEVLAYV

VQLPLYGVIDTPCWKLHTSPLCTTNTKEGSNICLTRTDRGWYCDNAGSVS

FFPQAETCKVQSNRVFCDTTVINSLTLPSEINLCNVDIFNPKYDCKIMTS

KTDVSSSVITSLGAIVSCYGKTKCTASNKNRGIIKTFSNGCDYVSNKGMD

TVSVGNTLYYVNKQEGKSLYVKGEPIINFYDPLVFPSDEFDASISQVNEK

INQSLAFIRKSDELLHNVNAGKSTTNIMITTIIIVIIVILLSLIAVGLLL

YCKARSTPVTLSKDQLSGINNIAFSN;

SARS Coronavirus spike protein
(SEQ ID NO: 44)
MFIFLLFLTLTSGSDLDRCTTFDDVQAPNYTQHTSSMRGVYYPDEIFRSD

TLYLTQDLFLPFYSNVTGFHTINHTFGNPVIPFKDGIYFAATEKSNVVRG

WVFGSTMNNKSQSVIIINNSTNVVIRACNFELCDNPFFAVSKPMGTQTHT

MIFDNAFNCTFEYISDAFSLDVSEKSGNFKHLREFVFKNKDGFLYVYKGY

QPIDVVRDLPSGFNTLKPIFKLPLGINITNFRAILTAFSPAQDIWGTSAA

AYFVGYLKPTTFMLKYDENGTITDAVDCSQNPLAELKCSVKSFEIDKGIY

QTSNFRVVPSGDVVRFPNITNLCPFGEVFNATKFPSVYAWERKKISNCVA

DYSVLYNSTFFSTFKCYGVSATKLNDLCFSNVYADSFVVKGDDVRQIAPG

QTGVIADYNYKLPDDFMGCVLAWNTRNIDATSTGNYNYKYRYLRHGKLRP

FERDISNVPFSPDGKPCTPPALNCYWPLNDYGFYTTTGIGYQPYRVVVLS

FELLNAPATVCGPKLSTDLIKNQCVNFNFNGLTGTGVLTPSSKRFQPFQQ

FGRDVSDFTDSVRDPKTSEILDISPCSFGGVSVITPGTNASSEVAVLYQD

VNCTDVSTAIHADQLTPAWRIYSTGNNVFQTQAGCLIGAEHVDTSYECDI

PIGAGICASYHTVSLLRSTSQKSIVAYTMSLGADSSIAYSNNTIAIPTNF

SISITTEVMPVSMAKTSVDCNMYICGDSTECANLLLQYGSFCTQLNRALS

GIAAEQDRNTREVFAQVKQMYKTPTLKYFGGFNFSQILPDPLKPTKRSFI

EDLLFNKVTLADAGFMKQYGECLGDINARDLICAQKFNGLTVLPPLLTDD

MIAAYTAALVSGTATAGWTFGAGAALQIPFAMQMAYRFNGIGVTQNVLYE

NQKQIANQFNKAISQIQESLTTTSTALGKLQDVVNQNAQALNTLVKQLSS

NFGAISSVLNDILSRLDKVEAEVQIDRLITGRLQSLQTYVTQQLIRAAEI

RASANLAATKMSECVLGQSKRVDFCGKGYHLMSFPQAAPHGVVFLHVTYV

PSQERNFTTAPAICHEGKAYFPREGVFVFNGTSWFITQRNFFSPQIITTD

NTFVSGNCDVVIGIINNTVYDPLQPELDSFKEELDKYFKNHTSPDVDLGD

ISGINASVVNIQKEIDRLNEVAKNLNESLIDLQELGKYEQYIKWPWYVWL

GFIAGLIAIVMVTILLCCMTSCCSCLKGACSCGSCCKFDEDDSEPVLKGV

KLHYT;

Influenza hemaglutinin
(SEQ ID NO: 45)
MKTIIALSYIFCLALGQDLPGNDNSTATLCLGHHAVPNGTLVKTITDDQI

EVTNATELVQ

SSSTGKICNNPHRILDGIDCTLIDALLGDPHCDVFQNETWDLFVERSKAF

SNCYPYDVPD

YASLRSLVASSGTLEFITEGFTWTGVTQNGGSNACKRGPGSGFFSRLNWL

TKSGSTYPVLNVTMPNNDNFDKLYIWGIHHPSTNQEQTSLYVQASGRVTV

STRRSQQTIIPNIGSRPWVRGLSSRISIYWTIVKPGDVLVINSNGNLIAP

RGYFKMRTGKSSIMRSDAPIDTCISECITP

NGSIPNDKPFQNVNKnYGACPKYVKQNTLKLATGMRNVPEKQTRGLFGAI

AGFIENGWEGMIDGWYGFRHQNSEGTGQAADLKSTQAAIDQINGKLNRVI

EKTNEKFHQIEKEFSEVEGRIQDLEKYVEDTKIDLWSYNAELLVALENQH

TIDLTDSEMNKLFEKTRRQLRENAEEMGNGCFKIYHKCDNACIESIRNGT

YDHDVYRDEALNNRFQIKGVELKSGYKDWILWISFAISCFLLCVVLLGFI

MWACQRGNIRCNICI.

In some aspects, any known targeting moiety can be used. A targeting moiety can be any nucleic acid or amino acid sequence that targets a particular cell surface protein or intracellular target.

As used herein, the term "targeting moiety" refers to any moiety that specifically binds a selected target. The targeting moiety can be, for example, a polysaccharide, a peptide, peptide ligand, an aptamer, an antibody or fragment thereof, a single chain variable fragment (scFv) of an antibody, or a Fab' fragment, or a nanobody. Targeting moieties can also include other forms of an antibody as disclosed in Rissiek et al.; "Nanobodies as modulators of inflammation: potential applications for acute brain injury," Front. Cell. Neurosci., 21 Oct. 2014; and Cuesta et al.; "Multivalent antibodies: when design surpasses evolution;" Trends in Biotechnology; Vol. 28, Issue 7, pp. 355-362, July 2010. The cited references are incorporated herein by reference in their entirety.

As used herein, a "targeting moiety" can be specific to a recognition molecule on the surface of a cell or a population of cells, such as, for example B cells or T cells. In an aspect of the disclosed compositions and methods, a targeting moiety can include, but is not limited to: a monoclonal antibody, a polyclonal antibody, full-length antibody, a chimeric antibody, Fab', Fab, F(ab)$_2$, F(ab')$_2$, a single domain antibody, Fv, a single chain Fv (scFv), a minibody, a diabody, a triabody, hybrid fragments, a phage display antibody, a ribosome display antibody, an oligonucleotide, a modified oligonucleotide, a peptide, a peptide ligand, a hormone, a growth factor, a cytokine, a saccharide or polysaccharide, and an aptamer.

As used herein, "aptamers" refer to molecules that interact with a target molecule, preferably in a specific way. Typically, aptamers are small nucleic acids ranging from 15-50 bases in length that fold into defined secondary and tertiary structures, such as stem-loops or G-quartets. Aptamers can bind small molecules and large molecules. Aptamers can bind very tightly with Kd's from the target molecule of less than $10^{-12}$ M. Aptamers can bind the target molecule with a very high degree of specificity. Aptamers are known to the art and representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698. In an aspect, the aptamer can be synthetic, nonimmunogenic antibody mimics. In an aspect, the aptamer can be a DNA aptamer. In an aspect, the DNA aptamer can be anti-PD-1 aptamer.

As used herein, the term "contacting" refers to bringing a disclosed composition, compound, conjugate or protein together with an intended target (such as, e.g., a cell or population of cells, a receptor, an antigen, or other biological entity) in such a manner that the disclosed composition, compound, conjugate or fusion protein can affect the activity of the intended target (e.g., receptor, transcription factor, cell, population of cells, etc.), either directly (i.e., by interacting with the target itself), or indirectly (i.e., by interacting with another molecule, co-factor, factor, or protein on which the activity of the target is dependent). In an aspect, a disclosed composition or fusion protein can be contacted with a cell or population of cells, such as, for example, one or more lymphocytes (e.g., T cells and/or B cells).

C. Capsid

Disclosed are capsids comprising a plurality of the modified capsid proteins disclosed herein. Thus, for example, disclosed are capsids comprising a plurality of modified capsid proteins, wherein the modified capsid proteins comprise a capsid forming protein, a membrane binding element and an ESCRT-recruiting element, wherein at least one of the membrane binding element and the ESCRT-recruiting element is heterologous to the capsid forming protein.

In some aspects, the modified capsid proteins are derived from a non-envelope virus. In other words, the modified capsid proteins can comprise a capsid forming protein, a membrane binding element and an ESCRT-recruiting element, wherein at least one of the membrane binding element and the ESCRT-recruiting element is heterologous to the capsid forming protein and wherein the capsid forming protein can be a capsid forming protein of a non-enveloped virus. If the capsid forming protein is from a non-enveloped virus then the capsid can be referred to as a non-enveloped capsid.

In some aspects, the plurality of modified capsid proteins interact with each other forming the capsid.

In some aspects, the membrane binding element and ESCRT-recruiting element can be located within a region of the plurality of modified capsid proteins that does not disrupt the ability of the capsid to form.

In some aspects, the disclosed capsids can further comprise a packaging moiety as described herein. The packaging moiety can be present on one or more of the modified capsid proteins. In some aspects, the packaging moiety is bound to a desired cargo. For example, the packaging moiety can be bound to a desired cargo with a covalent or non-covalent bond. In some aspects, the packaging moiety can be a modified amino acid within one or more of the modified capsid proteins. In some aspects, the packaging moiety can be a polypeptide.

In some aspects, the disclosed capsids further comprise a desired cargo as described herein.

In some aspects, the disclosed capsids can further comprise a membrane surrounding the capsid. The membrane can be a lipid bilayer. Thus, the presence of a membrane surrounding a capsid comprised of modified capsid proteins, wherein the modified capsid proteins comprise capsid forming proteins of a non-enveloped virus can convert a non-enveloped capsid to an enveloped capsid.

D. Multimeric Assembly

Disclosed are multimeric assemblies comprising a one or more of the capsids disclosed herein within a membrane. Disclosed are multimeric assemblies comprising a two or more of the capsids disclosed herein within a membrane. Thus, for example, disclosed are multimeric assemblies comprising a plurality of capsids, wherein the capsids comprise a plurality of modified capsid proteins, wherein the modified capsid proteins comprise a capsid forming protein, a membrane binding element and an ESCRT-recruiting element, wherein at least one of the membrane binding element and the ESCRT-recruiting element is heterologous to the capsid forming protein.

In some aspects, the membrane binding element and ESCRT-recruiting element can be located within a region of the plurality of modified capsid proteins that does not disrupt the ability of the multimeric assembly to form.

As disclosed herein, the membrane can be a lipid bilayer. As used herein, the membrane can also be referred to as an envelope.

In some aspects, the multimeric assembly further comprises a packaging moiety. In some aspects, the packaging moiety can be bound to a desired cargo. In some aspects, the packaging moiety is bound to a desired cargo with a covalent or non-covalent bond. In some aspects, the packaging moiety can be a modified amino acid within one or more of the modified capsid proteins. In some aspects, the packaging moiety can be a polypeptide. In some aspects, the desired cargo can be a nucleic acid, protein, or small molecule. The packaging moiety and desired cargo can be any of those disclosed herein.

E. Modified Non-Enveloped Virus

Disclosed herein are modified non-enveloped viruses comprising one or more of the capsids disclosed herein. Thus, for example, disclosed are modified non-enveloped viruses comprising a capsid wherein the capsid comprises a plurality of modified capsid proteins, wherein the plurality of modified capsid proteins comprise a membrane binding element and an ESCRT-recruiting element, wherein at least one of the membrane binding element and the ESCRT-recruiting element is heterologous to the modified capsid protein, wherein the capsid forming protein is a capsid forming protein of a non-enveloped virus.

In some aspects, the membrane binding element and ESCRT-recruiting element can be located within any region of the modified capsid protein that they retain their function and do not inhibit assembly of a capsid. For example, in some aspects the membrane binding element and ESCRT-recruiting element can be located within at least one exposed surface loop of the modified capsid proteins. In some aspects, the membrane binding element and ESCRT-recruiting element can be located within the same exposed surface loop of the modified capsid protein. In some aspects, the membrane binding element and ESCRT-recruiting element can be located within different exposed surface loops of the modified capsid protein. In some aspects, the membrane-binding element and ESCRT-recruiting element can be located at either the N or C terminus of the modified capsid protein. In some aspects, the membrane-binding element can be located at either the N or C terminus of the modified capsid protein and the ESCRT-recruiting element can be located at the opposite terminus of the modified capsid protein from the membrane-binding element.

In some aspects, the modified non-enveloped virus can be, but is not limited to, Adenoviridae, Polyomaviridae, Papillomaviridae, Rudiviridae, Clavaviridae, Parvoviridae, Bimaviridae, Reovirideae, Totiviridae, Picomavirideae, Comovirinae, Bromoviridae, Hepeviridae, and Nodaviridae. Thus, the capsid forming protein can be a capsid forming protein of, but is not limited to, Adenoviridae, Polyomaviridae, Papillomaviridae, Rudiviridae, Clavaviridae, Parvoviridae, Bimaviridae, Reovirideae, Totiviridae, Picomavirideae, Comovirinae, Bromoviridae, Hepeviridae, or Nodaviridae.

In some aspects, the modified non-enveloped virus can be a Flock House Virus or Nodamura Virus. In some aspects, one or both of the membrane binding element and ESCRT-recruiting element are located at position 206 of the alpha protein of Flock House Virus. In some aspects, one or both of the membrane binding element and ESCRT-recruiting element are located at position 264 of the alpha protein of Flock House Virus. In some aspects, one or both of the membrane binding element and ESCRT-recruiting element can be located at position 199 of the alpha protein of Nodamura Virus. In some aspects, one or both of the membrane binding element and ESCRT-recruiting element can be located at position 259 of the alpha protein of NoV. In some aspects, membrane binding and ESCRT recruiting elements can be located at the N terminus of the VP2 protein of AAV. In some aspects, membrane binding and ESCRT recruiting elements can be located at the truncated N terminus of the VP2 protein of AAV.

In some aspects, the membrane binding element can be any of the membrane binding elements described herein. For example, the membrane binding element can be the membrane binding PH element from phospholipase C.

In some aspects, the ESCRT-recruiting element can be any of the ESCRT-recruiting elements described herein. For example, the ESCRT-recruiting element can be the $p6^{Gag}$ polypeptide from human immunodeficiency virus.

In some aspects, the disclosed modified non-enveloped viruses can further comprise a membrane surrounding the capsid. In some aspects, the membrane can be a lipid bilayer. In some aspects, the membrane can also be referred to as an envelope. Thus, the presence of the membrane surrounding the disclosed modified non-enveloped viruses can convert the modified non-enveloped viruses to enveloped viruses and can be referred to as quasi-enveloped viruses.

In some aspects, the membrane can comprise any of the targeting moieties described herein.

In some aspects, the disclosed modified non-enveloped viruses can be replication defective.

In some aspects, the disclosed modified non-enveloped viruses can comprise a desired cargo. The desired cargo can be any of those disclosed herein. In some aspects, the desired cargo can be the viral genome. In some aspects, the viral genome can be modified.

F. Nucleic Acid Sequences

Disclosed are nucleic acid sequences that encode any of the disclosed modified capsid proteins.

Disclosed are constructs comprising the nucleic acid sequence that encodes any of the modified capsid proteins disclosed herein.

Disclosed are constructs comprising a modified viral genome wherein the modified viral genome comprises a nucleic acid sequence capable of encoding any of the disclosed modified capsid proteins. In some aspects, the modified viral genome can be a modified Flock House Virus or Nodamuravirus genome. In some aspects, the modified viral genome can be a modified AAV genome.

In some aspects, a modified viral genome is a viral genome that renders the resulting virus replication defective.

G. Methods of Producing

Disclosed are methods of producing a vector comprising transfecting a cell with a packaging plasmid comprising a sequence of interest; and any of the constructs disclosed herein. In some aspects, the sequence of interest can be a therapeutic agent or a detectable agent.

H. Methods of Treating

Disclosed are methods of treating a subject with any of the disclosed capsids, any of the disclosed multimeric assemblies, any of the disclosed modified non-enveloped virus, or any of the disclosed vectors produced by the methods disclosed herein.

In some aspects, the sequence of interest encodes a protein that is non-functional or absent in the subject. In some aspects, the sequence of interest can be a therapeutic agent.

I. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing the disclosed modified capsid proteins, capsids, multimeric assemblies or modified non-enveloped viruses, the kit comprising a membrane binding element and an ESCRT-recruiting element. The kits also can contain lipids, desired cargo, or targeting moieties.

EXAMPLES

One goal of the current disclosure is to generate a virus-based vector system in which capsids from non-enveloped viruses are modified so that they efficiently bud from cells inside membrane enclosed vesicles, thereby converting non-enveloped viruses into quasi-enveloped viruses. Three modular activities are necessary: membrane binding, self-assembly, and the ability to recruit ESCRT machinery to catalyze the membrane fission reactions required for vesicle release.

Quasi-enveloped viral capsids were generated by modifying the capsid-forming Alpha proteins from two non-enveloped nodaviruses: Flock House (FHV) and Nodamuraviruses (NOV). The membrane-binding PH domain from phospholipase C (PH-PLC) and the ESCRT-recruiting p6 sequence from HIV-1 Gag were inserted within exposed surface loops of the capsid-forming Alpha protein (FIG. 2).

Quasi-enveloped viral capsids were generated by modifying the VP2 protein in the capsid of Adeno-associated virus. The membrane-binding 13 N-terminal amino acids of Lyn kinase, which include a myristoylation and a palmitoylation motif, and the ESCRT-recruiting p6 sequence from HIV-1 Gag, were inserted at the N terminus of the VP2 protein (FIG. 7).

1. Plasmid Design and Construction

The polypeptide sequences of the ESCRT-recruiting HIV-1 p6Gag domain and the membrane-binding PH domain were inserted into exposed surface loops of the Alpha proteins (at amino acid positions 264 and 206 of FHV Alpha, and at equivalent sites of NoV Alpha, see FIG. 2). These positions were chosen because others had shown that these loops can tolerate large polypeptide insertions without disrupting capsid assembly. These modified capsid proteins can be referred to as enveloped FHV (eFHV) and enveloped NoV (eNoV). Codon optimized genes encoding the FHV and NoV Alpha proteins were synthesized by GeneArt (ThemoFisher), and cloned into a CMV and CAG-based mammalian expression vector (pCMV, DNASU ID: EvNO00601609) by Gibson assembly. To create detectable controls that should not be released from cells, Myc epitope tags alone were introduced at the indicated positions (FIG. 3A). To create the quasi-enveloped constructs, Myc-p6-PH sequences were amplified by polymerase chain reactions (PCR) from EPN-25, and transferred into the indicated positions by Gibson assembly. Flexible 22GS linkers to allow more flexibility C-terminal to the PH domain were inserted. Constructs for eFHV, eNoV and the controls were all verified by sequencing, and they can be detected by western blotting using anti-Myc antibodies. A schematic of the final constructs is shown in FIG. 3A.

The polypeptide sequences of the ESCRT-recruiting HIV-1 $p6^{Gag}$ domain and the membrane-binding 13 N-terminal residues from Lyn Kinase that induce myristoyation and palmitoylation of the protein were inserted into the N terminus of AAV VP2. To uncouple expression of VP2 from VP1 and VP3, start codons for VP1 and VP2 were modified in the plasmid pXR2 by site-directed mutagenesis (see FIG. 7). A polynucleotide string comprising the Lyn1-13-p6-Myc sequence that also included a flexible 22GS linker C-terminal to the Myc-tag was synthesized and cloned into the pXR2-based VP2 expression vector by Gibson assembly. The N terminus of VP2 was truncated by around the horn mutagenesis.

2. Mammalian Cell Culture

All experiments were carried out in human embryonic kidney (HEK) 293T cells obtained from American Type Culture Collection (ATCC) and cultured at 37° C. and 5% CO2 in D-MEM media (ThermoFisher) containing 10% FBS, penicillin (100 U/ml) and streptomycin (0.1 mg/ml). Cells were tested for *Mycoplasma* contamination every 3 months using the MycoAlert™ *Mycoplasma* Detection Kit (Lonza).

3. Viron Release Assays

To assay release of the designed FHV and NoV constructs, $8\times10^5$ 293T cells were seeded in 6-well-plates 24 h prior to transfection. Cells were transfected with 2 μg of plasmid DNA expressing the FHV and NoV constructs (FIG. 3B), or co-transfected with 1 μg of plasmids expressing the FHV or NoV constructs and 1 μg of either pEGFP-VPS4A (E228Q) or pEGFP-C1 (Clonetech), using the polyethyleneimine method (PEI, Polysciences, 3 μl of PEI/μg DNA). The transfection media was replaced with 1.5 ml growth media 5 h later. Cells and culture supernatants were harvested 24 h post transfection. Released vesicles were collected from the culture supernatants by centrifugation through a 200 μl 20% sucrose cushion for 90 min at 21,000×g, 4° C., and denatured by adding 30 μl 1× Laemmli SDS-PAGE buffer and boiling for 5 min. Cells were lysed in 100 μl cold lysis buffer (50 mM Tris pH 7.4, 150 mM NaCl, 1% Triton X-100, protease inhibitors) and 100 μl 2× Laemmli buffer supplemented with 10% 2-mercaptoethanol (Sigma) and boiled for 10 min. 15 μl samples of the cellular lysates and released vesicles were separated by 8% SDS-PAGE, transferred onto PVDF membranes, and probed with antibodies against the Myc epitope. GAPDH protein was used as a loading control. Protein bands were visualized by probing the membrane with fluorescently labelled secondary antibodies (Li-Cor Biosciences), and scanning with an Odyssey Imager (Li-Cor Biosciences). Levels of expressed and released Myc-tagged proteins were quantified by western blot densitometry using ImageJ, and comparison to standard curves generated with known quantities of recombinant EPN-01* protein produced in *E. coli*. Release efficiencies are reported as the percentage of protein in pelleted supernatants vs. the sum of the protein in cells and pelleted supernatants.

FIG. 3B shows that eFHV eAlpha and eNoV capsids are released (lanes 2-4 and 6-8) whereas control Alpha constructs are not (lanes 1 and 5). Thus, the designed polypeptide insertions are required to drive efficient release. Note, Alpha constructs are released in the presence of eAlpha constructs (lanes 2, 3, 6, and 7), indicating that the proteins from an assembly. FIG. 3C shows that NoV eAlpha capsids are released (lanes 2-4, and 6-8) whereas control Alpha constructs are not (lanes 1 and 5). Thus, the designed polypeptide insertions are required to drive efficient release. Note, Alpha constructs are released in the presence of eAlpha constructs (lanes 2, 3, 6, and 7), indicating that the proteins from an assembly. FIG. 4B shows that overexpression of a dominant negative (DN-) VPS4A enzyme, which inhibits the ESCRT pathway, completely blocks the release of eFHV and eNoV (lanes 4 and 8). Thus, vesicle release is ESCRT dependent, as designed. Note that some "release" of non-enveloped NOV was detected when DN-VPS4A was co-expressed (lane 5), but this could reflect cell toxicity resulting from DN-VPS4A overexpression.

4. Vesicle Purification

Released vesicles used in biochemical and cryo-EM studies were purified from culture supernatants of 293T cells (T225 flask, 6×106 cells seeded per flask) following transient transfection with plasmids encoding eFHV and eNoV (30 μg/flask) using the PEI method. Transfected cells were incubated overnight and the media was replaced after 5 h with exosome production media (D-MEM supplemented with 10% FBS, depleted of contaminating extracellular particles by centrifugation overnight at 100,000×g at 4° C., and subsequently filtered through a 0.22 μm filter). Cells were grown for 48 h and extracellular vesicles were purified by a series of filtration and centrifugation steps. Briefly, cell debris was removed by centrifugation of the supernatant at 1,000×g for 5 min followed by filtration through a 0.22 µm filter (EMD Millipore). Vesicles were collected by centrifugation at 100,000×g in an SW32Ti (BeckmanCoulter) at 4° C. for 1 h. Pellets were resuspended in PBS and pooled in a single tube (SW41 rotor, BeckmanCoulter). PBS was added to fill the tube and vesicles were collected by centrifugation at 100,000×g at 4° C. for 1 h. Pellets were resuspended in 1 ml of PBS and concentrated by centrifugation at 100,000×g at 4° C. for 1 h in an OptimaMAX-E (BeckmanCoulter) benchtop ultracentrifuge using a TLS-55 rotor. FHV and NOV release levels were quantified by western blotting as described above.

5. Protease Protection Assays

Figure 4A:
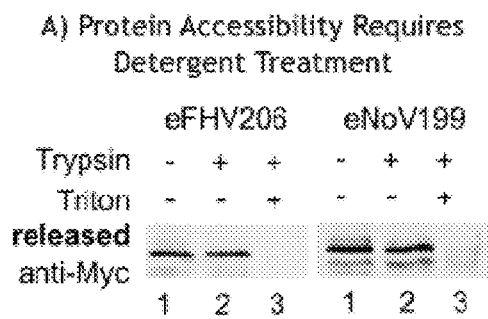
FIGS. 4A-B show that eFHV and eNoV bud inside membrane envelopes and that the release is ESCRT-dependent.
Figure 4B:
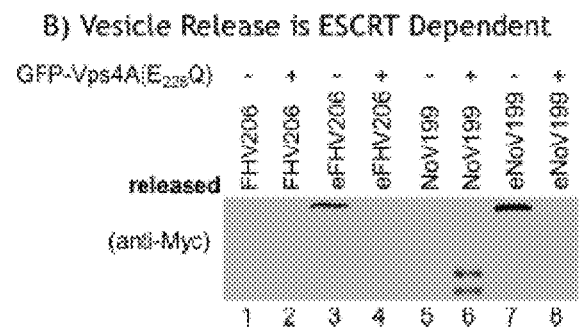

To test for membrane envelopment, purified vesicles were resuspended and incubated under three different conditions, 10 µl each: (i) untreated sample (FIG. 4A lane 1), (ii) sample+0.05 mg/ml trypsin (FIG. 4A lane 2), and (iii) sample+0.05 mg/ml trypsin+1% Triton X-100 (FIG. 4A lane 3). Samples were incubated for 30 min at 25° C. 1 mM PMSF was then added and the samples were incubated for 10 min at 25° C. to inactivate trypsin. Samples were denatured by boiling for 10 min in 4× Laemmli buffer supplemented with 5% 2-mercaptoethanol, and analyzed by SDS-PAGE/western blot using an anti-Myc antibody. FIG. 4A shows that both released eFHV and eNoV proteins were protected against trypsin digestion in the absence of detergent, but became susceptible to trypsin digestion in the presence of 1% Triton X-100.

6. Cryo-EM Tomographic Imaging of Vesicles

Figures 5A, 5B:
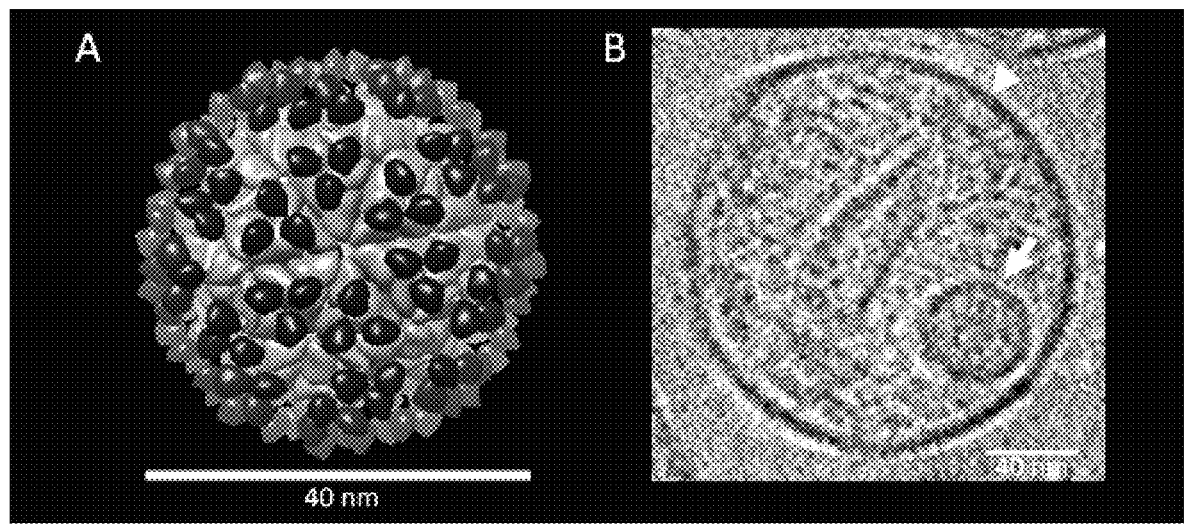
FIGS. 5A-B show evidence that eFHV is released inside a vesicle.
Figure 6A:
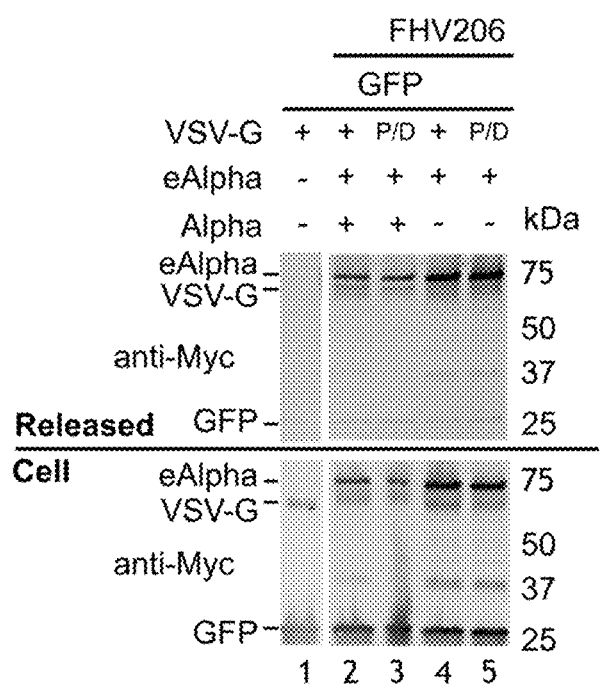
FIGS. 6A-B shows that eFHV can deliver cargo into target cells.
Figure 6B:
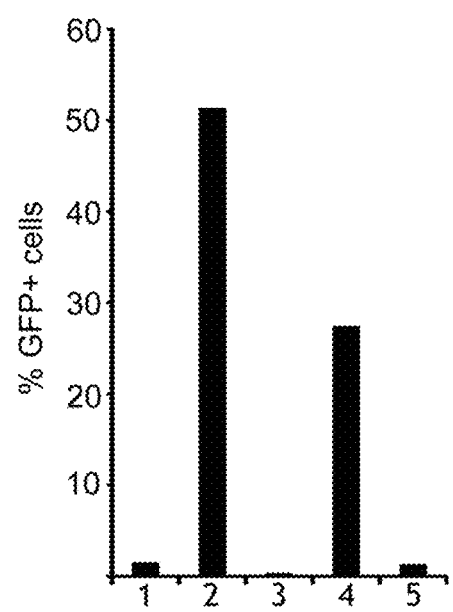
Figure 7:
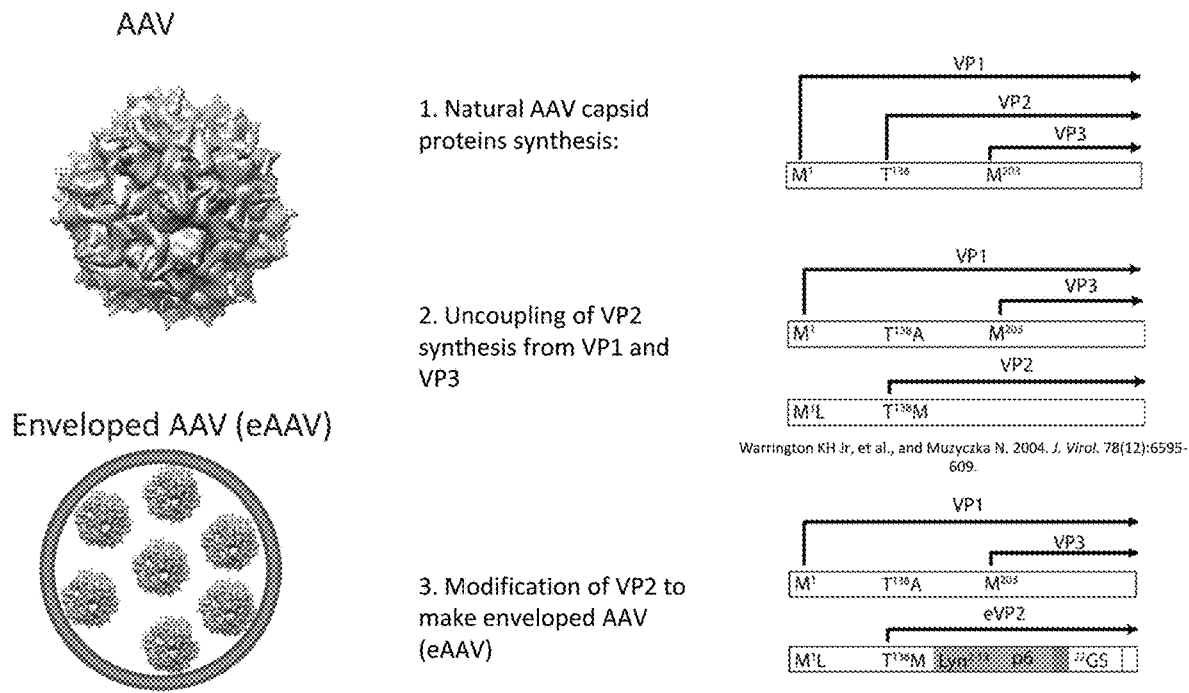
FIG. 7 shows the design of enveloped adeno-associated virus (AAV), eAAV.

To prepare samples for cryo-EM tomography, 3 µl of purified vesicles in PBS were mixed with 3 µl of BSA-coated gold fiducials (10 nm size, Electron Microscopy Sciences). 3.5 µl samples of the suspension were applied to glow-discharged R2/2 holey carbon coated EM grids (Quantifoil), within the environmental chamber of a Vitrobot Mark IV (FEI) maintained at 4° C., 80% relative humidity. Excess liquid was blotted from the grids for 1.5 s (blot force 20, 1 blot) with filter paper (Whatman), before plunge freezing in liquid ethane. Cryo-grids were placed in a Gatan 626 cryo-holder (Gatan) and imaged in a 200 kV Tecnai TF20 microscope (FEI) equipped with a K2 summit direct electron detector (Gatan). Tilt series were recorded bidirectionally starting from 0° to ±~600 with a 30 step size at a magnification of 22,500× and a defocus of ~8 µm (total dose per specimen ~300 e-/Å2), using the low-dose mode in SerialEM. Tomograms were generated using the IMOD software package. Image stacks were aligned and binned by 4 within IMOD. Aligned image stacks were Fourier filtered (cutoff 0.25, sigma 0.08) and tomographic reconstructions were performed using the simultaneous reconstruction technique (SIRT). Noise reduction was performed with the non-linear anisotropic diffusion (NAD) method in IMOD, using a K value of 0.04 with 12 iterations. FIG. 5B shows a slice from a tomogram that contains an icosahedral structure of the right size for FHV capsid (arrows), inside a vesicle membrane (arrowheads).

Those skilled in the art will recognize, or be able to ascertain using no more than routine experimentation, many equivalents to the specific embodiments of the method and compositions described herein. Such equivalents are intended to be encompassed by the following claims.

REFERENCES

1. Altan-Bonnet, N., *Extracellular vesicles are the Trojan horses of viral infection*. Current opinion in microbiology, 2016. 32: p. 77-81.
2. Votteler, J., et al., Designed proteins induce the formation of nanocage-containing extracellular vesicles. Nature, 2016. 540(7632): p. 292-295.
3. Manayani, D. J., et al., A viral nanoparticle with dual function as an anthrax antitoxin and vaccine. PLoS pathogens, 2007. 3(10).
4. Gibson, D. G., et al., Enzymatic assembly of DNA molecules up to several hundred kilobases. Nature Methods, 2009. 6(5): p. 343-345.
5. Kunkel, T. A., *Rapid and efficient site-specific mutagenesis without phenotypic selection*. Proceedings of the National Academy of Sciences of the United States of America, 1985. 82(2): p. 488-492.
6. Thery, C., et al., Isolation and characterization of exosomes from cell culture supernatants and biological fluids. Curr Protoc Cell Biol, 2006. Chapter 3: p. Unit 3 22.

We claim:

1. A modified virus comprising:

a) one or more capsids, wherein each of the one or more capsids comprises modified capsid proteins comprising a capsid forming protein, a membrane binding element and an endosomal sorting complex required for transport (ESCRT)-recruiting element, wherein the capsid forming protein is a capsid forming protein of a non-enveloped virus, wherein at least one of the membrane binding element and the ESCRT-recruiting element is heterologous to the capsid forming protein; and b) a membrane surrounding the one or more capsids, wherein the membrane does not comprise viral fusion proteins.

2. The modified virus of claim 1, wherein the membrane binding element is a membrane binding element of an enveloped virus.

3. The modified virus of claim 1, wherein the membrane binding element is membrane binding element of a non-enveloped virus.

4. The modified virus of claim 1, wherein the membrane binding element is a non-viral membrane binding protein.

5. The modified virus of claim 1, wherein the membrane binding element is a non-naturally occurring protein.

6. The modified virus of claim 1, wherein the ESCRT-recruiting element is an ESCRT-recruiting element of an enveloped virus.

7. The modified virus of claim 1, wherein the ESCRT-recruiting element is an ESCRT-recruiting element of a non-enveloped virus.

8. The modified virus of claim 1, wherein the membrane binding element and the ESCRT-recruiting element are a membrane binding element and an ESCRT-recruiting element of the same virus.

9. The modified virus of claim 1, wherein the membrane binding element is the membrane binding PH element from phospholipase C.

10. The modified virus of claim 1, wherein the membrane binding element is the membrane binding myristoylated and palmitoylated element of Lyn kinase.

11. The modified virus of claim 1, wherein the ESCRT-recruiting element is the $p6^{Gag}$ polypeptide from human immunodeficiency virus.

12. The modified virus of claim 1, wherein the ESCRT-recruiting element comprises any of SEQ ID NOs: 22, 23, 46-51, 154, 161-189.

13. The modified virus of claim 1, further comprising a desired cargo.

14. A method of treating a subject comprising administering a composition comprising the modified virus of claim 1 to a subject in need thereof.

* * * * *